US012758978B2

(12) United States Patent
Bixon et al.

(10) Patent No.: US 12,758,978 B2
(45) Date of Patent: Oct. 13, 2026

(54) TRANSFER STATION, INTERROGATION STATION, AND RELATED METHODS TO FACILITATE TRANSFER OF BIOLOGICAL SPECIMENS STORED AT CRYOGENIC CONDITIONS

(71) Applicant: TMRW Life Sciences, Inc., New York, NY (US)

(72) Inventors: Brian Bixon, Jersey City, NJ (US); Alexander Hultgren, Hamburg, NY (US); James Craven, Ely (GB)

(73) Assignee: TMRW Life Sciences, LLC, Coconut Creek, FL (US)

( * ) Notice: Subject to any disclaimer, the term of this patent is extended or adjusted under 35 U.S.C. 154(b) by 978 days.

(21) Appl. No.: 17/738,981

(22) Filed: May 6, 2022

(65) Prior Publication Data

US 2022/0355305 A1 Nov. 10, 2022

Related U.S. Application Data

(60) Provisional application No. 63/186,593, filed on May 10, 2021.

(51) Int. Cl.
*A01N 1/10* (2025.01)
*A01N 1/14* (2025.01)
(Continued)

(52) U.S. Cl.
CPC ............... *B01L 9/523* (2013.01); *B01L 3/545* (2013.01); *G06K 7/10316* (2013.01); (Continued)

(58) Field of Classification Search
None
See application file for complete search history.

(56) References Cited

U.S. PATENT DOCUMENTS 3,336,456 A 8/1967 Parmann
4,573,581 A 3/1986 Galloway et al.
(Continued)

FOREIGN PATENT DOCUMENTS

AU 2011357590 B2 9/2015
AU 2017287017 A1 1/2019
(Continued)

OTHER PUBLICATIONS

Japanese Office Action, dated Mar. 19, 2024, for corresponding Japanese Application No. 2023-519519, 15 pages.
(Continued)

*Primary Examiner* — Maris R Kessel
*Assistant Examiner* — Madison T. Herbert
(74) *Attorney, Agent, or Firm* — Cozen O'Connor

(57) ABSTRACT

A system and method facilitates transfers of specimen containers between a cryogenic freezer and a portable, bulk carrier. An interrogation station has a frame and a well that includes a bottom and at least one sidewall that extends upwardly from the bottom towards a top, wherein the bottom, the at least one sidewall, and the top collectively delineate an interior cavity of the well. The frame includes at least one opening that extends through the top so as to provide entry and access to the interior cavity of the well to receive buckets therein. The interrogation station further includes at least one array of antennas arranged within a plane and positioned beneath the bottom at a location in which the at least one array of antennas is aligned with the at least one opening along a vertical direction, which is perpendicular to the plane.

20 Claims, 24 Drawing Sheets

(51) Int. Cl.

| | |
|---|---|
| ***A01N 1/145*** | (2025.01) |
| ***A01N 1/147*** | (2025.01) |
| ***B01L 3/00*** | (2006.01) |
| ***B01L 9/00*** | (2006.01) |
| ***G06K 7/10*** | (2006.01) |
| ***G06K 17/00*** | (2006.01) |
| *C12N 5/00* | (2006.01) |

(52) U.S. Cl.

CPC .... *G06K 17/0029* (2013.01); *B01L 2300/022* (2013.01); *B01L 2300/0809* (2013.01); *C12N 5/547* (2025.01)

(56) References Cited

U.S. PATENT DOCUMENTS

| | | | |
|---|---|---|---|
| D300,583 | S | 4/1989 | Smith |
| 4,944,162 | A | 7/1990 | Lang et al. |
| D310,264 | S | 8/1990 | Leoncavallo et al. |
| 5,024,830 | A | 6/1991 | Linner |
| 5,176,202 | A | 1/1993 | Richard |
| 5,233,844 | A | 8/1993 | Knippscheer et al. |
| 5,355,684 | A | 10/1994 | Guice |
| 5,545,562 | A | 8/1996 | Cassou et al. |
| D382,809 | S | 8/1997 | Aldrich et al. |
| D382,810 | S | 8/1997 | Aldrich et al. |
| 5,711,446 | A | 1/1998 | Jeffs et al. |
| 5,741,462 | A | 4/1998 | Nova et al. |
| 5,751,629 | A | 5/1998 | Nova et al. |
| 5,874,214 | A | 2/1999 | Nova et al. |
| D408,145 | S | 4/1999 | Au |
| 5,921,102 | A | 7/1999 | Vago |
| 5,925,562 | A | 7/1999 | Nova et al. |
| 5,964,095 | A | 10/1999 | Coelho et al. |
| 6,066,300 | A | 5/2000 | Carey et al. |
| 6,100,026 | A | 8/2000 | Nova et al. |
| 6,141,975 | A | 11/2000 | Tatsumi |
| 6,156,566 | A | 12/2000 | Bryant |
| 6,302,327 | B1 | 10/2001 | Coelho et al. |
| 6,329,139 | B1 | 12/2001 | Nova et al. |
| 6,564,120 | B1 | 5/2003 | Richard et al. |
| D484,797 | S | 1/2004 | Kipperman et al. |
| 6,701,743 | B1 | 3/2004 | Durst et al. |
| D496,398 | S | 9/2004 | Greenberg |
| 6,888,063 | B1 | 5/2005 | Lien et al. |
| D506,550 | S | 6/2005 | Greenberg |
| 7,070,053 | B1 | 7/2006 | Abrams et al. |
| 7,091,864 | B2 | 8/2006 | Veitch et al. |
| D535,478 | S | 1/2007 | Uffner et al. |
| 7,228,198 | B2 | 6/2007 | Vollm et al. |
| 7,278,328 | B2 | 10/2007 | Massaro |
| 7,316,896 | B2 | 1/2008 | Kuwayama et al. |
| 7,350,703 | B2 | 4/2008 | Ambartsoumian |
| 7,411,508 | B2 | 8/2008 | Harazin et al. |
| D576,488 | S | 9/2008 | Miota et al. |
| D592,966 | S | 5/2009 | Nissen |
| 7,661,591 | B2 | 2/2010 | Dearing et al. |
| 7,694,886 | B2 | 4/2010 | Tan et al. |
| 7,861,540 | B2 | 1/2011 | Cloutier et al. |
| 7,870,748 | B2 | 1/2011 | Byrne |
| D642,697 | S | 8/2011 | Gaefvert |
| 8,097,199 | B2 | 1/2012 | Abbott et al. |
| 8,098,162 | B2 | 1/2012 | Abbott et al. |
| 8,115,599 | B2 | 2/2012 | Harazin et al. |
| 8,168,138 | B2 | 5/2012 | Che et al. |
| 8,378,827 | B2 | 2/2013 | Davidowitz et al. |
| D682,045 | S | 5/2013 | Myoung |
| 8,444,058 | B2 | 5/2013 | Masin |
| 8,502,645 | B2 | 8/2013 | Thomas et al. |
| 8,710,958 | B2 | 4/2014 | Yang et al. |
| 8,790,597 | B2 | 7/2014 | Childs et al. |
| 8,852,536 | B2 | 10/2014 | Davidowitz et al. |
| 8,872,627 | B2 | 10/2014 | Davidowitz |
| 8,884,743 | B2 | 11/2014 | Chaffey et al. |
| 8,919,532 | B2 | 12/2014 | Buergermeister et al. |
| 8,937,550 | B2 | 1/2015 | Phaneuf et al. |
| 9,028,754 | B2 | 5/2015 | Winter et al. |
| 9,033,251 | B2 | 5/2015 | Weisshaupt et al. |
| D733,314 | S | 6/2015 | Lui |
| 9,140,487 | B2 | 9/2015 | Chaffey et al. |
| 9,163,869 | B2 | 10/2015 | Warhurst et al. |
| 9,211,540 | B2 | 12/2015 | Lansdowne |
| 9,280,738 | B2 | 3/2016 | Dor et al. |
| 9,289,770 | B2 | 3/2016 | Lavi |
| 9,297,499 | B2 | 3/2016 | Jimenez-Rios et al. |
| 9,418,265 | B2 | 8/2016 | Morris et al. |
| 9,431,692 | B2 | 8/2016 | Davidowitz et al. |
| D768,868 | S | 10/2016 | Inoue |
| D771,271 | S | 11/2016 | Zingre |
| 9,501,734 | B2 | 11/2016 | Morris |
| 9,516,876 | B2 | 12/2016 | Inoue |
| D777,941 | S | 1/2017 | Piramoon |
| 9,538,746 | B2 | 1/2017 | Inoue |
| 9,538,747 | B2 | 1/2017 | Inoue |
| 9,547,782 | B2 | 1/2017 | Lansdowne |
| 9,551,649 | B2 | 1/2017 | Houghton et al. |
| 9,589,225 | B2 | 3/2017 | Morris |
| 9,619,678 | B2 | 4/2017 | Morris et al. |
| 9,697,457 | B2 | 7/2017 | Morris |
| 9,723,832 | B2 | 8/2017 | Camenisch et al. |
| 9,736,890 | B2 | 8/2017 | Chaffey et al. |
| 9,764,325 | B2 | 9/2017 | Davidowitz |
| 9,796,574 | B2 | 10/2017 | Frey et al. |
| 9,835,640 | B2 | 12/2017 | Raicu et al. |
| 9,902,068 | B1 | 2/2018 | Sestok et al. |
| 9,928,457 | B2 | 3/2018 | Mcdowell |
| D816,165 | S | 4/2018 | Haug |
| D835,472 | S | 12/2018 | Seiders et al. |
| 10,156,386 | B2 | 12/2018 | Bartlett et al. |
| D840,684 | S | 2/2019 | Luburic |
| 10,207,270 | B2 | 2/2019 | Lansdowne |
| 10,241,015 | B2 | 3/2019 | Hollabaugh et al. |
| D845,139 | S | 4/2019 | Wilson et al. |
| 10,328,431 | B2 | 6/2019 | Davidowitz |
| 10,401,082 | B2 | 9/2019 | Coradetti et al. |
| 10,493,457 | B2 | 12/2019 | Croquette et al. |
| 10,531,657 | B2 | 1/2020 | Farrington et al. |
| D874,875 | S | 2/2020 | Huang |
| 10,561,141 | B2 | 2/2020 | Suzuki et al. |
| D881,568 | S | 4/2020 | Luburic |
| 10,677,810 | B2 | 6/2020 | Grimwood et al. |
| D890,948 | S | 7/2020 | Figueredo et al. |
| 10,748,050 | B2 | 8/2020 | Morris et al. |
| D910,836 | S | 2/2021 | Sandberg et al. |
| 10,973,226 | B2 | 4/2021 | Blair et al. |
| 10,989,636 | B2 | 4/2021 | Gutelius et al. |
| D928,343 | S | 8/2021 | Bonnoitt et al. |
| D930,186 | S | 9/2021 | Kim |
| D931,128 | S | 9/2021 | Li |
| D932,906 | S | 10/2021 | Schulz |
| 11,148,143 | B2 | 10/2021 | Davidowitz et al. |
| 11,175,298 | B2 | 11/2021 | Neeper et al. |
| 11,186,421 | B2 | 11/2021 | Brothers |
| D938,053 | S | 12/2021 | Xiao |
| D945,271 | S | 3/2022 | Halgren et al. |
| D963,194 | S | 9/2022 | Bixon et al. |
| D981,801 | S | 3/2023 | Wu |
| 11,697,119 | B2 | 7/2023 | Davidowitz et al. |
| 12,006,126 | B2 | 6/2024 | Davidowitz et al. |
| 12,527,318 | B2 | 1/2026 | Craven et al. |
| 2002/0030972 | A1 | 3/2002 | Ali et al. |
| 2002/0190845 | A1 | 12/2002 | Moore |
| 2002/0195234 | A1 | 12/2002 | Wu |
| 2002/0196146 | A1 | 12/2002 | Moore |
| 2003/0017082 | A1 | 1/2003 | Van Deursen et al. |
| 2003/0174046 | A1 | 9/2003 | Abrams |
| 2004/0100415 | A1 | 5/2004 | Veitch et al. |
| 2004/0227617 | A1 | 11/2004 | Vasquez et al. |
| 2004/0245329 | A1 | 12/2004 | Huang |
| 2004/0265831 | A1 | 12/2004 | Arav et al. |
| 2005/0005614 | A1 | 1/2005 | Iarocci et al. |
| 2005/0016198 | A1 | 1/2005 | Wowk et al. |
| 2005/0058483 | A1 | 3/2005 | Chapman et al. |
| 2005/0237195 | A1 | 10/2005 | Urban |

(56) References Cited

U.S. PATENT DOCUMENTS

2005/0247782 A1 11/2005 Ambartsoumian
2006/0051239 A1 3/2006 Massaro
2006/0283945 A1 12/2006 Excoffier et al.
2007/0034226 A1 2/2007 Ferkel
2007/0068208 A1 3/2007 Norman et al.
2007/0150375 A1 6/2007 Yang
2007/0172396 A1 7/2007 Neeper et al.
2007/0267419 A1 11/2007 Fuhr et al.
2008/0012687 A1 1/2008 Rubinstein
2008/0024301 A1 1/2008 Fritchie et al.
2008/0121700 A1 5/2008 Dearing et al.
2008/0239478 A1 10/2008 Tafas et al.
2009/0015430 A1 1/2009 Harazin et al.
2009/0026907 A1 1/2009 Davidowitz et al.
2009/0029341 A1 1/2009 Fuhr et al.
2009/0153993 A1 6/2009 Garcia et al.
2009/0188272 A1 7/2009 Cloutier et al.
2009/0318751 A1 12/2009 Lansdowne
2009/0322486 A1 12/2009 Gerstel
2010/0028214 A1 2/2010 Howard et al.
2010/0123551 A1 5/2010 Fritchie
2010/0141384 A1 6/2010 Chen et al.
2010/0281886 A1 11/2010 Shaham et al.
2010/0302040 A1 12/2010 Davidowitz et al.
2010/0318217 A1 12/2010 Ferrer et al.
2011/0088424 A1 4/2011 Cloutier et al.
2011/0088517 A1 4/2011 Tsujimura et al.
2011/0120148 A1 5/2011 Yoshimura et al.
2011/0137812 A1 6/2011 Sherga
2011/0143452 A1 6/2011 Che et al.
2011/0181875 A1 7/2011 Nakahana et al.
2011/0199187 A1 8/2011 Davidowitz
2011/0199188 A1 8/2011 Dickson
2011/0214243 A1 9/2011 Major
2011/0251982 A1 10/2011 Dluhos et al.
2011/0308271 A1 12/2011 Schryver
2011/0312102 A1 12/2011 Jo
2012/0060514 A1 3/2012 Warhurst et al.
2012/0060520 A1 3/2012 Collins et al.
2012/0060539 A1 3/2012 Hunt et al.
2012/0060541 A1 3/2012 Hunt et al.
2012/0064603 A1 3/2012 Childs et al.
2012/0167786 A1 7/2012 Laugharn, Jr.
2012/0187197 A1 7/2012 Masin
2012/0212330 A1* 8/2012 Halberthal ............... H01Q 7/00
343/742
2012/0256806 A1 10/2012 Davidowitz et al.
2012/0272500 A1 11/2012 Reuteler
2012/0293338 A1 11/2012 Chaffey et al.
2013/0011226 A1 1/2013 Camenisch et al.
2013/0048711 A1 2/2013 Burns et al.
2013/0076215 A1 3/2013 Davidowitz et al.
2013/0106579 A1 5/2013 Aubert et al.
2013/0119562 A1 5/2013 Shimizu et al.
2013/0151004 A1 6/2013 Winter et al.
2013/0152710 A1 6/2013 Laugharn et al.
2013/0217107 A1 8/2013 Pederson et al.
2013/0236276 A1 9/2013 Richter
2013/0342320 A1 12/2013 Hinman et al.
2014/0008042 A1 1/2014 Schryver et al.
2014/0008355 A1 1/2014 Chaffey et al.
2014/0069119 A1 3/2014 Katkov et al.
2014/0081445 A1 3/2014 Villamar
2014/0157798 A1 6/2014 Jimenez-Rios et al.
2014/0171829 A1 6/2014 Holmes et al.
2014/0230472 A1 8/2014 Coradetti et al.
2014/0352456 A1 12/2014 Davidowitz
2015/0045782 A1 2/2015 Ottanelli
2015/0084771 A1 3/2015 Nikitin et al.
2015/0122887 A1* 5/2015 Morris ............... G06K 7/10336
235/440
2015/0125574 A1 5/2015 Arent et al.
2015/0153369 A1 6/2015 Giovanoli
2015/0204598 A1* 7/2015 Affleck .................. A01N 1/145
2015/0205986 A1 7/2015 Morris et al.
2015/0273468 A1 10/2015 Croquette et al.
2015/0295328 A1 10/2015 Fireaizen
2015/0356398 A1 12/2015 Morris
2015/0379390 A1 12/2015 Morris
2016/0026911 A1 1/2016 Morris et al.
2016/0063287 A1 3/2016 Birrer et al.
2016/0085913 A1 3/2016 Evans et al.
2016/0086003 A1 3/2016 Nikitin
2016/0095309 A1 4/2016 Reuteler
2016/0101908 A1 4/2016 Minnette et al.
2016/0143270 A1 5/2016 Schryver
2016/0175837 A1 6/2016 Chaffey et al.
2016/0232487 A1 8/2016 Yonker
2016/0236387 A1 8/2016 Carroll et al.
2016/0288999 A1 10/2016 Caveney et al.
2016/0289000 A1 10/2016 Caveney et al.
2016/0341464 A1 11/2016 Bagwell
2016/0349172 A1 12/2016 Houghton et al.
2016/0353730 A1 12/2016 Harston et al.
2016/0358062 A1 12/2016 Morris
2016/0367188 A1 12/2016 Malik et al.
2017/0113909 A1 4/2017 Frey et al.
2017/0122846 A1 5/2017 Holmes et al.
2017/0146636 A1 5/2017 Alicot et al.
2017/0156312 A1 6/2017 Farrington et al.
2017/0166865 A1 6/2017 Peng
2017/0184479 A1 6/2017 Schryver et al.
2017/0190056 A1 7/2017 Lapham et al.
2017/0286903 A1* 10/2017 Elizondo, II ......... G06Q 10/087
2017/0320054 A1 11/2017 Crum et al.
2018/0020659 A1 1/2018 Camenisch et al.
2018/0043364 A1 2/2018 Davidowitz
2018/0055042 A1 3/2018 Sarmentero Ortiz
2018/0086533 A1 3/2018 Kjelland
2018/0100868 A1 4/2018 Grimwood et al.
2018/0128210 A1 5/2018 Garner
2018/0135806 A1 5/2018 Qu et al.
2018/0137315 A1 5/2018 Johns et al.
2018/0154359 A1 6/2018 Ueyama
2018/0202908 A1 7/2018 Croquette et al.
2018/0272353 A1 9/2018 Malin
2018/0313498 A1 11/2018 Antola et al.
2018/0368394 A1 12/2018 Kjelland et al.
2019/0000073 A1 1/2019 Pedersen et al.
2019/0005304 A1 1/2019 Adalsteinsson et al.
2019/0025280 A1 1/2019 Kaditz et al.
2019/0060892 A1 2/2019 Davidowitz et al.
2019/0092555 A1 3/2019 Ma et al.
2019/0162639 A1 5/2019 Gutelius et al.
2019/0193078 A1 6/2019 Fiondella et al.
2019/0215948 A1* 7/2019 Arnitz ................. H01L 23/3675
2019/0250181 A1 8/2019 Seeber
2019/0276233 A1 9/2019 Caveney et al.
2019/0277868 A1 9/2019 Privat De Fortune et al.
2019/0293344 A1 9/2019 Sun et al.
2019/0297877 A1 10/2019 Komatsu et al.
2020/0093122 A1 3/2020 Lin et al.
2020/0097788 A1 3/2020 Pedersen et al.
2020/0107541 A1* 4/2020 Blair ...................... G01K 1/024
2020/0143930 A1 5/2020 Catchings et al.
2020/0229427 A1 7/2020 Kilbride et al.
2020/0229429 A1 7/2020 Blair et al.
2020/0229430 A1 7/2020 Blair et al.
2020/0229431 A1 7/2020 Blair et al.
2020/0248638 A1 8/2020 Engfehr et al.
2020/0281191 A1 9/2020 Ally et al.
2020/0319625 A1 10/2020 Morris et al.
2020/0386649 A1 12/2020 Baird et al.
2021/0039937 A1 2/2021 Tansey et al.
2021/0121876 A1 4/2021 Blair et al.
2021/0135061 A1 5/2021 Navabi
2021/0244018 A1 8/2021 Sandy et al.
2022/0087253 A1 3/2022 Gupta et al.
2022/0136656 A1 5/2022 Clarke et al.
2022/0192182 A1 6/2022 Bixon et al.
2022/0221476 A1 7/2022 Craven et al.
2023/0329230 A1 10/2023 Li et al.

(56) References Cited

U.S. PATENT DOCUMENTS

| | | | |
|---|---|---|---|
| 2024/0159433 | A1 | 5/2024 | Brooks et al. |
| 2024/0428601 | A1 | 12/2024 | Flores-saiffe Farias et al. |

FOREIGN PATENT DOCUMENTS

| | | | | |
|---|---|---|---|---|
| CA | 2972315 | A1 | 8/2016 | |
| CN | 102456118 | A | 5/2012 | |
| CN | 105857932 | A | 8/2016 | |
| CN | 105890965 | A | 8/2016 | |
| CN | 106102460 | A | 11/2016 | |
| CN | 205815766 | U | 12/2016 | |
| CN | 106370879 | A | 2/2017 | |
| CN | 106871546 | A | 6/2017 | |
| CN | 107624751 | A | 1/2018 | |
| CN | 108112576 | A | 6/2018 | |
| CN | 207595583 | U | 7/2018 | |
| CN | 207663251 | U | 7/2018 | |
| CN | 207675193 | U | 7/2018 | |
| CN | 108541702 | A | 9/2018 | |
| CN | 109258627 | A | 1/2019 | |
| CN | 208425434 | U | 1/2019 | |
| CN | 109922887 | A | 6/2019 | |
| CN | 110476952 | A | 11/2019 | |
| CN | 110517737 | A | 11/2019 | |
| CN | 209677194 | U | 11/2019 | |
| CN | 110550327 | A | 12/2019 | |
| CN | 110583618 | A | 12/2019 | |
| CN | 110589332 | A | 12/2019 | |
| CN | 110645752 | A | 1/2020 | |
| CN | 110667986 | A | 1/2020 | |
| CN | 210614415 | U | 5/2020 | |
| CN | 210709605 | U | 6/2020 | |
| CN | 210709624 | U | 6/2020 | |
| CN | 210711515 | U | 6/2020 | |
| CN | 111357738 | A | 7/2020 | |
| CN | 111418578 | A | 7/2020 | |
| CN | 111771211 | A | 10/2020 | |
| CN | 112090469 | A | 12/2020 | |
| CN | 112189657 | A | 1/2021 | |
| CN | 112325976 | A | 2/2021 | |
| CN | 112325978 | A | 2/2021 | |
| CN | 112340334 | A | 2/2021 | |
| CN | 112841172 | A | 5/2021 | |
| CN | 213274464 | U | 5/2021 | |
| CN | 112894791 | A | 6/2021 | |
| CN | 213863260 | U | 8/2021 | |
| CN | 213863569 | U | 8/2021 | |
| CN | 213872207 | U | 8/2021 | |
| CN | 213874569 | U | 8/2021 | |
| CN | 213995979 | U | 8/2021 | |
| CN | 214006820 | U | 8/2021 | |
| CN | 214216855 | U | 9/2021 | |
| CN | 214358041 | U | 10/2021 | |
| CN | 214398091 | U | 10/2021 | |
| CN | 214758843 | U | 11/2021 | |
| CN | 115352743 | A | 11/2022 | |
| CN | 219596677 | U | 8/2023 | |
| DE | 102011012887 | A1 | 8/2012 | |
| DE | 102016008869 | A1 | 1/2018 | |
| EP | 0411224 | A2 | 2/1991 | |
| EP | 0706825 | A1 | 4/1996 | |
| EP | 0811140 | B1 | 12/1997 | |
| EP | 1002211 | A2 | 5/2000 | |
| EP | 1366998 | A2 | 3/2004 | |
| EP | 1366998 | B1 | 1/2006 | |
| EP | 1916492 | A1 | 4/2008 | |
| EP | 2301857 | A1 | 3/2011 | |
| EP | 2315163 | A1 | 4/2011 | |
| EP | 2358196 | A1 | 8/2011 | |
| EP | 2467465 | A1 | 6/2012 | |
| EP | 2124171 | B1 | 8/2012 | |
| EP | 2666694 | B1 | 7/2014 | |
| EP | 1888239 | B1 | 10/2014 | |
| EP | 1981692 | B1 | 6/2015 | |
| EP | 2498968 | B1 | 9/2015 | |
| EP | 2335182 | B1 | 10/2015 | |
| EP | 2297736 | B1 | 2/2016 | |
| EP | 2292332 | B1 | 7/2016 | |
| EP | 2765183 | B1 | 7/2016 | |
| EP | 2614320 | B1 | 10/2016 | |
| EP | 2354729 | B1 | 12/2016 | |
| EP | 2873497 | B1 | 5/2017 | |
| EP | 2948247 | B1 | 11/2017 | |
| EP | 3336456 | A1 | 6/2018 | |
| EP | 2743865 | B1 | 6/2019 | |
| EP | 2866938 | B1 | 6/2019 | |
| EP | 3514732 | A1 | 7/2019 | |
| EP | 2232175 | B1 | 8/2019 | |
| EP | 3539899 | A1 | 9/2019 | |
| EP | 2965266 | B1 | 10/2019 | |
| EP | 2492663 | B1 | 12/2019 | |
| EP | 3655892 | A1 | 5/2020 | |
| EP | 3228191 | B1 | 8/2020 | |
| EP | 4252009 | A4 | 4/2024 | |
| ES | 2467465 | A2 | 6/2014 | |
| ES | 2595984 | T3 | 1/2017 | |
| FR | 3095602 | A1 * | 11/2020 | |
| JP | 2000137031 | A | 5/2000 | |
| JP | 2001142861 | A | 5/2001 | |
| JP | 2004028595 | A | 1/2004 | |
| JP | 2005009863 | A | 1/2005 | |
| JP | 2005239366 | A | 9/2005 | |
| JP | 2005321935 | A | 11/2005 | |
| JP | 2007066011 | A | 3/2007 | |
| JP | 2007235905 | A | 9/2007 | |
| JP | 2007532867 | A | 11/2007 | |
| JP | 2008021082 | A | 1/2008 | |
| JP | 2008522184 | A | 6/2008 | |
| JP | 2010521725 | A | 6/2010 | |
| JP | 2012526966 | A | 11/2012 | |
| JP | 5278978 | B2 | 5/2013 | |
| JP | 2014174647 | A | 9/2014 | |
| JP | 2015019244 | A | 1/2015 | |
| JP | 2015087306 | A | 5/2015 | |
| JP | 2017508984 | A | 3/2017 | |
| JP | 2017514499 | A | 6/2017 | |
| JP | 2017165487 | A | 9/2017 | |
| JP | 2018511782 | A | 4/2018 | |
| JP | 6343934 | B2 | 6/2018 | |
| JP | 2018136246 | A | 8/2018 | |
| JP | 2018529062 | A | 10/2018 | |
| JP | 2019505042 | A | 2/2019 | |
| JP | 2019518974 | A | 7/2019 | |
| JP | 2019529938 | A | 10/2019 | |
| JP | 2019536973 | A | 12/2019 | |
| JP | 2020079797 | A | 5/2020 | |
| KR | 20080070015 | A | 7/2008 | |
| KR | 102368093 | B1 | 2/2022 | |
| WO | 9216800 | A1 | 10/1992 | |
| WO | 0018225 | A1 | 4/2000 | |
| WO | 0105687 | A1 | 1/2001 | |
| WO | 0194016 | A1 | 12/2001 | |
| WO | 02081743 | A2 | 10/2002 | |
| WO | 03061381 | A1 | 7/2003 | |
| WO | 2004026661 | A1 | 4/2004 | |
| WO | 2005093641 | A1 | 10/2005 | |
| WO | 2005109332 | A1 | 11/2005 | |
| WO | 2005115621 | A1 | 12/2005 | |
| WO | 2006029110 | A1 | 3/2006 | |
| WO | 2007024540 | A1 | 3/2007 | |
| WO | 2007049039 | A1 | 5/2007 | |
| WO | 2007075253 | A2 | 7/2007 | |
| WO | 2007092119 | A1 | 8/2007 | |
| WO | 2008024471 | A2 | 2/2008 | |
| WO | 2008057150 | A1 | 5/2008 | |
| WO | 2009004366 | A1 | 1/2009 | |
| WO | WO-2009003231 | A1 * | 1/2009 | ............. A61B 90/90 |
| WO | 2009017558 | A1 | 2/2009 | |
| WO | 2009094071 | A3 | 10/2009 | |
| WO | 2009120596 | A1 | 10/2009 | |
| WO | 2009155638 | A1 | 12/2009 | |
| WO | 2010037166 | A1 | 4/2010 | |
| WO | 2011069190 | A1 | 6/2011 | |
| WO | 2011159934 | A2 | 12/2011 | |

(56) References Cited

FOREIGN PATENT DOCUMENTS

| | | | |
|---|---|---|---|
| WO | 2012083396 | A1 | 6/2012 |
| WO | 2012100281 | A1 | 8/2012 |
| WO | 2012033605 | A3 | 11/2012 |
| WO | 2012033994 | A3 | 12/2012 |
| WO | 2012033992 | A3 | 4/2013 |
| WO | 2013053011 | A1 | 4/2013 |
| WO | 2010014656 | A3 | 5/2013 |
| WO | 2012034037 | A3 | 5/2013 |
| WO | 2014001819 | A1 | 1/2014 |
| WO | 2014006417 | A1 | 1/2014 |
| WO | 2014009729 | A1 | 1/2014 |
| WO | 2014114938 | A2 | 7/2014 |
| WO | 2014135890 | A1 | 9/2014 |
| WO | 2014157798 | A1 | 10/2014 |
| WO | 2014191757 | A1 | 12/2014 |
| WO | 2015073964 | A1 | 5/2015 |
| WO | 2015109315 | A3 | 10/2015 |
| WO | 2015162680 | A1 | 10/2015 |
| WO | 2016081755 | A1 | 5/2016 |
| WO | 2016120224 | A1 | 8/2016 |
| WO | 2016160984 | A1 | 10/2016 |
| WO | 2016160986 | A3 | 11/2016 |
| WO | 2016200519 | A1 | 12/2016 |
| WO | 2017014999 | A1 | 1/2017 |
| WO | 2017075144 | A1 | 5/2017 |
| WO | 2017109153 | A1 | 6/2017 |
| WO | 2017149468 | A1 | 9/2017 |
| WO | 2017215957 | A1 | 12/2017 |
| WO | 2018000051 | A1 | 1/2018 |
| WO | 2018002287 | A1 | 1/2018 |
| WO | 2018005129 | A1 | 1/2018 |
| WO | 2018025053 | A1 | 2/2018 |
| WO | 2018039727 | A1 | 3/2018 |
| WO | 2018041516 | A1 | 3/2018 |
| WO | 2018097267 | A1 | 5/2018 |
| WO | 2018215588 | A1 | 11/2018 |
| WO | 2019005450 | A1 | 1/2019 |
| WO | 2019182900 | A1 | 9/2019 |
| WO | 2020033578 | A1 | 2/2020 |
| WO | 2020072945 | A1 | 4/2020 |
| WO | 2021086983 | A1 | 5/2021 |
| WO | 2022066943 | A1 | 3/2022 |
| WO | 2022072646 | A1 | 4/2022 |
| WO | 2022155225 | A1 | 7/2022 |

OTHER PUBLICATIONS

"BioStore (TM) III Cryo" 2015, pp. 1-1, XP093203663, Internet Retrieved from the Internet: URL:https://corecryolab.com/wp-content/uploads/2016/04/Brooks-BioStore-III-Cryo-One-Pager-Automation.

Document titled Description DE102016008869A1, machine translation of DE102016008869A1 provided by Espacenet, original document published 2018, original document already made of record in Applicant's Jun. 10, 2024 IDS (Year: 2018).

Environmental design, eight edition, The Charted institution of Building Services Engineers, 2016, section 3-36.

EP Search Report in EP App No. 22808100.6, mailed Mar. 6, 2025, 9 pages.

EP Search Report mailed Dec. 19, 2024, in European Patent Application No. 22879511.8, 8 pages.

European Patent Search Report mailed Sep. 27, 2024 in EP Application No. 21873453.1. in 6 pages.

European Search Report dated Sep. 20, 2024, for European Application No. 20955465.8 in 7 pages.

Extended European Search Report dated Dec. 18, 2024, for European Application No. 21911908.8-1014, 9 pages.

Extended European Search Report for European Application No. 21876482.7, dated Oct. 2, 2024, 7 pages.

Extended European Search Report for European Application No. 21904425.2, dated Oct. 9, 2024, 9 pages.

Non Final Office Action for U.S. Appl. No. 17/552,327, mailed Feb. 10, 2025,15 pages.

Notice of Allowance, mailed Feb. 14, 2025, for U.S. Appl. No. 18/113,297, 27 pages.

"BioStoreTM III Automated LN2 Sample Storage Solutions", Mar. 17, 2020 (Mar. 17, 2020), pp. 1-6, XP093203686.

International Search Report and Written Opinion for PCT/US2022/028185, mailed Aug. 26, 2022, 11 pages.

Non Final Office Action for U.S. Appl. No. 17/083,179, mailed Sep. 1, 2022, 8 pages.

Non Final Office Action for U.S. Appl. No. 17/321,174, mailed Nov. 22, 2022, 26 pages.

"Abeyance Web App / Stay Connected", Jul. 6, Abeyance Cry Solutions—Abeyateck, LLC, 2021, 3 pages.

"IVF Witness System: RI Witness TM ART Management System", Confidence, Efficiency and Trust, IVF Witness System—RI Witness—CooperSurgical Fertility Companies https//fertility.coopersurgical.com/equipment/ri-witness—Apr. 19, 2021, 28 pages.

"RI Witness—Confidence, Efficiency and Trust", CooperSurgical, Fertility and Genomic Solutions, Order No. WIT_BRO_001_V13_ROW—Oct. 13, 2020, 13 pages.

"RI Witness—Product guide", CooperSurgical Fertility and Genomic Solutions, Order No. EQU_BRO_004, V1: ROW Oct. 24, 2018, 12 pages.

"S840 Lab Mover", Large Volume LNS Dry Vapor Shipper, Products Shipping, Jul. 6, Abeyance Cry Solutions—Abeyateck, LLC, 2021, 3 pages.

"Simple, Secure—190° C. LN2 Vapor Storage", Products Shipping, Jul. 6, Abeyance Cry Solutions—Abeyateck, LLC, 2021, 7 pages.

Brady printer Range, "Everyone is Unique" Continual cryopreservation monitoring from RI Witness, CooperSurgical, Inc. Order No. WIT_FLY_010_V2_US Oct. 14, 2020, 3 pages.

Comley, J., "New approaches to sample identification tracking and technologies for maintaining the quality of stored samples," Drug Discovery World Summer 2017, 11 pages.

CooperSurgical, RI Witness, Order No. CE 60010312 Version 3-ROW: Oct. 24, 2018, 12 pages.

Cryogenic Vials, Standard. Online, published date unknown. Retrieved on Dec. 8, 2021 from URL: https://www.nextdayscience.com/cryogenic-vials-standard.htm.

CX100 Cryo Express Dry Shipper With Shipping Case. Online, published date unknown. Retrieved on May 24, 2022 from URL:https://www.mitegen.com/product/cryo-express-dry-shipper-cx100-with-case, 2 pages.

FluidX Tri-Coded Jacket: 0.7ml Sample Storage Tube with External Thread; Brooks Life Sciences; https://bioinventory.biostorage.com.

HID Beyond Cool: RFID disentangles cryopreservation storage and management, 2015, 4 pages.

Ihmig et al., "Frozen cells and bits," IEEE Pulse, Sep. 2013, 9 pages.

International Preliminary Report on Patentability and Written Opinion from PCT Application No. PCT/GB2005/002048 dated Aug. 23, 2005, 9 pages.

International Search Report and Written Opinion for International Application No. PCT/US2020/057779, Mailed on Jun. 17, 2021, 12 pages.

International Search Report and Written Opinion for PCT/US2020/057764, Mailed Date: Feb. 19, 2021, 14 pages.

Notice of Reasons for Refusal, Japanese Application No. 2023-534389, dated May 28, 2024, 9 pages.

Notice of Reasons for Refusal, Japanese Application No. 2023-535428, dated May 30, 2024, 11 pages.

Euopean Search Report mailed Jun. 30, 2022 in App No. 19869478.8.

"Secure Your Future with Cryofuture", Https://cryofuture.com, 2004, 13 pages.

"Your Partner for Local and Secure Cryostorage and Transportation", http://cryofuture.com, Clinic's workflow, 2024, 12 pages.

Australian Examination Report mailed Feb. 26, 2024, Application No. 2021348066, 8 pages.

Notice of Reasons for Refusal, Japanese Application No. 2023-541871, dated Apr. 24, 2024, 3 pages.

Non-Final Office Action Issued in U.S. Appl. No. 18/113,297, mailed May 14, 2024, 41 pages.

(56) References Cited

OTHER PUBLICATIONS

Office Action Issued in U.S. Appl. No. 18/113,297, mailed Aug. 27, 2024, 54 pages.
International Search Report and Written Opinion for PCT/US2020/060565, mailed Mar. 8, 2021, 11 pages.
International Search Report and Written Opinion for PCT/US2021/051803, mailed Jan. 12, 2022, 6 pages.
International Search Report and Written Opinion for PCT/US2021/062676, mailed Apr. 1, 2022, 9 pages.
International Search Report and Written Opinion for PCT/US2021/063608, mailed Apr. 12, 2022, 11 pages.
International Search Report and Written Opinion for PCT/US2022/012151, mailed Apr. 29, 2022, 9 pages.
International Search Report for PCT/US2021/032600, mailed Sep. 3, 2021, 4 pages.
Non-Final Office Action Issued in U.S. Appl. No. 16/840,270, Mailed Sep. 21, 2021, 58 pages.
Notice of Allowance mailed Jan. 4, 2022, for "Cryogenic Vial", U.S. Appl. No. 29/748,815, 9 pages.
Notice of Reasons for Refusal for Japanese Patent Application No. 2021-518707, mailed May 11, 2022, 11 pages.
Office Action dated Sep. 3, 2020, for U.S. Appl. No. 16/840,718, 46 pages.
OXO Airtight Pet Food Storage POP Container. Online published date unknown. Retrieved on May 24, 2022 from URL: https://www.walmart.com/ip/oxo-pet-food-storage-pop-container/623284606, 1 page.
Maggiulli, Roberta, et al., "Implementing an electronic witnessing system into a busy IVF clinic—one clinic's experience", Genera Center for Reproductive Medicine, Rome, Italy, 2 pages.
Rienzi, Laura , et al., Poster Witness "Electronic Witness System makes patients less concerned about biological sample mix-up errors and comfortable with IOVF clinical practice", Genera Center for Reproductive Medicine, Via de Notaris 2b, 00197, Rome, Italy. 2015, 1 page.
Swedberg, Claire , "Hitachi Chemical Markets Tiny UHF Tag", https://www.rfidjournal.com/hitachi-chemical-markets-tiny-uhf-tag, Sep. 12, 2010, 4 pages.
Thornhill, A. R, et al., Measuring human error in the IVF laboratory using an electronic witnessing system, Monduzzi Editoriale, Proceedings, 17th World Congress on Controversies in Obstetrics, Genecology & Infertility (GOGI), Nov. 8-11, 2012 Lisbon, Portugal, 6 pages.
Final Office Action mailed Jul. 15, 2024, for U.S. Appl. No. 18/100,977 in 22 pages.
Notice of Allowance for U.S. Appl. No. 17/490,274, mailed Jun. 26, 2024, 13 pages.
Notice of Reasons for Refusal. Japanese Application No. 2023-518185, dated Jun. 17, 2024, 8 pages.
Chinese Notice of Allowance for Application No. 2023-541871 mailed Oct. 8, 2024, 3 pages.
Comiso, S. et al., "Biot cryocarrier-standardized cryogenic temperature handling of biospecimens"; Biopreservation and Biobanking 13.3: A15. Mary Ann Liebert Inc. (Jun. 2015) (Year: 2015).
Non Final Office Action for U.S. Appl. No. 18/487,878, mailed Sep. 16, 2024, 25 pages.
Thermo Fisher Scientific Introduces System to Double Cryogenic Storage Capacity; M2 Presswire Oct. 27, 2011: NA (Year: 2011).
Zachman, "High-Resolution Studies of Intact Solid-Liquid Interfaces and Reactive Materials by Cryogenic Electron Microscopy"; Cornell University. ProQuest Dissertations & Theses, 2018. 10845397. (Year: 2018).
EP Search Report mailed Nov. 7, 2023, in EP App No. 21808453.1, Nov. 11, 2023.
Japanese Office Action for Japanese Patent Application No. 2022-525678, mailed Oct. 12, 2023 (with English Translation) 12 pages.
Japanese Office Action for JP 2022-569516, mailed Nov. 8, 2023, 6 pages {with English Translation).
Canadian Office Action, for Canadian Application No. 3,202,347 , dated Nov. 7, 2024 4 pages.
European Search Report dated Aug. 7, 2023, for European Application No. 19869478.8, 5 pages.
Fontaine, "Automated Visual Tracking for Behavioral Analysis of Biological Model Organisms," Dissertation (Ph.D.), California Institute of Technology, ProQuest Dissertations Publishing (2008), 156 pages.
International Search Report and Written Opinion for PCT/US2022/077741, mailed date Feb. 1, 2023, 12 pages.
Japanese Office Action for Japanese Patent Application No. 2022-525678, mailed May 29, 2023 (with English Translation) 12 pages.
Japanese Office Action, dated Jun. 6, 2023, for corresponding Japanese Application No. 2022-525679, 16 pages.
Notice of Allowance for U.S. Appl. No. 17/321,174, mailed Jul. 12, 2023, 13 pages.
Notice of Allowance for U.S. Appl. No. 29/847,793, mailed Jul. 27, 2023, 2 pages.
EP Search Report mailed Mar. 6, 2024 in EP App No. 22739992.0, 7 pages.
Non-Final Office Action Issued in U.S. Appl. No. 18/100,977, mailed Jan. 19, 2024, 29 pages.
Canadian Office Action, for Canadian Application No. 3,176,037, dated Apr. 30, 2025, 6 pages.
Chapter 18—Mechanical Fastening, Michael J. Troughton, Handbook of Plastics Joining (Second Edition), William Andrew Publishing, 2009, pp. 175-201, ISBN 9780815515814, https://doi.org/10.1016/978-0-8155-1581-4.50020-2.
Final Office Action for U.S. Appl. No. 17/552,327, mailed May 2, 2025, 23 pages.
Non Final Office Action for U.S. Appl. No. 18/100,977, mailed Jun. 4, 2025, 33 pages.
Notice of Allowance for U.S. Appl. No. 18/130,826 mailed Mar. 2, 2026, 107 pages.
Notice of Allowance for U.S. Appl. No. 17/961,983 mailed Sep. 26, 2025, 9 pages.

* cited by examiner

TRANSFER STATION, INTERROGATION STATION, AND RELATED METHODS TO FACILITATE TRANSFER OF BIOLOGICAL SPECIMENS STORED AT CRYOGENIC CONDITIONS

TECHNICAL FIELD

The present disclosure generally relates to a transfer station, interrogation station, and related methods to transfer biological specimens (e.g., eggs, sperm, embryos, other biological tissue) between a cryogenic freezer (e.g., cryogenic storage tank or liquid nitrogen bath), which is typically fixed or stationary, and a portable thermally insulated carrier or cassette, and to facilitate identification of stored biological specimens and evidence chain-of-custody during handling.

BACKGROUND

Description of the Related Art

Long-term preservation of cells and tissues through cryopreservation has broad impacts in multiple fields including tissue engineering, fertility and reproductive medicine, regenerative medicine, stem cells, blood banking, animal strain preservation, clinical sample storage, transplantation medicine, and in vitro drug testing. This can include the process of vitrification in which a biological specimen or sample (e.g., an oocyte, an embryo, a biopsy) contained in or on a storage device (e.g., a cryopreservation straw, cryopreservation tube, stick or spatula) is rapidly cooled by placing the biological specimen and the storage device in a substance, such as liquid nitrogen.

This results in a glass-like solidification or glassy state of the biological specimen (e.g., a glass structure at the molecular level), which maintains the absence of intracellular and extracellular ice (e.g., reducing cell damage and/or death) and, upon thawing, improves post-thaw cell viability. To ensure viability, the vitrified biological specimens must then be continuously stored in a liquid nitrogen dewar or other container containing the liquid nitrogen, which is at a temperature of negative 190 degrees Celsius.

Each harvested biological specimen is loaded on a rigid specimen holder (e.g., embryo straw, stick or spatula). In the case of a tubular specimen holder, the tube may be closed (e.g., plugged) at one end and open at the other end. The cryopreservation storage devices (e.g., specimen holders) containing or holding the biological specimen are cooled as quickly as possible by plunging the cryopreservation storage device with the biological specimen into a liquid nitrogen bath in a cryogenic freezer at a temperature of approximately negative 190 degrees Celsius, for example to achieve vitrification. More particularly, multiple cryopreservation storage devices are placed in a goblet for placement in the liquid nitrogen storage tank or freezer. The goblet attaches to the liquid nitrogen storage tank such that the multiple cryopreservation storage devices are suspended in the liquid nitrogen.

Labels that are manually written-on using a suitable marker pen or printed using a custom printer are attached to the straw and/or the goblet. Such labels can include identification information corresponding to the individual that the embryo was harvested from and other suitable information (e.g., a cryopreservation storage device number, a practitioner number, etc.).

Access to the biological specimens is required during normal operation. For example, a particular biological specimen or specimens may be required to perform a procedure (e.g., implantation of a fertilized egg). Retrieval of cryopreservation storage devices and associated biological specimens from the cryogenic refrigerator or cryogenic tank in which the biological specimens are stored exposes the retrieved biological specimens to non-cryogenic conditions (e.g., temperatures above negative 190° C.), and depending on a duration of the exposure places the biological specimens at risk.

Due to the way biological specimens are stored (e.g., cryopreservation storage devices arrayed in cassettes, cassettes arrayed in stacks), retrieval of one or more desired biological specimens often requires retrieval of additional biological specimens that are not needed at that time, exposing such to risk. Additionally, transport of biological specimens from a cryogenic refrigerator to a site (i.e., worksite or work station) of an intended use (e.g., fertilization, implantation) exposes the biological specimens to risk.

Thus, there are a number of concerns in how biological specimens are being stored, identified, managed, inventoried, retrieved, etc. With regard to storage and management of these biological specimens, facilities employ personnel that are required to maintain the liquid nitrogen storage tanks (e.g., by refilling them with liquid nitrogen when needed) and manage the inventory of stored biological specimens (e.g., by performing periodic accountings). There is, however, little recordkeeping with regard to the proper storage of these biological specimens. For example, subsequent identification or otherwise handling of the vitrified biological specimen or sample can involve removal of the specimen from temperature-controlled storage and exposure of the sample to ambient temperature, thus potentially risking the viability of the sample.

BRIEF SUMMARY

Accordingly, it is desirable to provide new transfer stations, interrogation stations, and related methods for transferring biological specimens (e.g., eggs, sperm, embryos) between a cryogenic freezer, which is typically a large, heavy piece of equipment that is often stationary, and a portable, thermally insulated, carrier, for example for eventual transport to a worksite or workstation at which work will be performed (fertilization, implantation). It is also desirable to provide new transfer stations, interrogation stations, and related methods to facilitate identification of stored biological specimens or samples and evidence chain-of-custody during transfer to and from relatively long term (e.g., days, months, years) cryogenic storage.

An interrogation station facilitates transfer of specimen containers (e.g., vials with caps) into and out of a cryogenic freezer (also known as a dewar). A plurality of the specimen containers may be carried by a storage cassette, which may be designed to be stored in the cryogenic freezer, or in a specimen transporter, which is designed to carry the specimen containers from one location to another while maintaining the viability of the biological specimen within the specimen containers (e.g., by maintaining a cryogenic environment within the specimen transporter that surrounds the specimen containers).

Both the storage cassette and the specimen transporter may be positioned at the interrogation station while one or more of the specimen containers are transferred from one of the storage cassette and the specimen transporter to the other of the storage cassette and the specimen transporter. Identification information is read from wireless transponders carried by the specimen containers, and optionally carried by the storage cassette and the specimen transporter. Inventories of specimen containers and even specific specimen holders may be maintained, as or with proof of chain of custody. Automated storage and retrieval may be provided, for instance via robotic appendages and/or conveyors.

The interrogation station may include a frame and a well, and an array of antennas positioned beneath a bottom of the well, spaced at a nominal distance, within a defined tolerance, from the bottom of the well, and laterally aligned with opening in the frame that provide access to the well. The opening(s) of the frame and/or well may be sized to removably receive buckets, the buckets defining reservoirs, for example to hold carriers of specimen containers and/or cryogenic fluid. The frame and/or well may include one or more features (e.g., spacing features and/or registration features), which physically engage complementary features (e.g., spacing features and/or registration features) on the buckets, to position the buckets with respect to the bottom of the well in a vertical direction as well as laterally, thereby vertically spacing and laterally aligning the bucket with the antennas of the array of antennas. Each bucket includes one or more features (e.g., spacing features and/or registration features) which physically engage complementary features (e.g., spacing features and/or registration features) on the carriers (e.g., bulk carriers), to position the carriers with respect to the buckets in a vertical direction as well as laterally, thereby vertically spacing and laterally aligning the carriers with the antennas of the array of antennas. Each carrier includes a cassette with an array of through holes, sized to hold respective specimen containers at fixed locations in the carrier. Each carrier includes one or more features (e.g., spacing features and/or registration features) which physically engage complementary features (e.g., spacing features and/or registration features) on the cassette (e.g., bulk carriers), to position the cassettes with respect to the carriers in a vertical direction as well as laterally, thereby vertically spacing and laterally aligning the cassettes and specimen containers with their attached RFID transponders with the antennas of the array of antennas of the RFID interrogator.

The well may, for example, advantageously provide a thermal barrier (e.g., air gap) between a cryogenic fluid (e.g., liquid nitrogen) and a circuit board and/or electronics of the RFID interrogator, providing thermal protection to the circuit board and/or electronics. The well may optionally safely collect any cryogenic fluid that may spill, for example from buckets or carriers, into the well.

The interrogation station may be formed or provided as an integral unit (e.g., drop in unit), which can be installed in an opening in a transfer surface of any instances of a transfer station, for example where the instances of the transfer station are of a same make and model as one another, or where the instances of the transfer station are of different makes and/or models from one another. As explained herein, the interrogation stations inherently positions antennas of an interrogator (e.g., RFID interrogator) to be laterally aligned with respective locations at which transponders on specimen containers will be positioned and at nominal perpendicular distances, within a specified tolerance, from those locations. This advantageously allows transfer stations to be easily outfitted with interrogation stations or updated interrogation stations, without requiring expensive and painstaking efforts to align and space the antennas relative to the transfer surface of the transfer station.

BRIEF DESCRIPTION OF THE DRAWINGS

In the drawings, identical reference numbers identify similar elements or acts. The sizes and relative positions of elements in the drawings are not necessarily drawn to scale. For example, the shapes of various elements and angles are not drawn to scale, and some of these elements are arbitrarily enlarged and positioned to improve drawing legibility. Further, the particular shapes of the elements as drawn are not intended to convey any information regarding the actual shape of the particular elements, and have been solely selected for ease of recognition in the drawings.

DETAILED DESCRIPTION

In the following description, certain specific details are set forth in order to provide a thorough understanding of various disclosed embodiments. However, one skilled in the relevant art will recognize that embodiments may be practiced without one or more of these specific details, or with other methods, components, materials, etc. In other instances, well-known structures associated with computer systems, actuator systems, and/or communications networks have not been shown or described in detail to avoid unnecessarily obscuring descriptions of the embodiments.

Unless the context requires otherwise, throughout the specification and claims which follow, the word "comprise" and variations thereof, such as, "comprises" and "comprising" are to be construed in an open, inclusive sense, that is as "including, but not limited to."

Reference throughout this specification to "one implementation" or "an implementation" or to "one embodiment" or "an embodiment" means that a particular feature, structure or characteristic described in connection with the implementation or embodiment is included in at least one implementation of embodiment. Thus, the appearances of the phrases "in one implementation" or "in an implementation" or "in one embodiment" or "in an embodiment" in various places throughout this specification are not necessarily all referring to the same implementation or embodiment. Furthermore, the particular features, structures, or characteristics may be combined in any suitable manner in one or more implementations or embodiments.

As used in this specification and the appended claims, the singular forms "a," "an," and "the" include plural referents unless the content clearly dictates otherwise. It should also be noted that the term "or" is generally employed in its sense including "and/or" unless the content clearly dictates otherwise.

The headings and Abstract of the Disclosure provided herein are for convenience only and do not interpret the scope or meaning of the embodiments.

Figure 1:
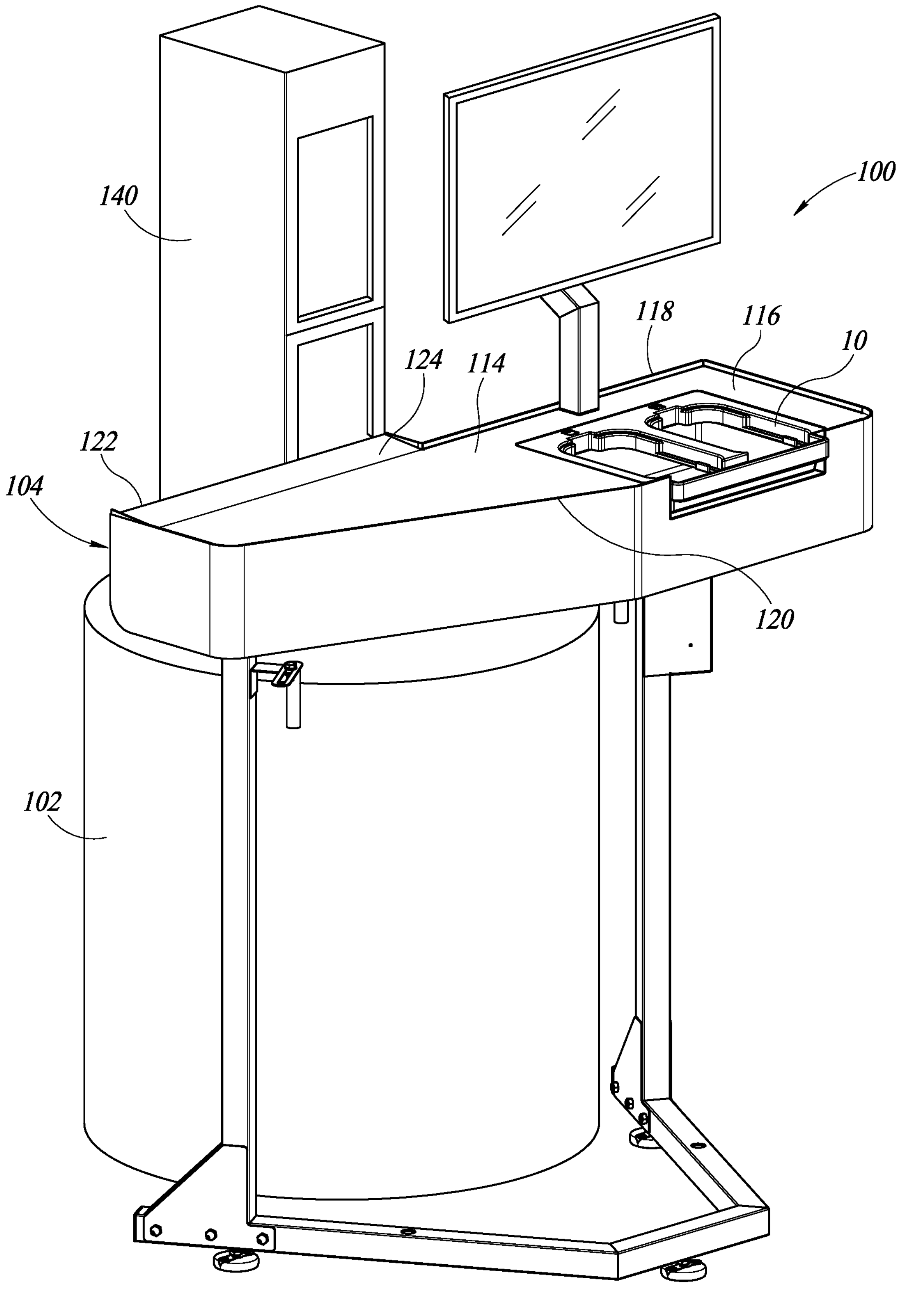
FIG. 1 is a front, top, isometric view of a cryogenic storage system including a cryogenic storage tank that holds a coolant, a robotic transfer system operable to transfer biological specimen into and out of the cryogenic storage tank, and a transfer station including an interrogation station to handle and track the transfer of biological specimens into and out of the cryogenic freezer and to maintain a chain of custody for the biological specimens, according to at least one illustrated embodiment.
Figure 2:
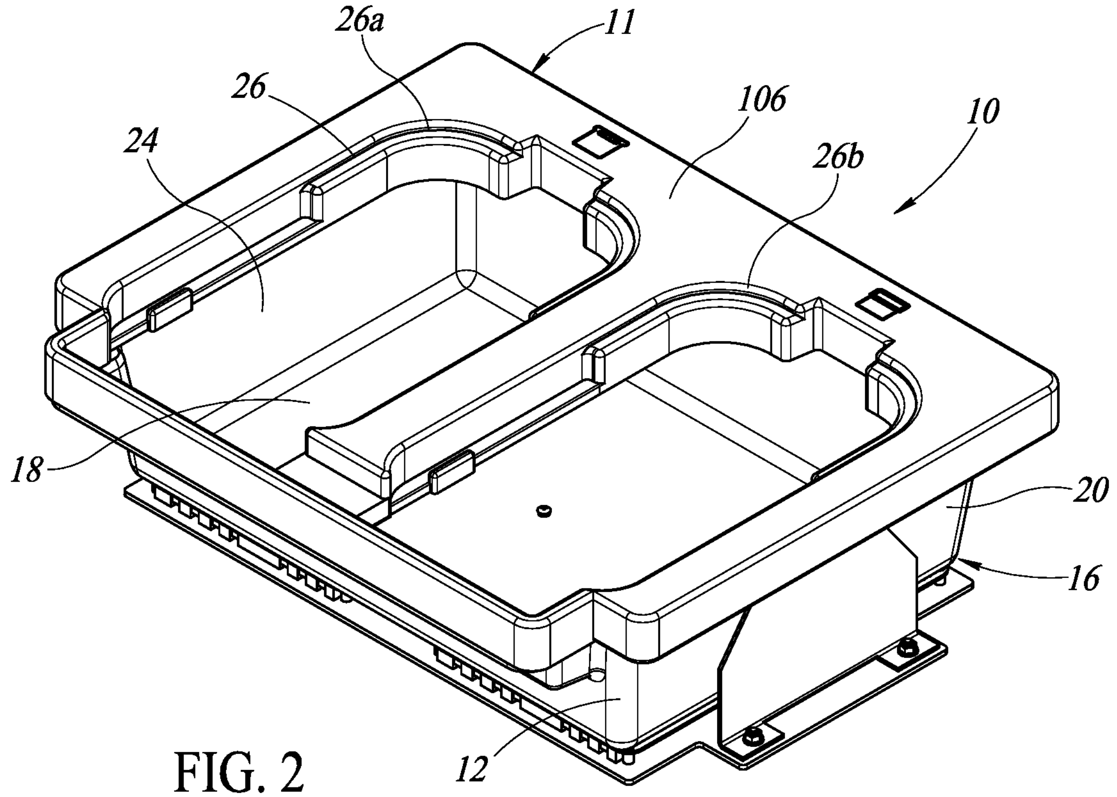
FIG. 2 is a top, isometric view of the interrogation station illustrated in FIG. 1, according to one embodiment.
Figure 3:
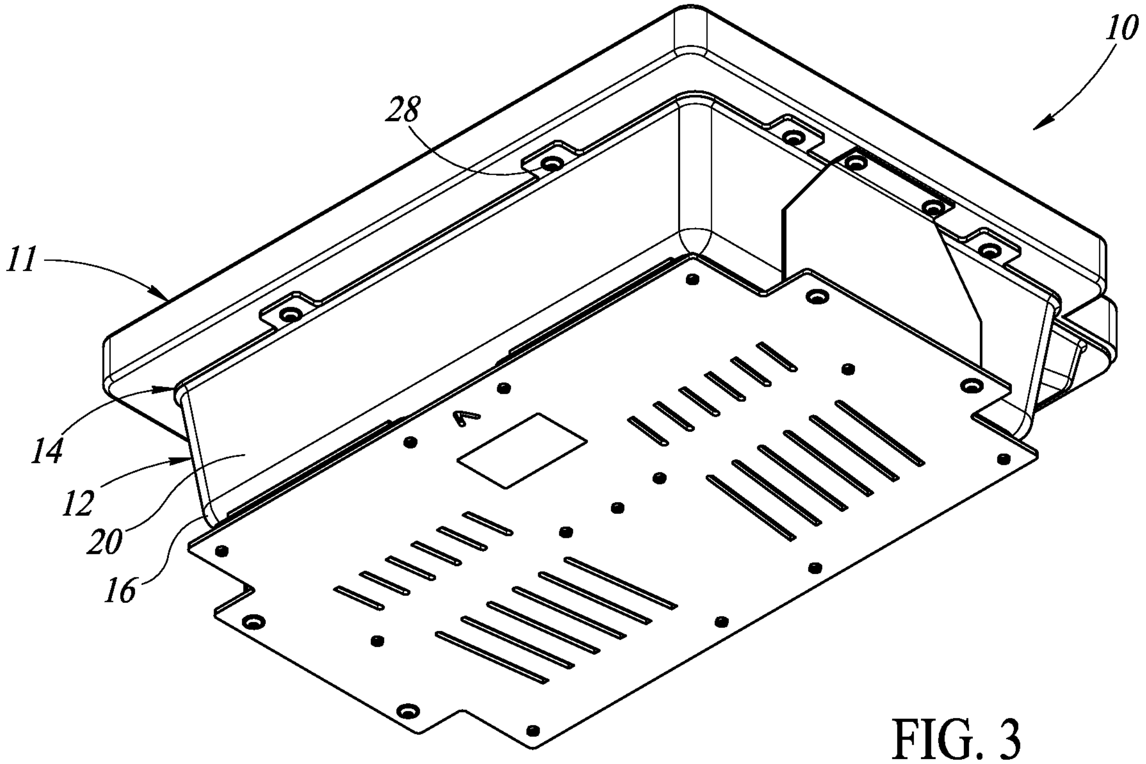
FIG. 3 is a bottom, isometric view of the interrogation station illustrated in FIG. 2.
Figure 4:
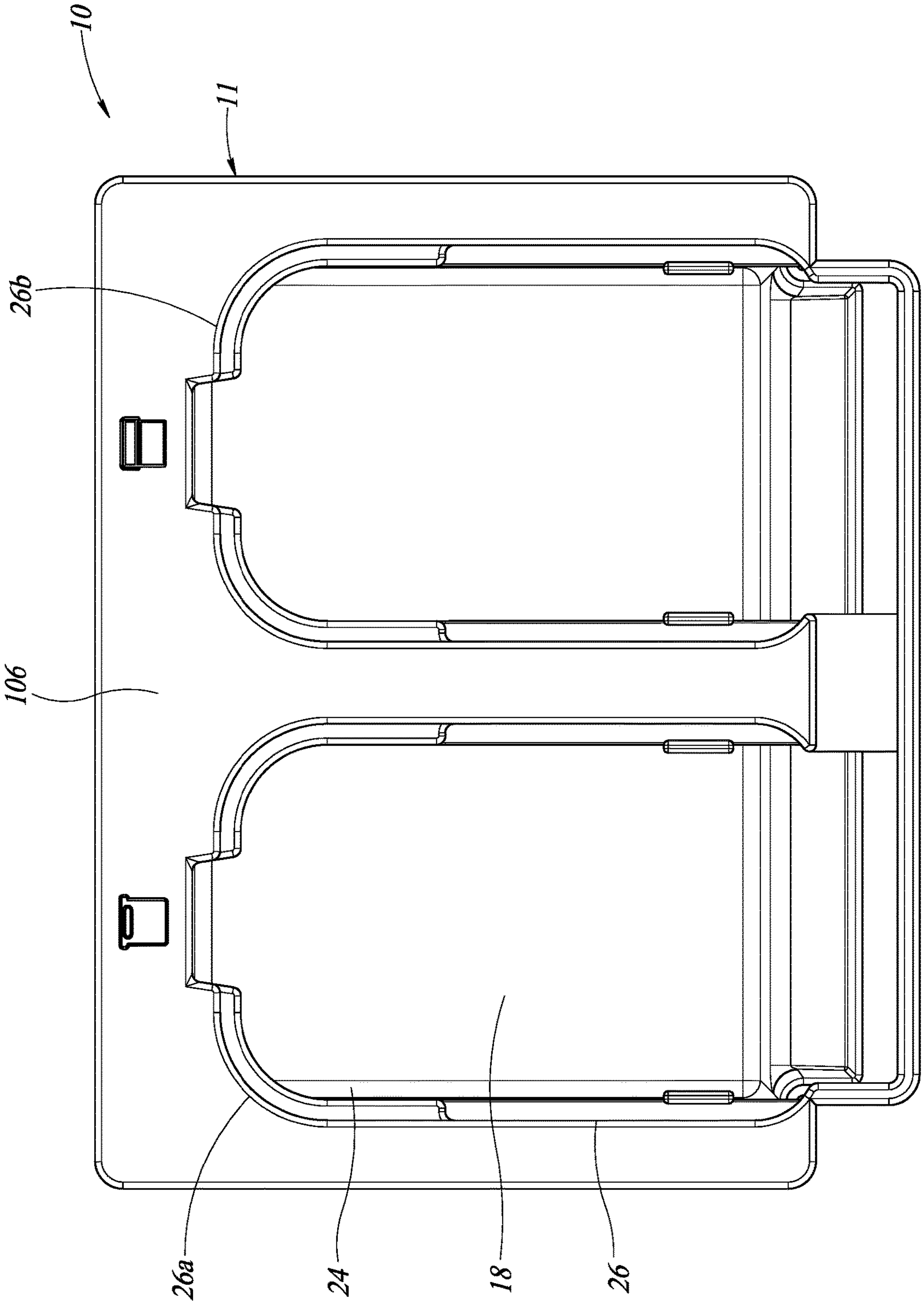
FIG. 4 is a top, plan view of the interrogation station illustrated in FIG. 2.

Referring to FIG. 1, a cryogenic storage system 100 may take a large variety of forms, typically including cryogenic freezer 102 which can store specimen containers in a cryogenic environment, for example immersed in a bath of liquid nitrogen at a temperature at or below about negative 190° C. The cryogenic freezer 102 is typically highly thermally insulated, and may include stainless steel interior and exterior walls with a vacuum and/or other thermal insulating material therebetween.

The cryogenic storage system 100 may include a transfer station 104 to facilitate the transfer of biological specimen to and from the cryogenic freezer 102, including identification of said transferred biological specimen and evidence chain-of-custody during handling of said stored biological specimen. According to one implementation, the transfer station 104 may be located adjacent, for example immediately adjacent, the cryogenic freezer 102. The transfer station 104 may include a transfer surface 114 having a planar portion 116 and a peripheral wall 118 that extends upwardly from the planar portion 116 about at least a portion of a periphery 120 of the transfer surface 114. The transfer station 104 may include an interrogation station 10 that facilitates the transfer of biological specimen from one container to another container. The interrogation station 10 may, for example, be at least partially recessed into the transfer surface 114, allowing cold (e.g., liquid nitrogen bath) temporary holding of biological specimens while outside of the cryogenic freezer 102, for example during transfer operations (e.g., retrieval from and/or placement in cryogenic freezer 102). The transfer station 104 may include an elevated floor, which facilitates a shorter distance to a top of the cryogenic freezer 102 for a user standing on the elevated floor as opposed to standing on a non-elevated floor (e.g. the floor upon which the cryogenic freezer 102 rests).

Referring to FIGS. 2 to 12, the cryogenic storage system 100 may include an interrogation station 10 that facilitates the transfer of biological specimen from one container to another container. The interrogation station 10 may maintain a suitable temperature for the biological specimen during the transfer process. Additionally, the interrogation station 10 may identify and track each biological specimen during the transfer process. The interrogation station 10 may be formed or provided as an integral unit (e.g., drop in unit), which can be installed in an opening in a transfer surface 114 of any instances of a transfer station 104, for example where the instances of the transfer station 104 are of a same make and model as one another, or where the instances of the transfer station 104 are of different makes and/or models from one another. As explained herein, the interrogation stations 10 inherently positions antennas of an interrogator (e.g., RFID interrogator) to be laterally aligned with respective locations at which transponders on specimen containers will be positioned and at nominal perpendicular distances, within a specified tolerance, from those locations. This advantageously allows transfer stations 104 to be easily outfitted with interrogation stations 10 or updated interrogation stations 10, without requiring expensive and painstaking efforts to align and space the antennas relative to the transfer surface 114 of the transfer station 104.

Referring to FIGS. 2 to 7, the interrogation station 10 may include a frame 11 and a well 12 (one illustrated). The well 12 may include an upper portion 14 and a lower portion 16. The lower portion 16 may include a bottom 18 and at least one sidewall 20 that extends upwardly from the bottom 18.

The upper portion 14 of the well 12 may include an open top 22, wherein the bottom 18, the at least one sidewall 20, and the top 22 cooperatively delineate an interior cavity 24 of the well 12.

The frame 11 may include at least one opening 26*a,* 26*b* (two shown) extending through an upper surface 106 of the frame to the open top 22 of the well 12 so as to provide entry and access to the interior cavity 24. As illustrated, the frame 11 include a first opening 26*a* and a second opening 26*b*. The first opening 26*a* and the second opening 26*b* may be identical in size and shape, as shown in the illustrated embodiment. Alternatively, the first opening 26*a* and the second opening 26*b* may have a different size, shape, or both size and shape. As explained herein, the well 12 and the openings 26*a,* 26*b* of the frame 11 are sized to removably receive and hold buckets, which in turn hold carriers (e.g., bulk carriers) which may be immersed or partially immersed in a coolant (e.g., nitrogen in liquid and/or vapor form). The well 12 may, for example, advantageously provide a thermal barrier (e.g., air gap) between a cryogenic fluid (e.g., liquid nitrogen) and a circuit board and electronics, and optionally safely collect any cryogenic fluid that may spill, for example from buckets or carriers, into the well 12.

The frame 11 and the well 12 may be manufactured as two or more separate structures that are joined together (e.g., by one or more fasteners 28). Alternatively, the frame 11 and the well 12 may be formed as one monolithic piece. The well 12 may comprise, or even consist of, a material with a wide operating temperature range, that is resistant to damage caused by exposure to repeated temperature changes (e.g., caused by intermittent exposure or proximity to coolant, for example cryogenic fluids such as liquid nitrogen, and associated cold temperatures). The material of the well 12 may also be precisely machinable with adherence to tight tolerances. According to at least one implementation, the well 12 is made from an engineering thermoplastic, such as polyoxymethylene (also known as Delrin).

Referring to FIGS. 5 to 10, the interrogation station 10 may further include at least one sensor capable of identifying individual specimen containers. According to at least one implementation, the at least one sensor includes an RFID reader 30 (also known as an interrogator, called out in FIGS. 7-10), including for example one or more RFID reader integrated circuits 31 (illustrated in broken line in FIG. 9) and antennas 34 (one called out in FIGS. 8 and 10), for instance carried by one or more printed circuit boards 32. The RFID reader 30 may optionally also include one or more processors, for example, one or more of: one or more microcontrollers, one or more microprocessors, one or more central processing units, one or more digital signal processors (DSPs), one or more graphics processing units (GPUs), one or more application specific integrated circuits (ASICs), one or more field programmable gate arrays (FPGAs), and/or one or more programmable logic controllers (PLCs). The RFID reader 30 may each include one or more non-transitory storage media, for example, one or more nonvolatile storage media and/or one or more volatile storage media, for example one or more of: one or more read only memories (ROMs), one or more random access memories (RAMs), one or more FLASH memory, one or more magnetic disk drives, one or more optical disk drives, one or more solid state drives, one or more cache memories, and/or one or more registers of one or more processors.

As shown, the interrogation station 10 may include at least one printed circuit board 32 (e.g., mounted beneath the well 12 as described in greater detail below). The RFID reader 30 may include at least one antenna 34 positioned beneath the well 12 (e.g., mounted to an upper side 36 of the printed circuit board 32). According to at least one implementation, the RFID reader 30 may include at least one array 38 of the antennas 34 and at least one RFID interrogation circuit or radio (e.g., integrated circuit RFID readers 1400*a*-1400*j*), for example mounted to or otherwise carried by the printed circuit board 32.

As shown, the at least one array 38 of the antennas 34 may include a two-dimensional array of, for example, coil antennas, and the two-dimensional array may include, for example, up to a nine-by-nine (9×9) array of the antennas 34. Optionally, the antennas 34 may be arranged as one-dimensional arrays.

Figure 13:
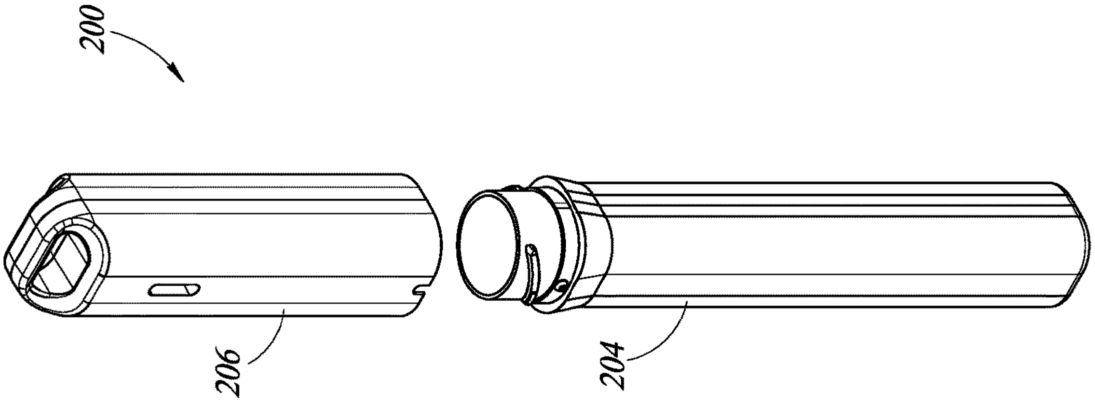
FIG. 13 is an exploded view of the specimen container illustrated in FIG. 11.
Figure 12:
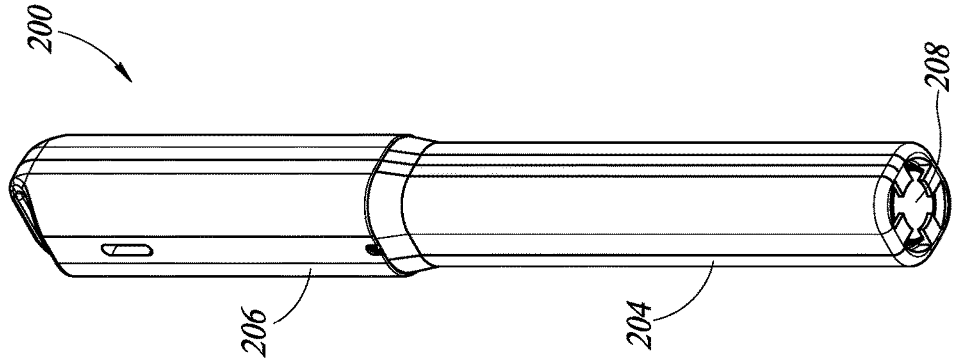
FIG. 12 is a bottom, isometric view of the specimen container illustrated in FIG. 11.
Figure 11:
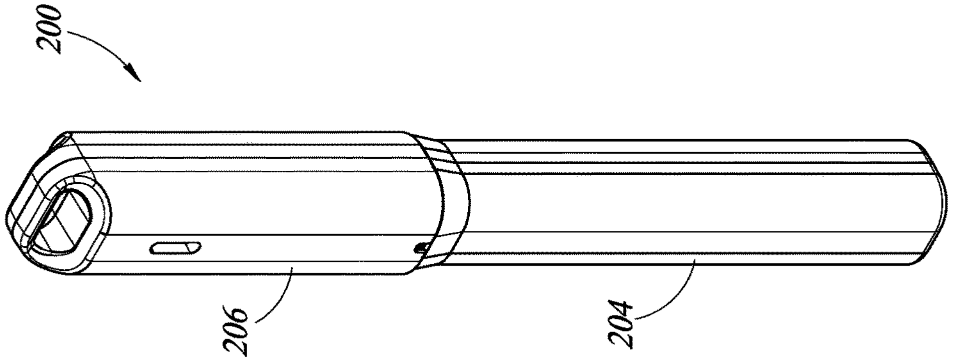
FIG. 11 is a top, isometric view of a specimen container, according to one embodiment.

The RFID reader 30 may perform wireless interrogation of wireless transponders, (e.g., passive radio frequency identification (RFID) transponders) used to tag respective specimen containers (e.g., the specimen containers 200 shown and described in reference to FIGS. 11 to 13 below). The RFID reader 30 may individually identify the specimen containers 200 via unique identifiers stored by wireless transponders, and locate a respective position of the specimen containers 200 in an arrangement of the specimen containers 200.

As shown, the interrogation station 10 may include a first two-dimensional array 38*a* of the antennas 34 and a second two-dimensional array 38*b* of the antennas 34. The interrogation station 10 may include a first printed circuit board 32*a* that carries the first two-dimensional array 38*a* and a second printed circuit board 32*b* that carries the second two-dimensional array 38*b*. By virtue of the layout of the first and second arrays of antennas 38*a,* 38*b* and the alignment features of the components of the interrogation station 10 (described in detail below), each of the antennas 34 is positioned to align with a respective position in which a respective wireless transponder of a specimen container 200 may be located when the interrogation station 10 is used as described below. The RFID reader 30 may include at least one radio (e.g., integrated circuit RFID readers 1400*a*-1400*j* illustrated in FIG. 25) that causes transmission of interrogation signals via the antennas 34 and which may decode unique identifiers from response signals returned by the wireless transponders in response to the interrogation signals.

Figure 5:
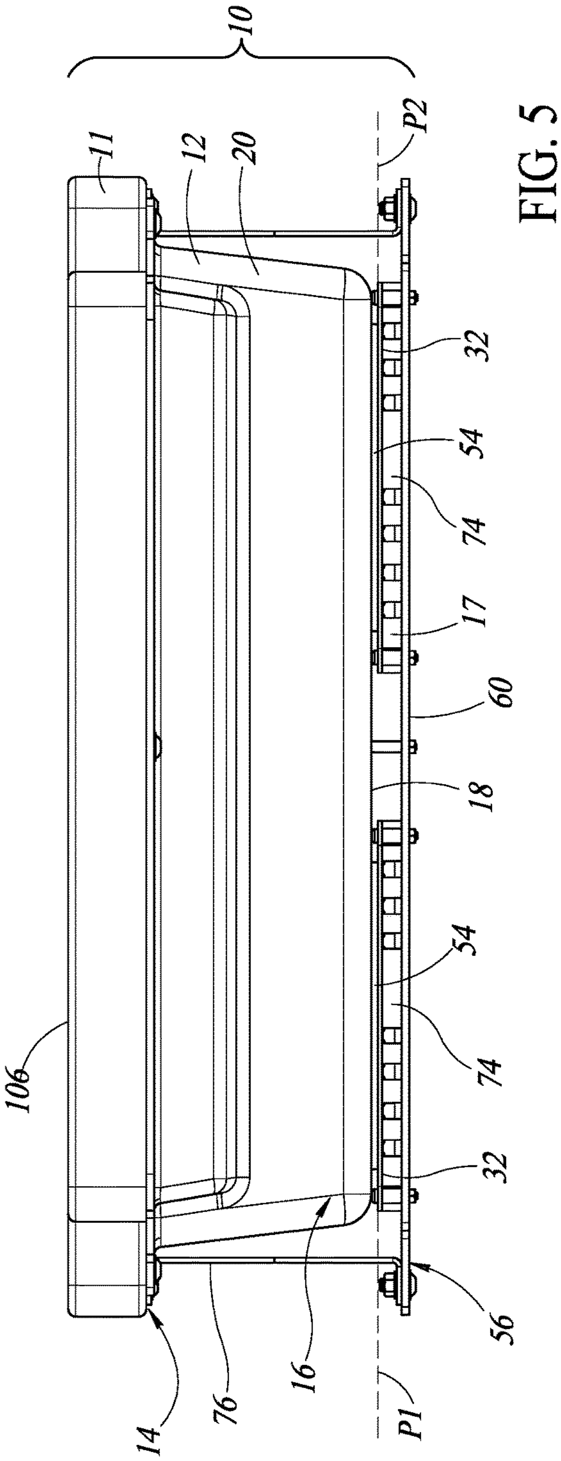
FIG. 5 is a front, elevation view of the interrogation station illustrated in FIG. 2.
Figure 6:
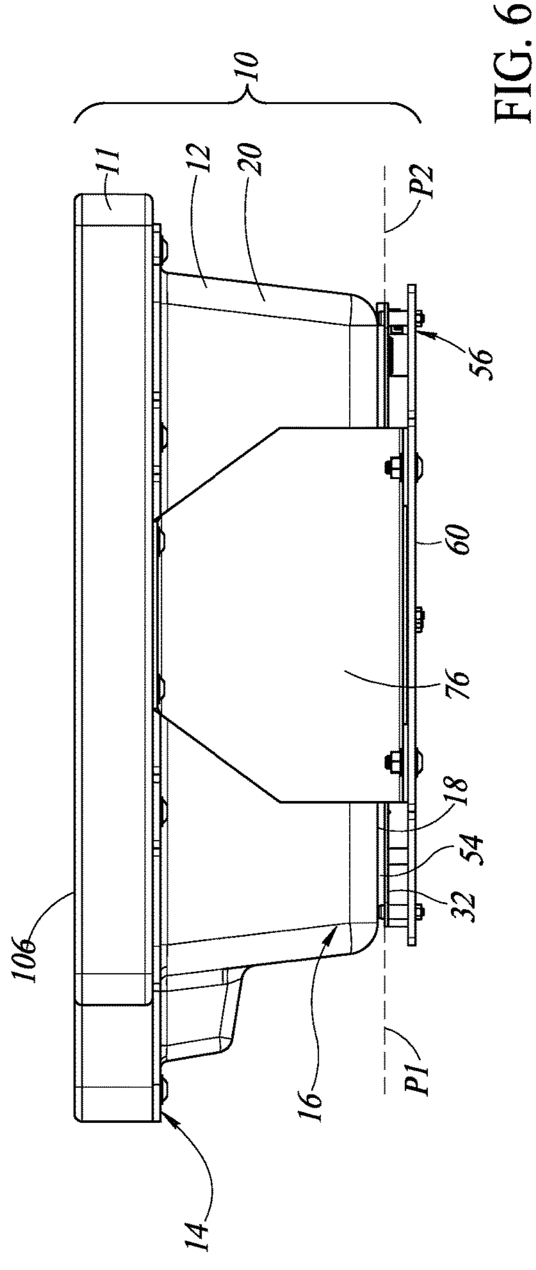
FIG. 6 is a side, elevation view of the interrogation station illustrated in FIG. 2.
Figure 7:
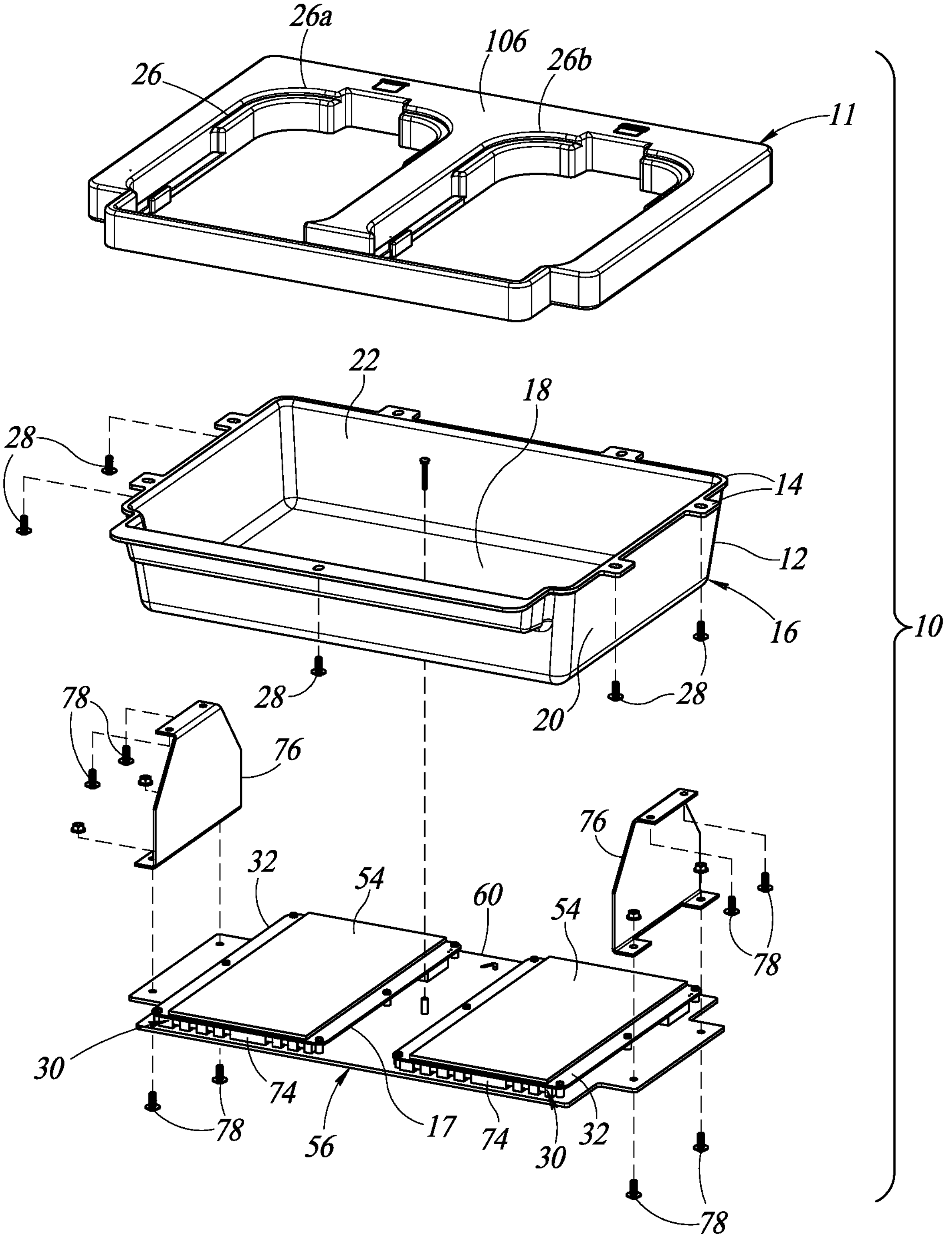
FIG. 7 is a partially exploded, isometric view of the interrogation station illustrated in FIG. 2.

As shown in FIGS. 5 and 6, the printed circuit board 32 may be mounted beneath the well 12 such that at least a portion of the printed circuit board 32 is accessible from the surrounding environment, (i.e., not enclosed within an enclosure). Accessibility to the surrounding environment may result in increased cooling of the printed circuit board 32 and their associated electronic components, which tend to heat up during operation. Thus, while it may seem beneficial to enclose the printed circuit board 32 to isolate the printed circuit board 32 from the moisture and cold temperatures resultant from coolant (e.g., cryogenic fluid) supported by the well 12 within close proximity to the printed circuit board 32, the excess heat generated within the enclosure may instead have a detrimental effect. Additionally, the proximity of the enclosure to the extreme low temperature resultant from the coolant (e.g., cryogenic fluid) can result in increased moisture formation within the enclosure as opposed to an open support frame. Further, enclosing the printed circuit board 32 can subject the printed circuit board 32, the electrical and electronic components carried thereby, and various electrical connections (e.g., solder) therebetween, to more extreme thermally cycling, increasing the risk of delamination of the printed circuit board 32, failure of one or more components and/or electrical connections.

Alternatively, according to at least one implementation, the interrogation station 10 may include an enclosure that receives the printed circuit board 32 carrying the at least one array 38 of antennas 34. Active and/or passive cooling (e.g., fans, vents, etc.) may be provided to remove heat from the enclosure generated by operation of components of the printed circuit board 32.

The printed circuit board 32 may include additional components such as batteries, resistors, LEDs, transistors, capacitors, etc. that enable functionality of the RFID reader 30. As certain components of the RFID reader 30 are susceptible to temperature, moisture or both, the interrogation station 10 may include features that protect those susceptible components, as they are operating in close proximity to the coolant, which tends to generate extreme temperatures and excess moisture in its proximity.

According to at least one implementation, the printed circuit board 32 may be treated to provide increased resistance to damage due to exposure to extremely cold temperatures. The printed circuit board 32 may be treated with a parylene vapor deposition process, and then dipped in polyurethane to prevent delamination.

According to at least one implementation, the interrogation station 10 includes an insulator 54. The insulator 54 may be positioned between the printed circuit board 32 and the well 12. As shown, the insulator 54 may directly contact both the printed circuit board 32 and the well 12. The insulator 54 may be secured (e.g., by an adhesive, a fastener, etc.) relative to one or both of the printed circuit board 32 and the bucket housing 12. Alternatively, the insulator 54 may be held in place by a friction fit with both of the printed circuit board 32 and the well 12.

The insulator 54 may be deformable (e.g., a foam or a foam-like material) such that pressure applied to the insulator 54 towards the printed circuit board 32 causes the insulator 54 to deform and partially surround components on the upper side 36 of the printed circuit board 32, (e.g., the antennas 34). The insulator 54 may thereby protect the antennas 34 from exposure to extremely low temperatures, resultant from the proximity of the coolant, that may otherwise affect the performance and/or the functionality of the antennas 34. The insulator 54 may include a hydrophobic material to repel moisture from the partially surrounded components. According to one embodiment, the insulator 54 includes an aerogel. Note that in FIG. 8, the insulator 54 (including two separate portions), is shown in dashed lines and as being transparent to allow visibility of the antennas 34.

Proper alignment of the antennas 34 and the well 12 is important for accurate identification of specimen being transferred with the aid of the interrogation station 10. Accordingly, the interrogation station 10 may include a coupler 56 that secures the printed circuit board 32 relative to the well 12. As shown the coupler 56 may secure the printed circuit board 32 relative to the well 12 such that the array 38 of the antennas 34 are laterally aligned with the opening 26 in the frame 11 and the open top 22 of the well 12, as well as being spaced perpendicularly or vertically from the bottom of the well 12 by a nominal distance (e.g., 5 mm) within a specified tolerance (e.g., +/−10%).

According to at least one implementation, the array 38 of the antennas 34 may be located within a plane P1. The coupler 56 secures the printed circuit board 32 relative to the well 12 and the frame 11. For example, the coupler secures the printed circuit board 32 to longitudinally position the array 38 of the antennas 34 at a defined nominal distance (e.g., 5 mm) within a specified tolerance (e.g., +/−10%) of the bottom of the well 12 along a direction normal to the plane P1 (e.g., a vertical direction indicated by arrow J). Also for example, the coupler secures the printed circuit board 32 to laterally position the array 38 of the antennas 34 laterally aligned or in registration with the opening(s) 26 in the frame 11 and the open top 22 of the well 12, for instance along a first lateral direction and a second lateral direction, the first and second lateral directions perpendicular to the vertical direction and also perpendicular to one another.

According to at least one implementation, the antennas 34 within the array 38 each include a respective beam axis 58, and the coupler 56 secures the printed circuit board 32 relative to the well 12 such that the beam axes 58 of the antennas 34 in the array 38 are respectively laterally aligned with a respective location at which an antenna of an RFID transponder attached to a vial will be located when a bulk carrier is positioned in a bucket in the opening of the frame 11 and in the well 12. The beam axis 58 may include an axis of maximum radiation (e.g., the axis passing through the center of the main lobe of the radiation plot of the antenna). According to at least one implementation, the antenna 34 may be a coil antenna or a helical antenna and the beam axis 58 may be collinear with a central axis of the coil antenna or the helical antenna.

As shown in the illustrated implementation, the coupler 56 may include a plate 60 that supports the printed circuit board 32. According to one embodiment, the plate 60 supports the printed circuit board 32 such that there is a standoff 17, or gap, between the plate 60 and the printed circuit board 32. The standoff 17 may be sized to provide adequate space for components of the printed circuit board 32 mounted on a lower side 62 of the printed circuit board 32 (the lower side 62 being opposite the upper side 36). Fasteners 64 with a spacer 66 may be used to secure the plate 60 to the printed circuit board 32, with the spacer 66 being positioned between the plate 60 and the printed circuit board 32, such that a height of the spacer 66 sets a height of the standoff 17. According to at least one implementation, the height of the standoff 17 between the plate 60 and the printed circuit board 32 is between 5 mm and 15 mm, for example 8 mm.

According to at least one implementation, the plate 60 may be thin (e.g., having a thickness less than the standoff 17, or having a thickness similar to that of the printed circuit board 32. The plate 60 may be stiff (e.g., stiffer than the printed circuit board 32) such that the plate 60 provides additional strength to the printed circuit board 32 when the printed circuit board 32 is secured to the plate 60. The plate 60 may be transparent so that the components of the printed circuit board 32 that are mounted to the lower side 62 of the printed circuit board 32 are visible through the plate 60. The components of the printed circuit board 32 may include lights or other indicators, and the plate 60 being transparent allows the lights or indicators to be viewed without disconnecting the plate 60 from the printed circuit board 32.

The plate 60 may include through holes 68 extending through the thickness of the plate 60. Some of the through holes 68 may receive respective ones of the fastener 64 used to secure the plate 60 to the printed circuit board 32. These fastener through holes 70 may be circular, as shown in the illustrated embodiment. Others of the through holes 68 may provide access through the plate 60 to the standoff 17. These other through holes (hereinafter vent through holes 72) may act as vents that provide a path for heat generated by the components of the lower side 62 of the printed circuit board 32 to exit the standoff 17. The vent through holes 72 may have various shapes, (e.g., slots as shown in the illustrated implementation).

Different ones of the vent through holes 72 may have different shapes and sizes, and the vent through holes 72 may be positioned to align with certain components of the printed circuit board 32 that produce more heat (e.g., resistors, power supplies or converters, integrated circuit RFID readers or radios). Further, the vent through holes 72 may be positioned so as to be out of alignment with certain components of the printed circuit board 32 that are susceptible to moisture. Note that in FIG. 9 the plate 60 is shown in dashed lines and as being transparent to allow visibility of the underlying components of the circuit board 32.

According to one embodiment, the interrogation station 10 may include a hydrophobic material 74 positioned between one or more portions of the lower side 62 of the printed circuit board 32 and the plate 60. The hydrophobic material 74 may be deformable (e.g., a foam or a foam-like material) with a height slightly greater than that of the standoff 17. Thus, when securing the printed circuit board 32 to the plate 60 the hydrophobic material 74 may be compressed and secured between the printed circuit board 32 and the plate 60 via a friction fit. According to one embodiment, the height of the hydrophobic material 74 is greater than the height of the insulator 54. Alternatively, other connections (e.g., fasteners, adhesives, etc.) may be used to secure the hydrophobic material 74 within the standoff 17.

The hydrophobic material 74 may be similar to the insulator 54 such that pressure applied to the hydrophobic material 74 towards the printed circuit board 32 causes the hydrophobic material 74 to deform and partially surround components on the lower side 62 of the printed circuit board 32, (e.g., the relays). According to at least one implementation, the hydrophobic material 74 is an aerogel, for instance a silica aerogel wrap, for instance having an 8 mm thickness.

Referring still to FIGS. 5 to 10, the coupler 56 may further include one or more brackets 76 (two shown) that secures the plate 60 relative to the well 12 and frame 11. As shown, the bracket 76 may support the plate 60 such that the antennas 34 on the upper side 36 of the printed circuit board 32 are in close proximity to an outer surface of the bottom 18 of the well 12. According to at least one implementation, the antennas 34 on the upper side 36 of the printed circuit board 32 are less than 10 mm from the outer surface of the bottom 18 of the well 12. According to at least one implementation, the antennas 34 on the upper side 36 of the printed circuit board 32 are less than 5 mm from the outer surface of the bottom 18 of the well 12. According to at least one implementation, the antennas 34 on the upper side 36 of the printed circuit board 32 are no more than the thickness of the insulator 54 from the outer surface of the bottom 18 of the well 12.

Fasteners (e.g., additional ones of the fasteners 64, or fasteners 78 with a different size and/or shape, for instance threaded fasteners including screws, bolts and nuts, or other fasteners including clamps, pins, rivets, nails, etc.) may be used to secure the bracket 76 to the well 12 (e.g., an underside of a flange at the open top 22 of well 12), or alternatively to under the top surface 106 of the frame 11, and to secure the bracket(s) 76 to the plate 60. As shown, the bracket(s) 76 may be secured to the well 12 or frame 11 such that the fasteners 78 are not visible (i.e., the fasteners 78 do not protrude through) an upper surface of the top 22 of the frame 11.

Referring to FIGS. 1 and 11 to 13, the cryogenic storage system 100 may include a specimen container 200, which is typically stored for long term storage in a cryogenic environment (e.g., inside the cryogenic freezer 102). Each of the specimen containers 200 may include a vial 204, a cap 206, one or more wireless transponders (e.g., radio frequency identification (RFID) transponders) 208, and an elongated specimen holder (e.g., straw, rod, spatula). Additionally, the specimen containers 200 may include one or more machine-readable symbols. The specimen containers 200, according to one example, may store specimens of biological tissue, for instance eggs, sperm or embryos. Various implementations of specimen containers are described in U.S. patent application 62/900,281, filed Sep. 13, 2019; U.S. patent application 62/880,786, filed Jul. 31, 2019; U.S. patent application 62/879,160, filed Jul. 26, 2019; U.S. patent application 62/741,986, filed Oct. 5, 2018; and U.S. patent application 62/741,998, filed Oct. 5, 2018, the disclosures of which are hereby incorporated by reference.

Figure 14:
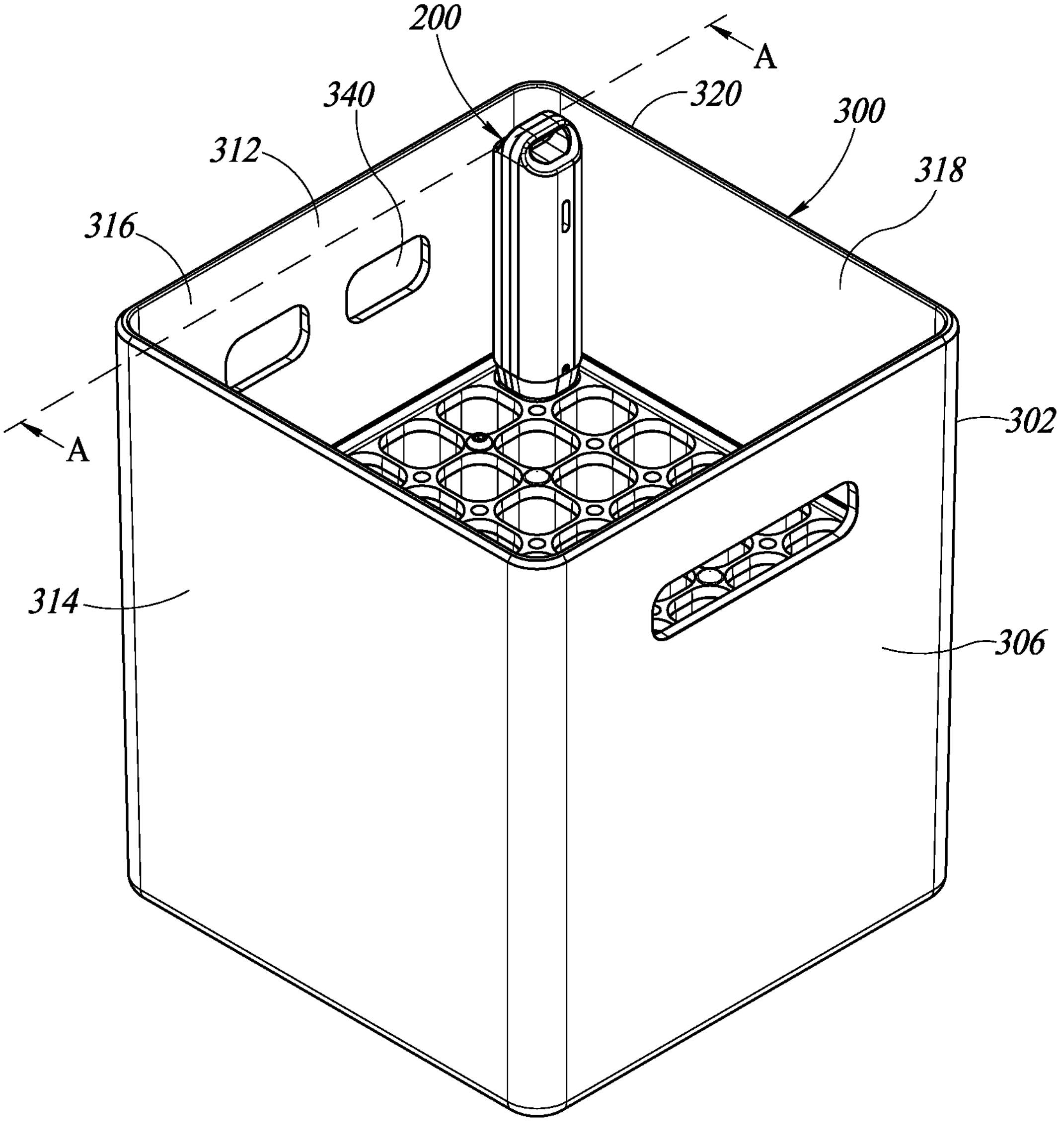
FIG. 14 is an isometric view of a storage cassette supporting a specimen container, according to one embodiment.
Figure 15:
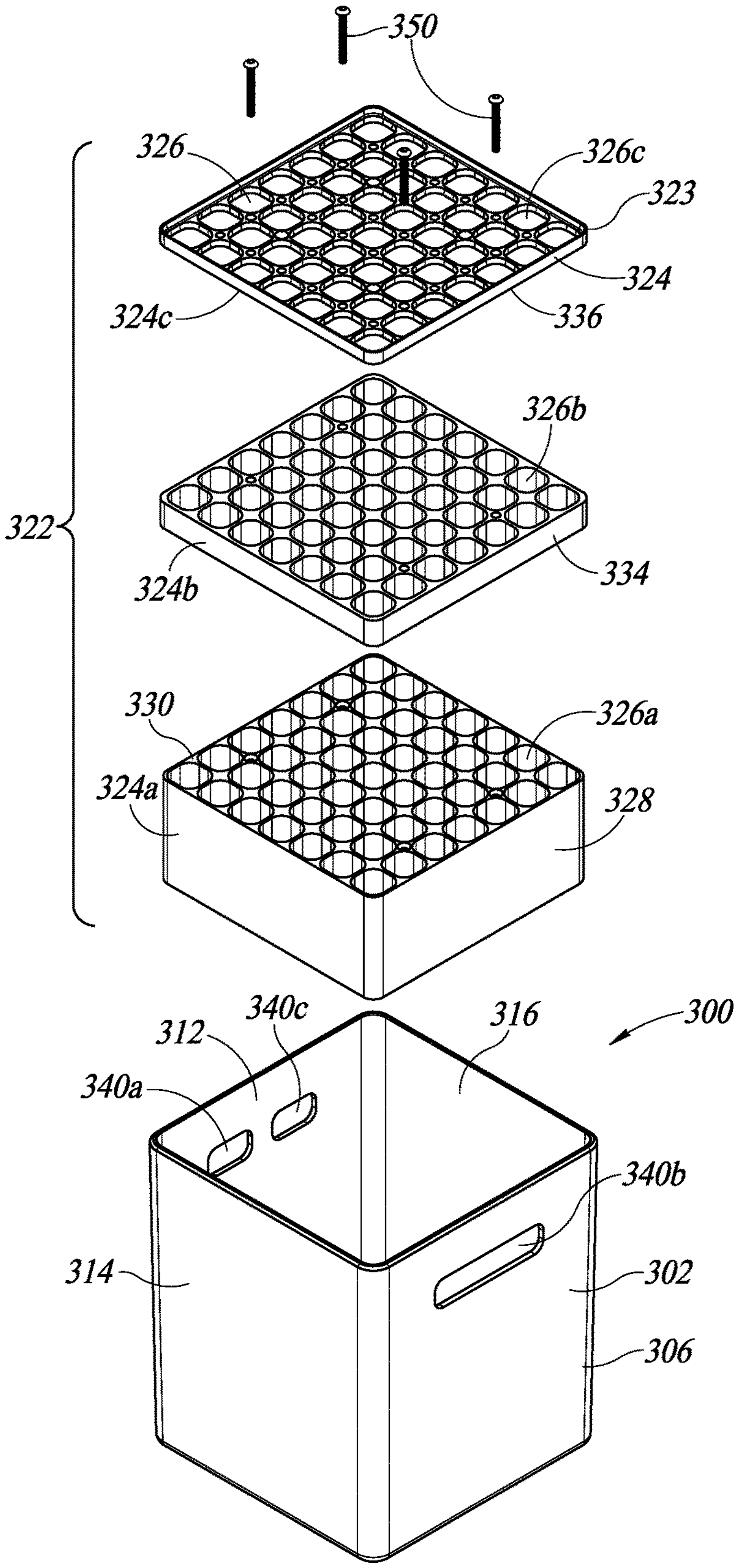
FIG. 15 is an isometric, exploded view of the storage cassette illustrated in FIG. 14.
Figure 16:
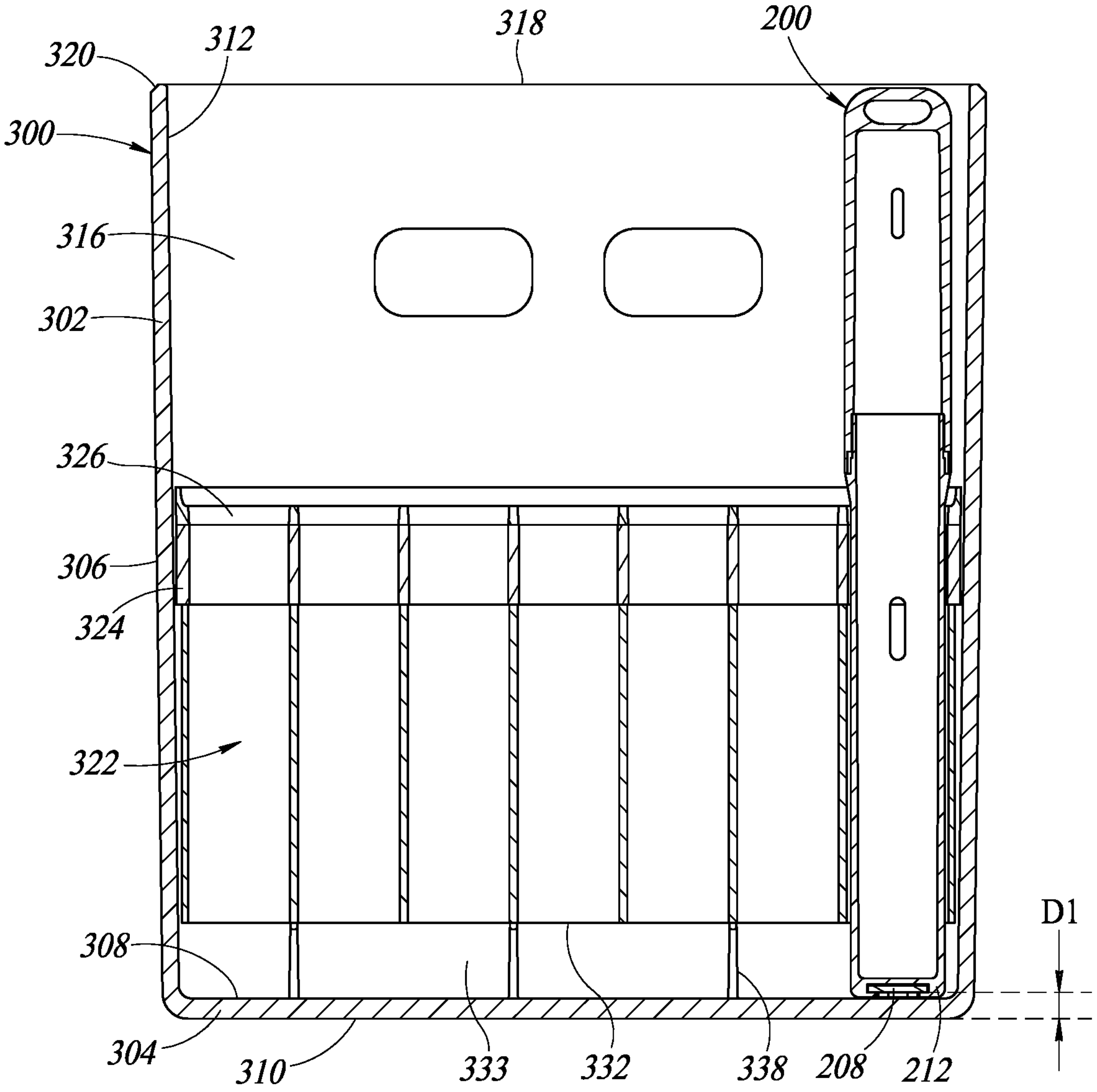
FIG. 16 is a cross-sectional view of the storage cassette illustrated in FIG. 14 along line A-A.

Referring to FIGS. 14 to 16, one or more of the specimen containers 200 may be carried by a bulk carrier, for example a storage cassette 300, of the cryogenic storage system 100, for example arrayed in a two-dimensional array (e.g., 7×7, 10×10, 8×12, 14×14). The storage cassette 300 may be designed to remain in the cryogenic refrigerator except for brief periods when removal is needed to retrieve a specimen within one of the specimen containers 200 carried by the storage cassette 300.

The storage cassette 300 maintains cryogenic conditions for an array of the specimen containers 200, for example 49 separate ones of the specimen containers 200, according to at least one implementation. As shown in the illustrated embodiment, the storage cassette 300 may include a housing 302 having a bottom 304 and at least one sidewall 306. The bottom 304 may have an inner facing surface 308 and an outer facing surface 310. The at least one sidewall 306 may have an inner facing surface 312 and an outer facing surface 314.

The inner facing surface 308 of the bottom 304 and the inner facing surface 312 of the at least one sidewall 306 may delineate an interior compartment 316 of the housing 302. The interior compartment 316 may have an interior compartment profile, and the housing 302 may have an opening 318 at a top 320 thereof, formed by the top 320, which is opposite the bottom 304 with respect to a vertical dimension, as shown in the illustrated embodiment.

The storage cassette 300 may further include a tray 322 that supports one or more of the specimen containers 200 within the interior compartment 316 of the housing 302. The tray 322 may include an outer perimeter 323 that corresponds to the inner facing surface 312 of the at least one sidewall 306 such that the tray 322 is insertable into the interior compartment 316, and once inserted relative movement of the housing 302 and the tray 322 is inhibited. According to at least one implementation, the storage cassette 300 includes a seated configuration (e.g., as shown in FIG. 16) in which the tray 322 abuts the housing 302 such that further vertical movement of the tray 322 towards the bottom 304 of the housing 302 is prevented, and lateral movement of the tray 322 relative to the housing 302 is also prevented. In the seated configuration, vertical movement of the tray 322 away from the bottom 304, and towards the opening 318 at the top 320 of the housing 302 may not be inhibited, thereby allowing removal of the tray 322 from the interior compartment 316.

The tray 322 includes a substrate 324 and one or more (e.g., a plurality of) through holes 326 extending therethrough. The through holes 326 may each be sized and shaped to correspond to one of the specimen containers 200. According to at least one implementation, the through holes 326 correspond to the specimen containers 200 such that when one of the specimen containers 200 is inserted into one of the through holes 326 relative movement of the specimen container 200 and the tray 322 is inhibited.

The tray 322, according to at least one implementation, may include a plurality of substrates (e.g., the substrate 324, referred to herein as a first substrate 324*a*, a second substrate 324*b*, and a third substrate 324*c*). As shown, each of the plurality of substrates may include a respective plurality of through holes (e.g., a first plurality of through holes 326*a*, a second plurality of through holes 326*b*, and a third plurality of through holes 326*c*. The plurality of substrates may correspond to one another such that each of the first plurality of through holes 326*a*, the second plurality of through holes 326*b*, and the third plurality of through holes 326*c* are aligned to receive one of the specimen containers 200 therein.

According to at least one implementation, the first substrate 324*a* may optionally be a thermal shunt 328. According to at least one implementation, the optional thermal shunt 328 includes a metal. As shown, the thermal shunt 328 may include a first major face 330 and a second major face 332, the second major face 332 opposed from the first major face 330 across a thickness of the thermal shunt 328. The first plurality of through holes 326*a* may extend through the thickness of the thermal shunt 328, as shown.

As shown, the thermal shunt 328 may be closely receivable in the interior compartment 316 of the housing 302. The thermal shunt 328 may have an outer profile that is asymmetrical to ensure that the thermal shunt 328 is positioned correctly in the interior compartment 316 of the housing 302. The thermal shunt 328 may be made of any of a variety of materials, preferably having a relatively large thermal mass as compared to the biological materials to be stored in the specimen containers 200 in the storage cassette 300. Suitable materials for the thermal shunt 328 may include, for example, slabs of non-ferrous metals, or metal impregnated polymers where the metal is a non-ferrous metal or the metal is in the form of small pieces, particles or strands that are sufficiently small and discontinuous as to prevent or retard the formation of currents therethrough. In at least some implementations, the thermal shunt 328 takes the form of an aluminum plate, slab, or slug.

The plurality of substrates, for example the second substrate 324*b*, may further include a thermal insulator 334 closely receivable in the interior compartment 316 of the housing 302. As shown, the thermal insulator 334 may be positioned vertically above the thermal shunt 328 (e.g., abutting the first major surface 330 of the thermal shunt 328) when inside the interior compartment 316). The thermal insulator 334 may reduce heat transfer (via conduction, convection, or both) outward from the thermal shunt 328 toward an external environment of the storage cassette 300 (e.g., out through the opening 318).

According to at least one implementation, the plurality of substrates, for example the third substrate 324*c*, may include a cover plate 336. As shown, the cover plate 336 and the thermal shunt 328 may be securable to one another, for example with one or more fasteners 350, such that the thermal insulator 334 is captured between the cover plate 336 and the thermal shunt 328. The thermal insulator 334 may include a material that is more pliable than the cover plate 336 and the thermal shunt 328, and thus is less suitable for accepting a fastener. According to at least one implementation, the cover plate 336 and the thermal shunt 328 may each be stiffer than the thermal insulator 334.

Any combination of two or more of the optional thermal shunt 328, the thermal insulator 334, and the cover plate 336 may be stacked in the interior compartment 316 of the housing 302 such that respective ones of each of the first, second, and third plurality through holes 326*a*, 326*b*, and 326*c* are axially aligned (e.g., as shown in FIG. 16). The first, second, and third plurality of through holes 326*a*, 326*b*, and 326*c* may have matching shapes, or alternatively, may have different shapes. As shown, the first, second, and third plurality through holes 326*a*, 326*b*, and 326*c* may be square with rounded corners. According to at least one implementation, the first, second, and third plurality through holes 326*a*, 326*b*, and 326*c* may be circular.

The housing 302 may include a number of set offs 338 that extend upwardly from the inner facing surface 308 of the bottom 304 into the interior compartment 316. As shown in the illustrated implementation, the set offs 338 may be positioned to support the tray 322, for example by abutting the second major face 332 of the thermal shunt 328 such that the thermal shunt 328 is spaced from the inner facing surface 308 of the bottom 304 of the housing 302. The spacing of the thermal shunt 328 from the inner facing surface 308 may delineate a volume 333 in which coolant may collect. As shown, the tray 322 may support the specimen container 200 such that a distal portion 212 of the specimen container 200 extends into the volume and is at least partially surrounded by the coolant (if present).

The storage cassette 300 may include a thickness of: the bottom 304, the thermal shunt 328, the thermal insulator 334, the set offs 338, or any combination thereof, such that a portion of the specimen container 200, for example the wireless transponder 208, is within a defined distance D1 of the outer facing surface 310 of the bottom 304. According to at least one implementation, specimen container 200 is supported directly by (i.e., is in direct contact with) the inner facing surface 308, such that the defined distance D1 is equal to a thickness of the bottom 304 of the housing 302 plus an amount (if any) the wireless transponder 208 is recessed into a bottom of the specimen container 200.

The storage cassette 300 may include a thickness of the thermal shunt 328, the set offs 338, or both, such that a specimen 220 within the specimen container 200, is surrounded by the thermal shunt 328 (in the lateral direction) and the thermal shunt 328 is spaced upward and away from the wireless transponder 208.

The housing 302 may include at least one aperture (not shown) in the bottom 304, which permits ingress and egress of coolant into and out of the interior compartment 316 of the housing 302. Alternatively, the bottom 304 may be devoid of any apertures such that coolant may not exit the interior compartment 316 through the bottom 304.

The at least one sidewall 306 may be thermally insulated. The housing 302 may include one or more through apertures 340 formed in the at least one sidewall 306. The one or more apertures 340 may include first and second apertures 340*a* and 340*b* opposite one another with respect to a lateral dimension of the housing 302. As shown in the illustrated implementation, the one or more apertures 340 may include adjacent apertures (e.g., the first aperture 340*a* and a third aperture 340*c*) formed in one surface of the at least one sidewall 306.

Figure 17:
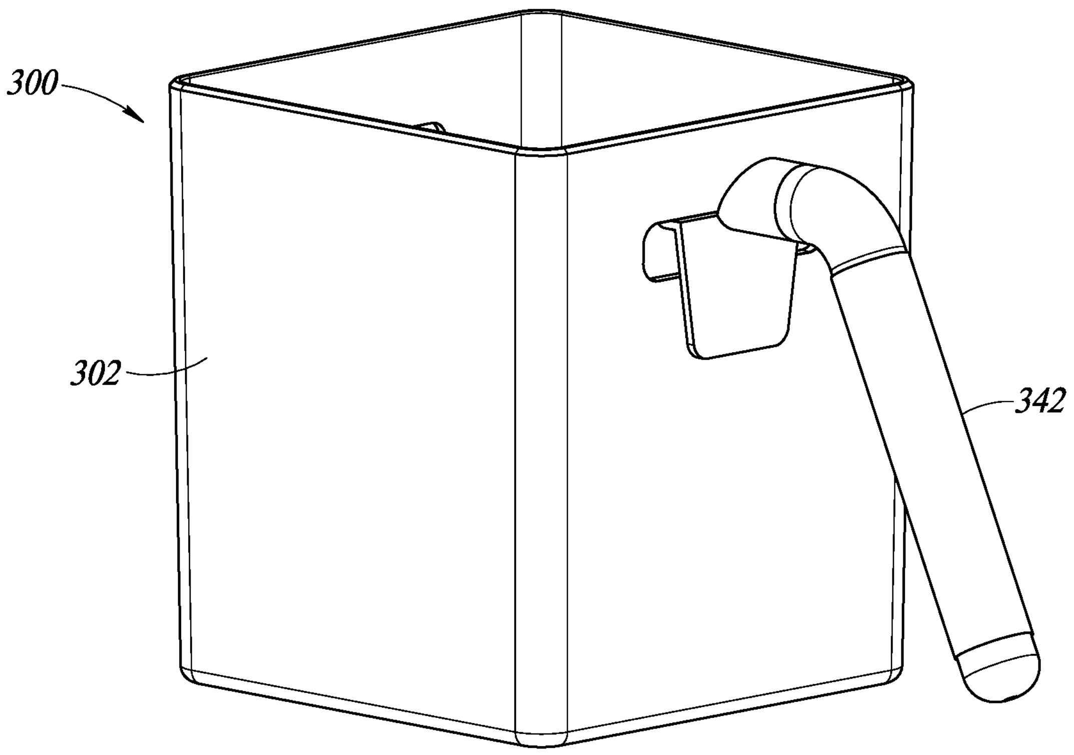
FIG. 17 is an isometric view of the storage cassette illustrated in FIG. 14 with an attached handle.
Figure 18:
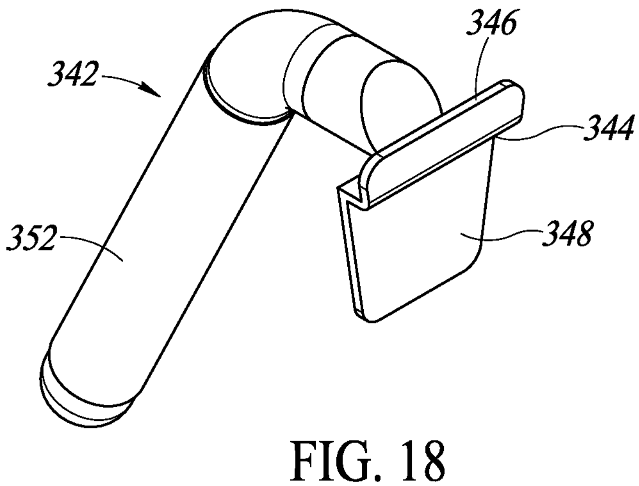
FIG. 18 is an isometric view of the handle illustrated in FIG. 17.
Figure 19:
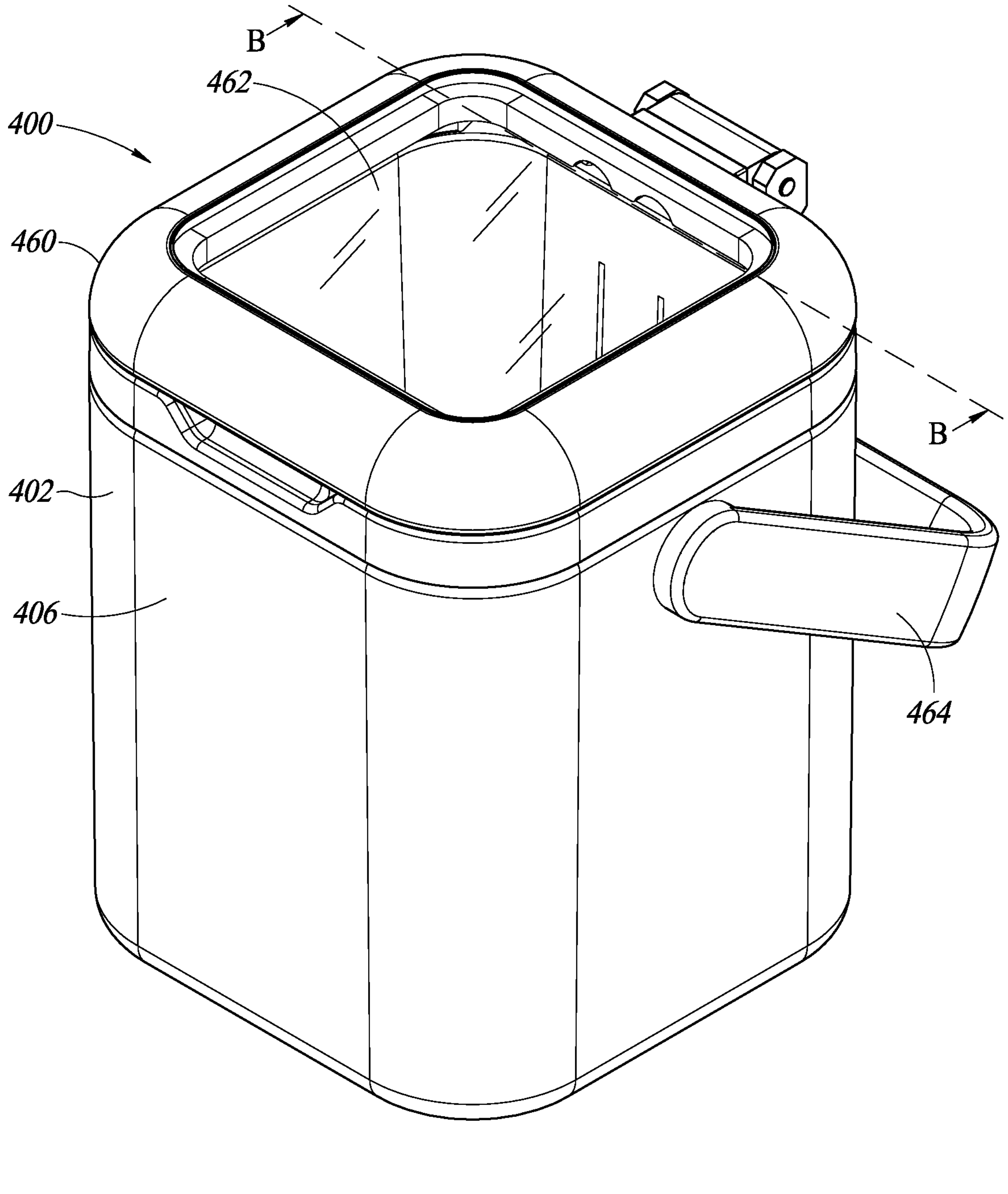
FIG. 19 is an isometric view of a specimen transporter, according to one embodiment.
Figure 20:
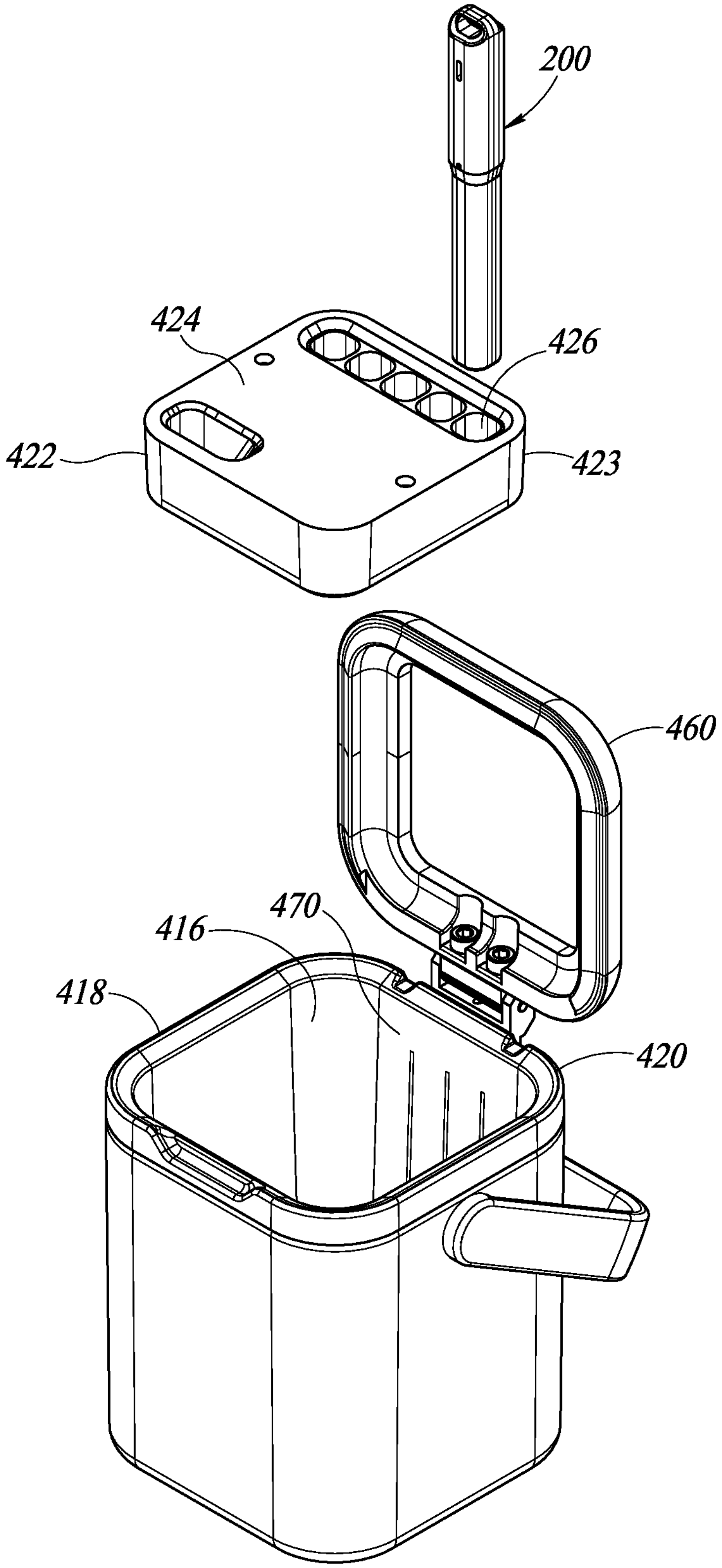
FIG. 20 is an isometric, exploded view of the specimen transporter illustrated in FIG. 19.
Figure 21:
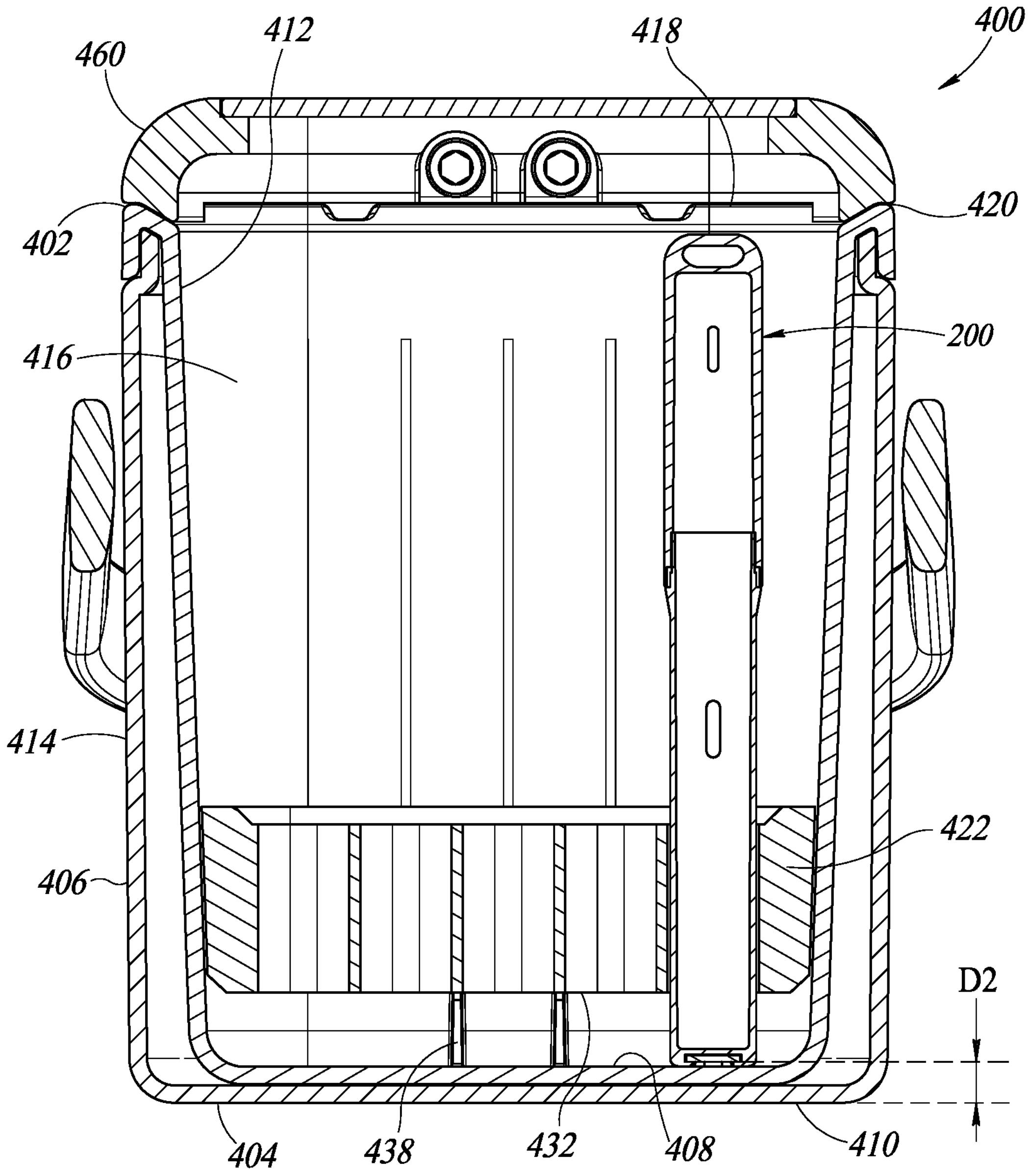
FIG. 21 is a cross-sectional view of the specimen transporter illustrated in FIG. 19 along line B-B, supporting a specimen container.

Referring to FIGS. 17 and 18, according to at least one implementation, one or more of the apertures 340 may be sized and positioned to receive a handle 342 that is removably coupleable to the housing 302. The handle 342 may be used to manipulate the storage cassette 300, as the housing 302 may be too cold to touch directly due to storage in the cryogenic environment and/or the presence of coolant (e.g., cryogenic fluid for instance liquid nitrogen) within the interior compartment 316.

According to at least one implementation, the handle 342 may include a head portion 344 that engages the storage cassette 300. As shown, the head portion 344 may include a first flange 346 insertable through one of the apertures 340 (e.g., the second aperture 340*b*) to releasably couple the handle 342 to the storage cassette 300.

The head portion 344 may include a second flange 348 that abuts the outer facing surface 314 of the at least one sidewall 306. The handle 342 may further include a grip 352 extending from the head portion 344, the grip 352 being sized to be held in a hand of an operator to facilitate manipulation of the storage cassette 300 via movement of the handle 342.

Referring to FIGS. 1 and 19 to 21, the cryogenic storage system 100 may include a second bulk carrier, for example a specimen transporter 400. The specimen transporter 400 is similar to the storage cassette 300, as described in reference to FIGS. 14 to 16, such that portions of the description of the storage cassette 300 are applicable to the specimen transporter 400, with differences called out below.

Rather than carrying a plurality of the specimen containers 200 to be stored in the cryogenic freezer 102 as described above in relation to the storage cassettes 300, the specimen transporter 400 may hold one or more of the specimen containers 200 as they are transported to or from the cryogenic freezer 102, (e.g., after harvesting or prior to implantation). The one or more of the specimen containers 200 may be carried by the specimen transporter 400, for example arrayed in a two-dimensional array (e.g., 7×7, 10×10, 8×12, and 14×14).

The specimen transporter 400 maintains cryogenic conditions for an array of the specimen containers 200, for example up to 49 separate ones of the specimen containers 200, according to at least one implementation. As shown in the illustrated embodiment, the specimen transporter 400 may include a housing 402 having a bottom 404 and at least one sidewall 406. The bottom 404 may have an inner facing surface 408 and an outer facing surface 410. The at least one sidewall 406 may have an inner facing surface 412 and an outer facing surface 414. According to at least one implementation, the housing 402 of the specimen transporter 400 includes a double wall, such that the inner facing surface 408 and the outer facing surface 410 may be part of separate walls separated by a gap (e.g., an air gap, a vacuum gap, an insulation gap). Similarly, the inner facing surface 412 and the outer facing surface 414 may be part of separate walls separated by a gap.

The inner facing surface 408 of the bottom 404 and the inner facing surface 412 of the at least one sidewall 406 may delineate an interior compartment 416 of the housing 402. The interior compartment 416 may have an interior compartment profile, and the housing 402 may have an opening 418 at a top 420 thereof, formed by the top 420, which is opposite the bottom 404 with respect to a vertical dimension, as shown in the illustrated embodiment.

The specimen transporter 400 may further include a tray 422 that supports one or more (e.g., a plurality of) the specimen containers 200 within the interior compartment 416 of the housing 402. The tray 422 may include an outer perimeter 423 that corresponds to the inner facing surface 412 of the at least one sidewall 406 such that the tray 422 is insertable into the interior compartment 416, and once inserted relative movement of the housing 402 and the tray 422 is inhibited. According to at least one implementation, the storage cassette 300 includes a seated configuration in which the tray 422 abuts the housing 402 such that further vertical movement of the tray 422 towards the bottom 404 of the housing 402 is prevented, and lateral movement of the tray 422 relative to the housing 402 is also prevented. In the seated configuration, vertical movement of the tray 422 away from the bottom 404, and towards the opening 418 at the top 420 of the housing 402 may not be inhibited, thereby allowing removal of the tray 422 from the interior compartment 416.

According to at least one implementation, the tray 422 may be the same as the tray 322, such that the same tray 322 is able to be inserted into both the interior compartment 316 and the interior compartment 416 to carry an array of the specimen containers 200. According to another implementation, the tray 422 may function similarly to the tray 322 as described above, but may have a different size, shape, or both such that the tray 422 fits within the interior compartment 416 of the specimen transporter 400, but does not fit inside the interior compartment 316 of the storage cassette 300. The tray 422 may include the plurality of substrates as described above in reference to the tray 322. Alternatively, the tray 422 may include a single substrate 424 with one or more (e.g., a plurality of) through holes 426. The number of the plurality of through holes 426 may match, or may be different than the number of the plurality of through holes 326 of the storage cassette 300.

The housing 402 may include a number of set offs 438 that extend upwardly from the inner facing surface 408 of the bottom 404 into the interior compartment 416. As shown in the illustrated implementation, the set offs 438 may be positioned to support the tray 422, for example by abutting a bottom surface 432 of the tray 422 such that the tray 422 is spaced from the inner facing surface 408 of the bottom 404 of the housing 402. The spacing of the tray 422 from the inner facing surface 408 delineates a volume in which coolant may collect. As shown, the tray 422 may support the specimen container 200 such that the distal portion 212 of the specimen container 200 extends into the volume and is at least partially surrounded by the coolant (e.g., cryogenic fluid), if present.

The specimen transporter 400 may include a thickness of: the bottom 404, the tray 422, or both, such that a portion of the specimen container 200, for example the wireless transponder 208, is within a defined distance D2 of the outer facing surface 410 of the bottom 404. According to one embodiment, specimen container 200 is supported directly by (i.e., is in direct contact with) the inner facing surface 408, such that the defined distance D2 is equal to a thickness of the bottom 404 of the housing 402 plus a thickness of the bottom of the specimen container 200. According to at least one implementation, the distance D1 and the distance D2 are equal.

The specimen transporter 400 may include a thickness of the tray 422, the set offs 438, or both, such that a specimen 220 within the specimen container 200, is surrounded by the tray 422 (in the lateral direction) and the tray 422 is spaced upward and away from the wireless transponder 208.

As shown, the specimen transporter 400 may include a cover 460 (e.g., in the form of a lid) to seal the opening 418. The at least one sidewall 406 may be devoid of any apertures, for example the first, second, and third apertures 327, 329, and 331, and the bottom 404 may be devoid of any apertures, such that when the cover 460 seals the opening 418, the interior compartment 416 is completely sealed from the external environment.

Thus, the interior compartment 416 of the specimen transporter 400 may be filled with an amount of coolant and then sealed to maintain an acceptable temperature for any specimen containers 200 contained therein. The specimen transporter 400 may include a double layer wall to ensure thermal stability of the interior compartment 416 when sealed from the external environment. The cover 460 may be permanently, for example pivotally, attached to the housing 402. The cover 460 may include a transparent portion 462 that provides visibility to the interior compartment 416 when the cover 460 is closed and sealing the opening 418.

The specimen transporter 400 may include a handle 464 that facilitates lifting the specimen transporter 400, for example by a human hand(s). The handle 464 may take the form of a rigid member. As shown in the illustrated implementation, the rigid member may be a U-shaped member. The handle 464 may be rotatably attached to the housing 402, for example to laterally opposite surfaces of the at least one sidewall 406, as shown.

The handle 464 may be rotatable into an "up" position to facilitate lifting and carrying of the specimen transporter 400. According to at least one implementation, when in the "up" position there may be enough clearance between the handle 464 and the cover 460 to allow passage of fingers of a user of the specimen transporter 400. According to another implementation, when the handle is in the "up" position fully opening the cover 460 may be blocked by interference with the handle 464. The handle 464 may be rotatable into a "down" position in which the handle 464 does not interfere with movement of the cover 460 (i.e., during transition from a closed configuration to an open configuration).

The handle 464 may take other forms. For example the handle 464 may be fixed relative to the housing 402 and the cover 460. The handle 464 may be in the form of a depression, or textured surface, for example in the at least one sidewall 406. According to one embodiment, the handle 464 may be a non-rigid member (e.g., a belt, a strap, etc.).

The specimen transporter 400 may include a vertically oriented thermal shunt 470 positioned within the interior compartment 416. The vertically oriented thermal shunt 470 may include a material with a high thermal capacity (ability to store thermal energy). Materials with a higher thermal capacity require more energy for a given temperature change than a material with a lower thermal capacity. Thermal capacity for a given material can be calculated by multiplying the volume times the density times the specific heat times the temperature change. When comparing the thermal capacity of two different materials, if the volume and the temperature change for the two materials is the same, the densities and the specific heats of the two materials determines the relative thermal capacities of the two materials.

Figure 22:
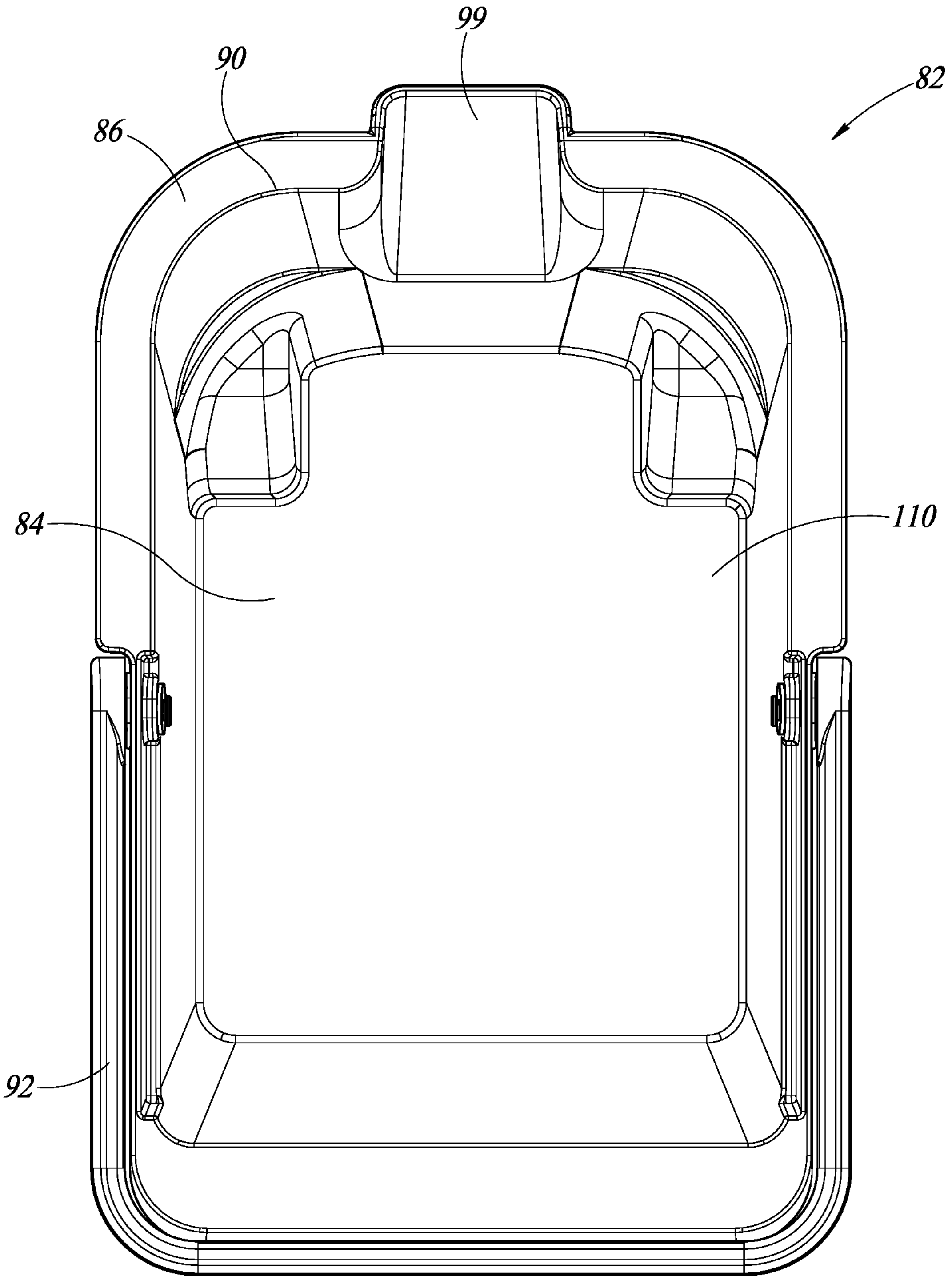
FIG. 22 is a top plan view of a bucket of the interrogation station, according to one embodiment.
Figure 23:
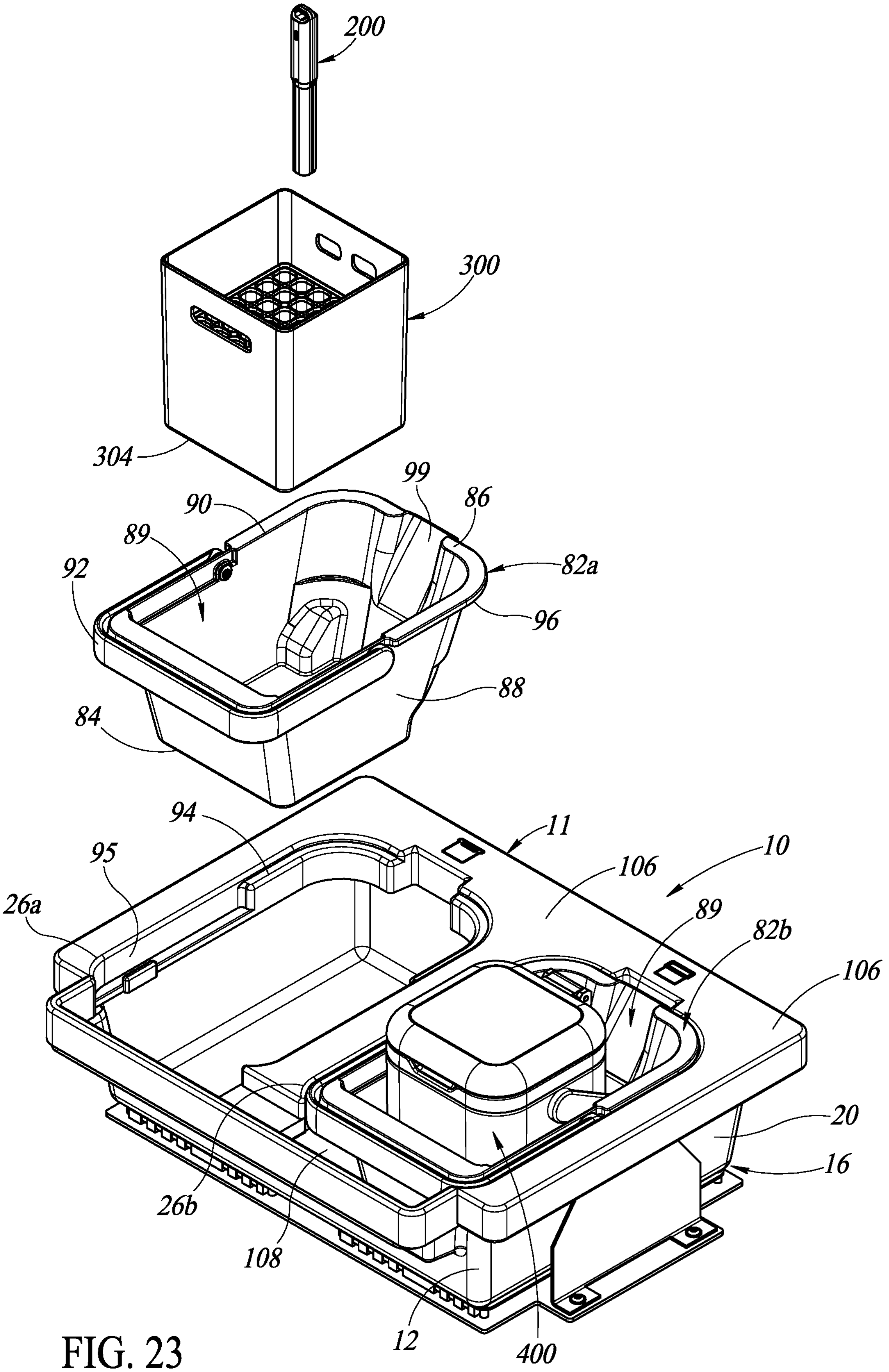
FIG. 23 is an isometric view of the interrogation station illustrated in FIG. 2 with one of the buckets illustrated in FIG. 22 in a seated configuration and another of the buckets illustrated in FIG. 22 in an unseated configuration.
Figure 24:
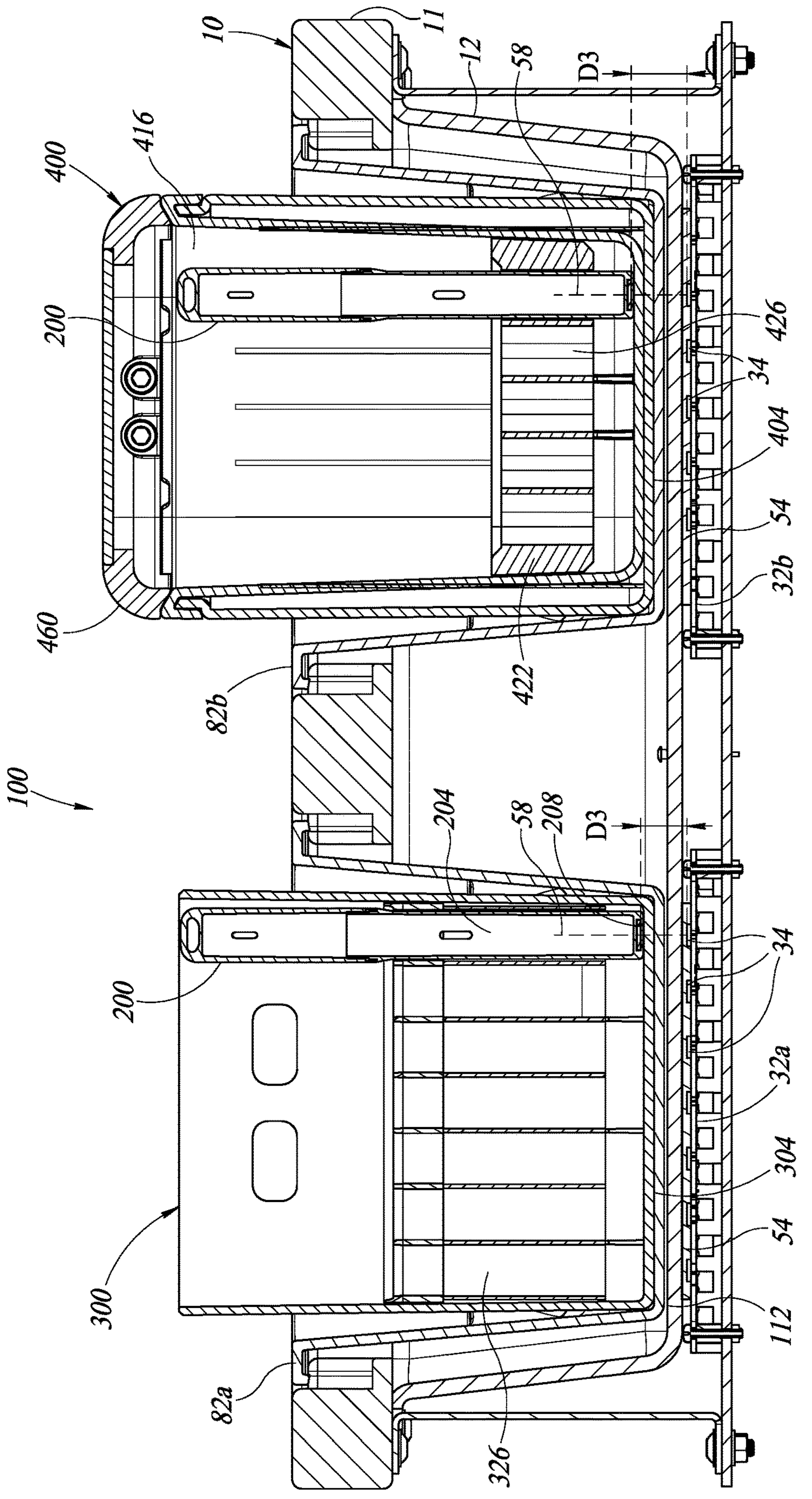
FIG. 24 is a cross-sectional view of the interrogation station illustrated in FIG. 2, supporting the storage cassette illustrated in FIG. 14 and the specimen transporter illustrated in FIG. 19, each carrying one of the specimen containers illustrated in FIG. 11.

Referring to FIGS. 22 to 24, the cryogenic storage system 100 may include at least one bucket 82 that may hold a volume of coolant (e.g., liquid nitrogen) and may support at least one bulk carrier (e.g., the storage cassette 300 or the specimen transporter 400) such that the at least one of the storage cassette 300 and the specimen transporter 400 is at least partially submerged within the volume of coolant.

As shown, the at least one bucket 82 may include a first bucket 82*a* and a second bucket 82*b*. Alternatively, the cryogenic system 100 may include one larger bucket 82 that includes the features and provides the functions of both of the separate first and second buckets 82*a*, 82*b* as described below. The first bucket 82*a* includes a bottom 84, a top 86, at least one sidewall 88 extending from the bottom 84 to the top 86 with an opening 90 at the top 86, forming a reservoir 89 which may, or may not, hold cryogenic fluid (e.g., nitrogen in liquid and/or vapor forms). The opening 90 may be sized to receive at least partially therein a container, such as one of the bulk carriers (e.g., the storage cassette 300, the specimen transporter 400, etc.) that carries at least one specimen container (e.g., the specimen container 200), therein.

The first bucket 82*a* may include a handle 92 coupled to the least one sidewall 88. The handle 92 may be pivotally coupled such that the handle 92 pivots between a deployed position and an un-deployed position. Alternatively, the handle 92 may be fixed, for example monolithic with, the first bucket 82*a*. The at least one bucket 82 may include the first bucket 82*a* and a second bucket 82*b*. The first bucket 82*a* and the second bucket 82*b* may be identical, and may be able to receive both the storage cassette 300 and the specimen transporter 400 (one at a time). Alternatively, the first bucket 82*a* and the second bucket 82*b* may have different structures, such that the first bucket 82*a* includes features that correspond to the storage cassette 300 and the second bucket 82*b* includes features that correspond to the specimen transporter 400.

The frame 11 and/or well 12 may support both the first bucket 82*a* and the second bucket 82*b* simultaneously, such that both the first bucket 82*a* and the second bucket 82*b* are removably, receivable by the at least one opening 26 in the frame 11 and into the open top 22 of the well 12. As shown, the first bucket 82*a* may be removably, receivable by the first opening 26*a* in the frame 11 and open top 22 of the well 12 and the second bucket 82*b* may be removably, receivable by the second opening 26*b* in the frame 11 and open top 22 of the well 12.

Figure 8:
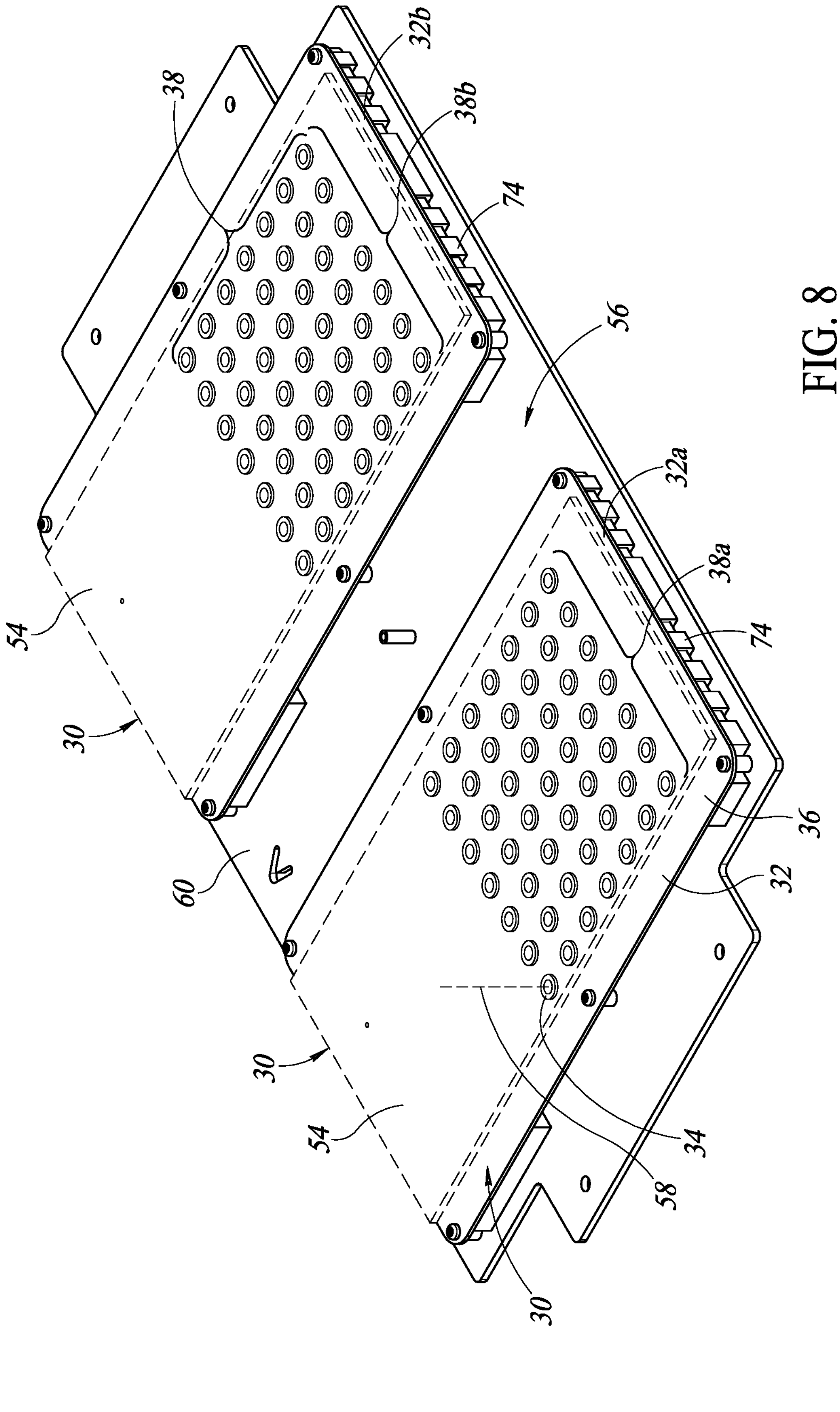
FIG. 8 is a top, isometric view of a portion of the interrogation station illustrated in FIG. 2.
Figure 9:
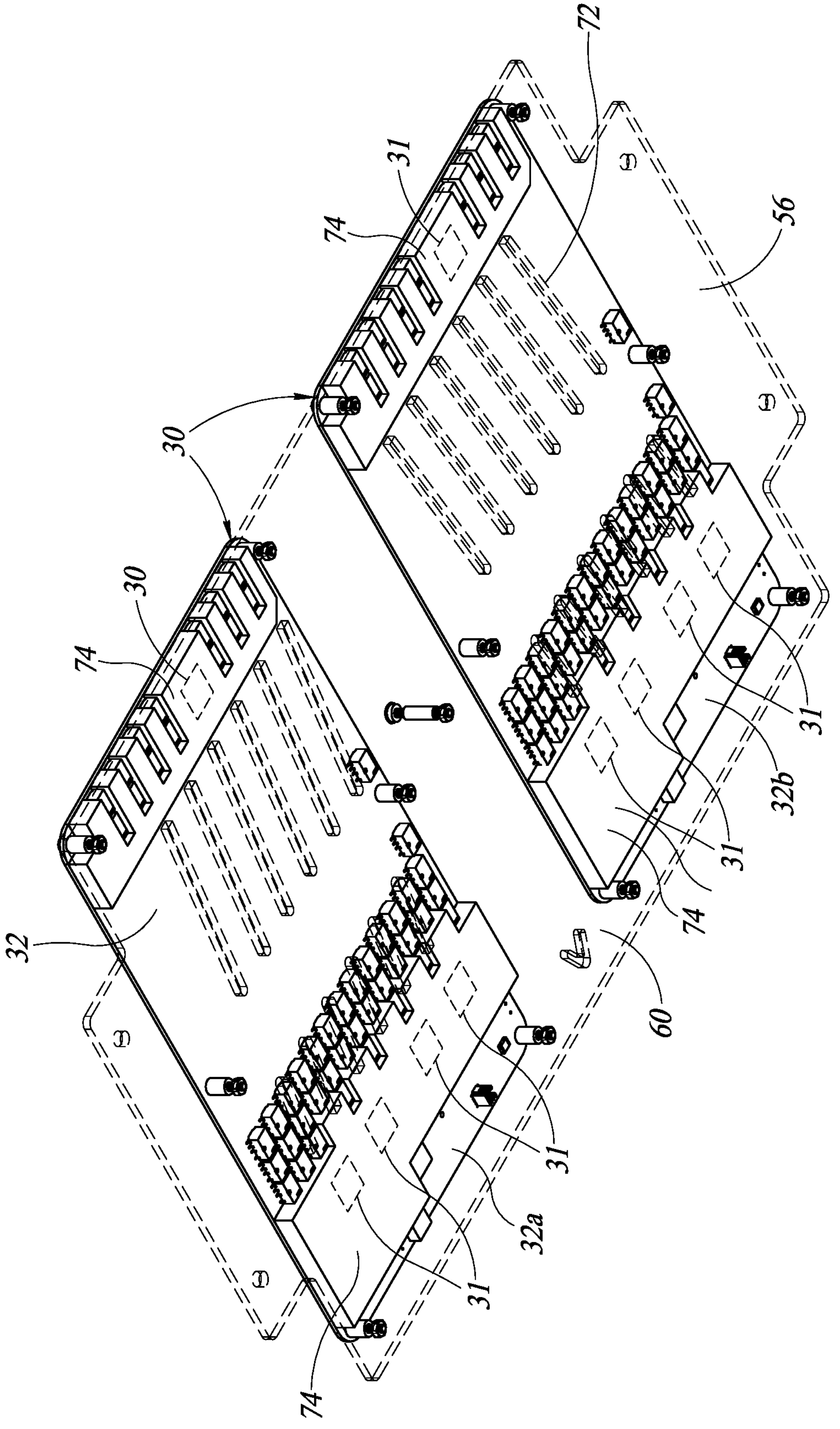
FIG. 9 is a bottom, isometric view of the portion of the interrogation station illustrated in FIG. 8.
Figure 10:
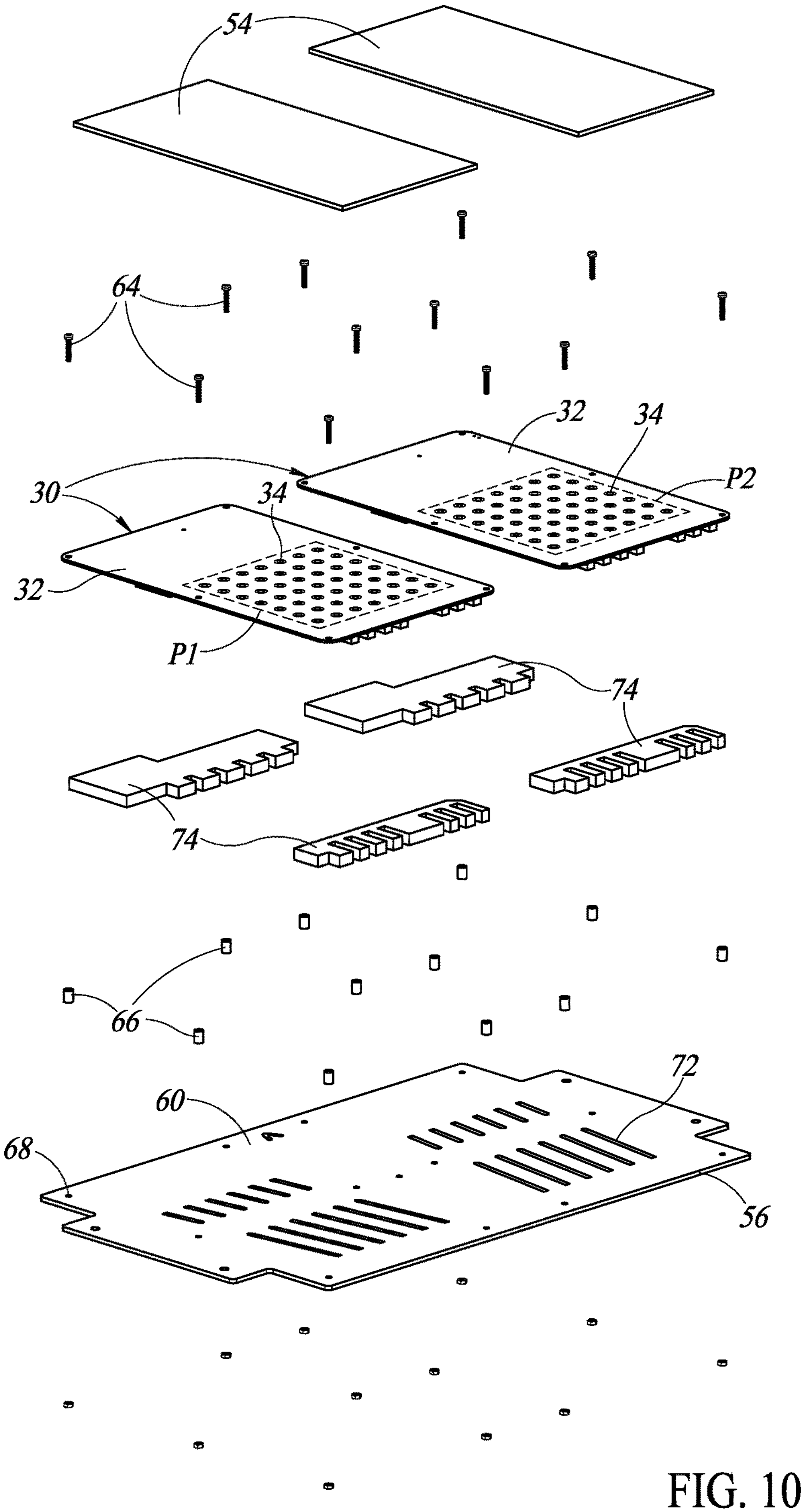
FIG. 10 is an exploded view of the portion of the interrogation station illustrated in FIG. 8.

According to at least one implementation, the frame 11 and the at least one bucket 82 include complementary structures that engage to properly vertically space and laterally align the at least one bucket 82 with the frame 11 and the well 12, and hence with the antenna array 38*a*, 38*b* (FIG. 8). The complementary structures may be shaped such that when the complementary structures are engaged, relative movement of the at least one bucket 82 with respect to the frame 11 and the well 12 is inhibited (e.g., prevented, restrained) in one or more directions and degrees of freedom. According to at least one implementation, movement of the at least one bucket 82 relative to the frame 11 and the well 12 is blocked in all directions except for vertically upward and away from the frame 11 and the well 12, which is uninhibited to facilitate removal of the at least one bucket 82 from the opening 26.

The complementary structures may include a recess 94 that extends into the frame 11 and is shaped to match at least a portion of a shape of a shoulder 96 of the at least one bucket 82. As shown, when in a seated configuration a top surface 98 of the first bucket 82*a* may be flush with a top surface 106 of the frame 11. The recess 94 may be sized to accommodate the handle 92 so that the handle 92 is also flush with the top surface 106 of the frame 11.

According to at least one implementation, the first bucket 82*a* may be held by the handle 92 (e.g., in the vertical orientation) while the first bucket 82*a* is positioned within the first opening 26*a*. After the first bucket 82*a* is in the seated configuration (i.e., the shoulder 96 is fully seated within the recess 94) the handle 92 may be rotated to fit within a portion 95 of the recess 94 such that the handle 92 is flush with the top surface 106 of the frame 11. The recess 94 may include a cutout 108 positioned so as to be adjacent the handle 92 when the handle 92 is stowed flush with the top surface 106, so as to assist with rotation of the handle 92 back to the vertical orientation to facilitate removal of the first bucket 82*a* from the well 12.

The at least one bucket 82 may include a spout 99. The spout 99 may be part of the complementary structure, for example the recess 94 may be shaped to correspond to and at least partially capture the spout 99.

The at least one bucket 82 and the storage cassette 300 may include complementary structures that engage to properly vertically space and laterally align the storage cassette 300 and the at least one bucket 82, and hence with the antenna array 38*a*, 38*b* (FIG. 8). The complementary structures of the at least one bucket 82 and the storage cassette 300 may be shaped such that when they are engaged relative movement of the storage cassette 300 and the at least one bucket 82 is inhibited (e.g., prevented) in one or more directions and degrees of freedom. According to at least one implementation, movement of the storage cassette 300 relative to the at least one bucket 82 is blocked in all directions except for vertically upward and away from the at least one bucket 82, which is uninhibited to facilitate removal of the storage cassette 300 from the at least one bucket 82. The complementary structures may include a recess 110 (e.g., that extends into or is at least partially delineated by the bottom 84) of the at least one bucket 82 and the bottom 304 of the storage cassette 300.

Similarly, the at least one bucket 82 and the specimen transporter 400 may include complementary structures that engage to properly vertically space and laterally align the specimen transporter 400 relative to the at least one bucket 82. The complementary structures of the at least one bucket 82 and the specimen transporter 400 may be shaped such that when they are engaged relative movement of the specimen transporter 400 and the at least one bucket 82 is inhibited (e.g., prevented) in one or more directions and degrees of freedom.

According to one embodiment, movement of the specimen transporter 400 relative to the at least one bucket 82 is blocked in all directions except for vertically upward and away from the at least one bucket 82, which is uninhibited to facilitate removal of the specimen transporter 400 from the at least one bucket 82. The complementary structures may include the recess 110 and the bottom 404 of the specimen transporter 400, which may be the same shape as the bottom 304 of the storage cassette 300. Alternatively, the complementary structures may include a recess shaped differently than the recess 110 and the bottom 404 of the specimen transporter 400 may be a different shape than the shape of the bottom 304 of the storage cassette 300.

When the complementary structures of the frame 11 and/or well 12 and one of the at least one bucket 82 (e.g., the first bucket 82*a*) are engaged, the complementary structures of the first bucket 82*a* and the storage cassette 300 are engaged, each of the through holes 326 is aligned with a respective one of the antennas 34. According to at least one implementation, each of the through holes 326 is laterally aligned with a respective one of the antennas 34 along one or two lateral dimensions such that the beam axis 58 of the respective antenna 34 intersects the through hole 326 (e.g., is aligned with a central axis of the through hole 326). Thus, when aligned as described above, the beam axis 58 of the antenna 34 intersects the wireless transponder 208 of the specimen containers 200 positioned within the through hole 326. According to at least one implementation, each of the antennas 34 in the array 38 is vertically spaced a nominal distance (within a defined tolerance) from any specimen containers 200 (and their associated wireless transponder 208) positioned in the through holes 326.

When the complementary structures of the frame 11 and/or well housing 12 are engaged with the structures of one of the at least one bucket 82 (e.g., the second bucket 82*b*), the complementary structures of the second bucket 82*b* and the specimen transporter 400 are engaged, each of the through holes 426 is vertically spaced from an laterally aligned with a respective one of the antennas 34. According to at least one implementation, each of the through holes 426 is laterally aligned with a respective one of the antennas 34 such that the beam axis 58 of the respective antenna 34 intersects the through hole 426 (e.g., is aligned with a central axis of the through hole 426). Thus, when aligned as described above, the beam axis 58 of the antenna 34 intersects the wireless transponder 208 of the specimen containers 200 positioned within the through hole 426. According to at least one implementation, each of the antennas 34 in the array 38 is laterally aligned with respective through holes 426 and any specimen containers 200 (and their associated wireless transponder 208) positioned therein, and is also vertically spaced from the specimen containers 200 (and their associated wireless transponder 208) by a nominal distance (e.g., 5 mm, 8 mm, 10 mm, 17 mm, 20 mm) within a defined tolerance (e.g., +/−10%).

As shown, the at least one array 38 of antennas 34 may be positioned so as to be within a defined or nominal vertical distance D3 of a portion, for example the wireless transponder 208, of the specimen container 200 when one of the storage cassette 300 or the specimen transporter 400 carrying the specimen container 200 is positioned in the at least one bucket 82, and the at least one bucket 82 is in the seated configuration with respect to the frame 11 and well 12. As shown in the illustrated embodiment, the vertical or nominal distance D3 may be measured from the antenna 38, through the insulator 54, through the bottom 18 of the well 12, through the bottom 84 of the at least one bucket 82, and through the bottom 304, 404 of either the storage cassette 300 or the specimen transporter 400 to the wireless transponder 208 of the specimen container 200. The vertical or nominal distance D3 may additionally include any gaps therebetween (e.g., an air gap 112 between the bottom 18 of the well 12 and the bottom 84 of the at least one bucket 82). According to at least one implementation, the vertical or nominal distance D3 is less than 25 mm, for example less than 20 mm, for example about 17 mm. To prevent interference, each of the structures through which the vertical distance D3 is measured may be formed from one or more materials that are transparent to wavelengths employed in RFID interrogation (e.g., radio frequencies, microwave frequencies).

Proper spacing and alignment of the antennas 34 and the wireless transponders 208 enables accurate identification of individual ones of the wireless transponders 208, and thereby identification of the associated specimen container 200, and thereby identification of the specimen carried by the specimen container 200, for example via comparison of received signal strength (e.g., RSSI). This accurate identification enables a number of the specimen containers 200 to be tightly packed, for example in a 7×7 array, to limit the volume that needs to be kept at a cryogenic temperature to maintain the viability of the specimen.

Referring to FIGS. 1 to 24, the cryogenic storage system 100 may be used to perform a method of cryogenically storing one or more biological specimens or samples (specimens and samples are used interchangeably herein). The method may include collecting one or more biological specimen from one or more entities. Each biological specimen is positioned within the vial 204 of one of the specimen containers 200. Each of the specimen containers 200 carrying a biological specimen is placed within the specimen transporter 400. According to one embodiment, each of the specimen containers 200 is positioned within a through hole 426 of the tray 422.

The interior compartment 416 of the specimen transporter 400 may maintain a cryogenic environment. According to one embodiment, a volume of coolant (e.g., liquid nitrogen) is contained within the interior compartment 416 to at least partially surround the specimen container 200. Additional specimen containers 200 may be placed within the interior compartment 416 until all of the through holes 426 of the tray 422 are occupied by one of the specimen containers 200. The cover 460 may be closed thereby sealing the interior compartment 416 from the surrounding, ambient environment.

The specimen transporter 400 may then be moved to a location with the cryogenic freezer 102 where the specimen containers 200 can be stored and maintained at cryogenic conditions long-term. The specimen transporter 400 may be placed within one of the buckets 82, for example the second bucket 82*b*. Prior to placement of the specimen transporter 400 within the reservoir 89 of the bucket 82, the bucket 82 may be placed in the seated configuration with respect to the frame 11 and well 12. A volume of coolant (e.g., cryogenic fluid, for instance nitrogen in liquid and/or vapor form) may be added to the reservoir 89 of the second bucket 82*b* such that when the specimen transporter 400 is positioned within the reservoir 89 of the second bucket 82*b*, at least a portion of the specimen transporter 400 is submerged within the coolant.

The specimen transporter 400 may be aligned with the second bucket 82*b*, for example by engaging the recess 110 and the bottom 404 of the specimen transporter 400. Once the recess 110 and the bottom 404 are engaged, the through holes 426 and the wireless transponders 208 within each of the specimen containers 200 positioned within the through holes 426 are vertically spaced from an laterally aligned with a respective one of the antennas 34 of the second array 38*b*. Optionally, a wireless transponder (not shown) of the specimen transporter 400 may be aligned with an antenna 34 of the second printed circuit board 32*b*.

One of the storage cassettes 300 may be placed within the reservoir 89 of one of the buckets 82, for example the first bucket 82*a*. The storage cassette 300 may be retrieved from within the cryogenic freezer 102, and may be supporting one of more specimen containers 200. Alternatively, the storage cassette 300 may be empty prior to placement within the reservoir 89 of the first bucket 82*a*. Prior to placement of the storage cassette 300 within the reservoir 89 of the bucket 82, the bucket 82 may be placed in the seated configuration with respect to the bucket housing 12. A volume of coolant (e.g., cryogenic fluid, for instance nitrogen in liquid and/or vapor form) may be added to the reservoir 89 of the first bucket 82*a* such that when the storage cassette 300 is positioned within the reservoir 89 of the first bucket 82*a*, at least a portion of the storage cassette 300 is submerged within the coolant.

The storage cassette 300 may be aligned with the first bucket 82*a*, for example by engaging the recess 110 and the bottom 304 of the storage cassette 300. Once the recess 110 and the bottom 304 are engaged, the through holes 326 and the wireless transponders 208 of the specimen containers 200 positioned within the through holes 326 are vertically spaced from and laterally aligned with a respective one of the antennas 34 of the first array 38*a*. Optionally, a wireless transponder (not shown) of the storage cassette 300 may be aligned with an antenna 34 of the first printed circuit board 32*a*.

One or more of the specimen containers 200 within the specimen transporter 400 may be transferred to the storage cassette 300. Prior to removal of any of the specimen containers 200, each of the wireless transponders 208 are interrogated by the RFID reader 30, thereby identifying each of the specimen containers 200 uniquely from all others of the specimen containers 200, and cataloguing the position of each of the specimen containers 200 within the specimen transporter 400.

Removal of the specimen containers 200 from the specimen transporter 400 is recognized by the RFID reader 30, and upon placement of the removed specimen containers 200 within the storage cassette 300, the chain-of-custody or database associated with the specimen container 200 is updated with the new position of the specimen container 200 within the storage cassette 300, (e.g., the specific through hole 326 of the tray 322 in which the specimen container 200 is positioned). Retrieval of biological specimen from the cryogenic freezer 102 may undergo a similar method, with the movement of the specimen container 200 reversed as it is transferred from the storage cassette 300 to the specimen transporter 400.

Once transfer of the specimen containers 200 from the specimen transporter to the storage cassette 300 is complete, the storage cassette 300 may be stored in the cryogenic freezer 102 (e.g., in vertical stacks, the vertical stacks also called racks). The stacks or racks of storage cassettes 300 may be annularly arrayed in the cryogenic freezer 102 about a central axis of the cryogenic storage tank or freezer 102. The cryogenic freezer 102 may include a turntable or conveyer in the interior thereof, on which the stacks or racks of storage cassettes 300 are carried. This allows respective stacks or racks of storage cassettes 300 to be aligned with an opening of the cryogenic freezer 102 for placement or removal.

Referring again to FIG. 1, the transfer station 104 may include a transfer surface 114 having a planar portion 116 and a peripheral wall 118 that extends upwardly from the planar portion 116 about at least a portion of a periphery 120 of the transfer surface 114. A portion of the peripheral wall 118, for example at the back 122 of the transfer station 104, may include an angled face 124 that slopes downward from the back 122 of the transfer station 104 towards the front 126 of the transfer station 104. As shown in the illustrated embodiment, the transfer surface 114 may provide a path from the cryogenic freezer 102 to the interrogation station 10. For example, the storage cassette 300 may exit the cryogenic storage freezer 102, then slide down the angled face 124, across the planar portion 116 to interrogation station 10.

Referring to FIGS. 1 to 24, at least one of the arrays 38 of the antennas 34 may be operable to read information from one or more of the wireless transponders 208 physically associated with respective specimen containers 200, storage cassettes 300, and/or specimen transporters 400. As explained in detail herein, the at least one array 38 of antennas 34 may include at least one one-dimensional or two-dimensional array of antennas, and one or more transmitters, receivers, transceivers (collectively radios), operable to cause the antennas 34 to emit interrogation signals and to receive response signals in response to the interrogations signals.

The transfer station 104 may include a dedicated user interface system including one or more of: one or more display screens, one or more touch-sensitive display screens, one or more speakers, one or more microphones, one or more keyboards, one or more pointer devices (e.g., computer mouse, trackpad, trackball), one or more haptic interfaces. The user interfaces are communicatively coupled (e.g., wired, optical, wireless or radio) with processor(s) via one or more peripheral interfaces to provide user input to the processor(s) and to receive output from the processor(s) to be presented to a user. In particular, the processor(s) may execute processor-executable instructions that cause the processor(s) to cause devices to present a user interface (e.g., a graphical user interface), for instance via a touch screen display.

Portions of the cryogenic storage system 100 may be of a conventional design. For example, the cryogenic freezer 102 and/or the picker or elevator 140 that removes storage cassettes 300 from the cryogenic freezer 102 may take the form of a commercially available automated storage system (e.g., the Bistore III Cryo −190° C. System sold by Brooks Life Sciences).

In at least some implementations, the cryogenic storage system 100 may be designed to operate with existing lab equipment, for example with conventional specimen containers (e.g., FluidX™ 24-Format tubes, FluidX™ 48-Format tubes FluidX™ 96-Format tubes available from Brooks Life Sciences) or with plates or racks (e.g., 5¼ inch by 5¼ inch plates or wells, Vision Plate™ 96 Well plate, Vision Plate™ 24 Well plate, 10×10 Cryo Rack rack, 14×14 Cryo Rack rack available from Brooks Life Sciences). Designing the cryogenic storage system 100 to operate with existing lab equipment places a number of constraints on the structure as well as the operation. For example, a two-dimensional array of antennas may be designed to successfully interrogate RFID transponders arrayed in the various available formats. This can place limits on the size (e.g., coil size) of the antennas used to interrogate and received response signals from RFID transponders (e.g., passive RFID transponders or "tags").

Smaller antennas typically reduce the range, which may require higher transmit power to compensate for the loss of range. This may be particularly true where the antennas of the wireless transponders are subject to extremely cold temperatures, for instance when the wireless transponders are immersed in a liquid nitrogen bath, while antennas of a reader are at room temperature. Also, relatively close spacing dictated by conventional equipment formats can increase the amount of cross-talk during interrogation, where an interrogation signal from one antenna excites and elicits response signals from more than one wireless transponder. Cross-talk may also increase with increasing transmit power, for instance where antenna size must be small, for instance to accommodate a spacing dictated by conventional spatial formats. The user of existing wireless transponders and readers (e.g., RFID interrogators or RFID readers) can also require specific accommodations to be made in structure and/or operation. For example, RFID readers typically employ automatic gain control.

The cryogenic storage system 100 may comprise: the plurality of antennas 34 spatially arrayed in a two-dimensional array 38, the two-dimensional array 38 having a set of dimensions or orders (e.g., 2×2, 3×3, 5×5, 4×6, 7×7, 9×9, 8×12). One or more radios may be communicatively coupled to drive the antennas 34 to emit interrogation signals to interrogate the wireless transponders 208 and to receive response signals from any of the wireless transponders 208 in a range of one or more of the antennas 34. There may, for example, be a single radio which is multiplexed to the various antennas 34. Alternatively, there may be one radio per antenna 34. Alternatively, the antennas 34 may be grouped into sets, for instance five sets, and one radio per set, multiplexed to the antennas 34 of the respective sets. In some instances the radios are transmitters, in some the radios are receivers, and in yet other instances the radios are transceivers.

Figure 25:
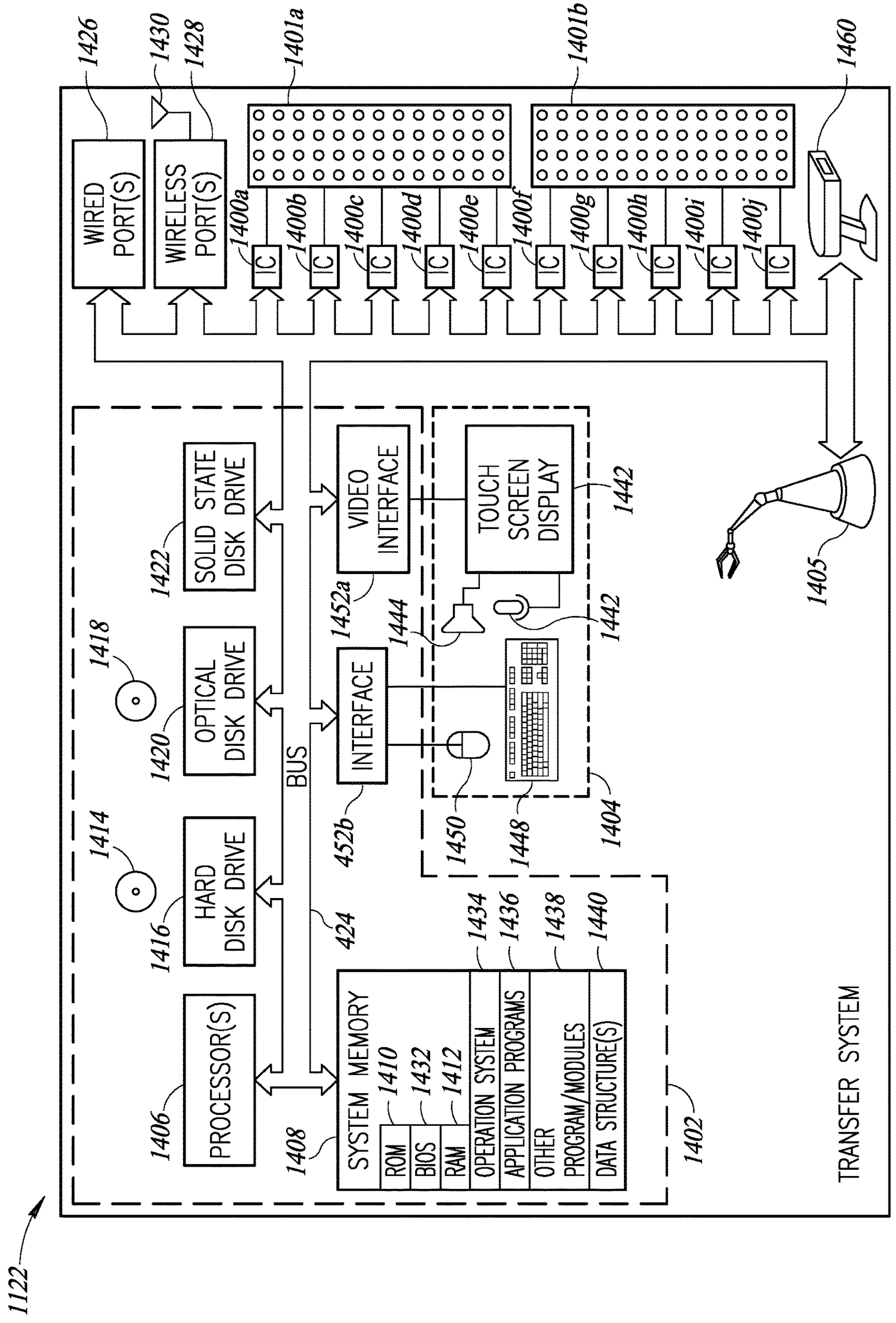
FIG. 25 is a functional block diagram of a processor-based transfer station of a cryogenic storage system, according to at least one embodiment.
Figure 26:
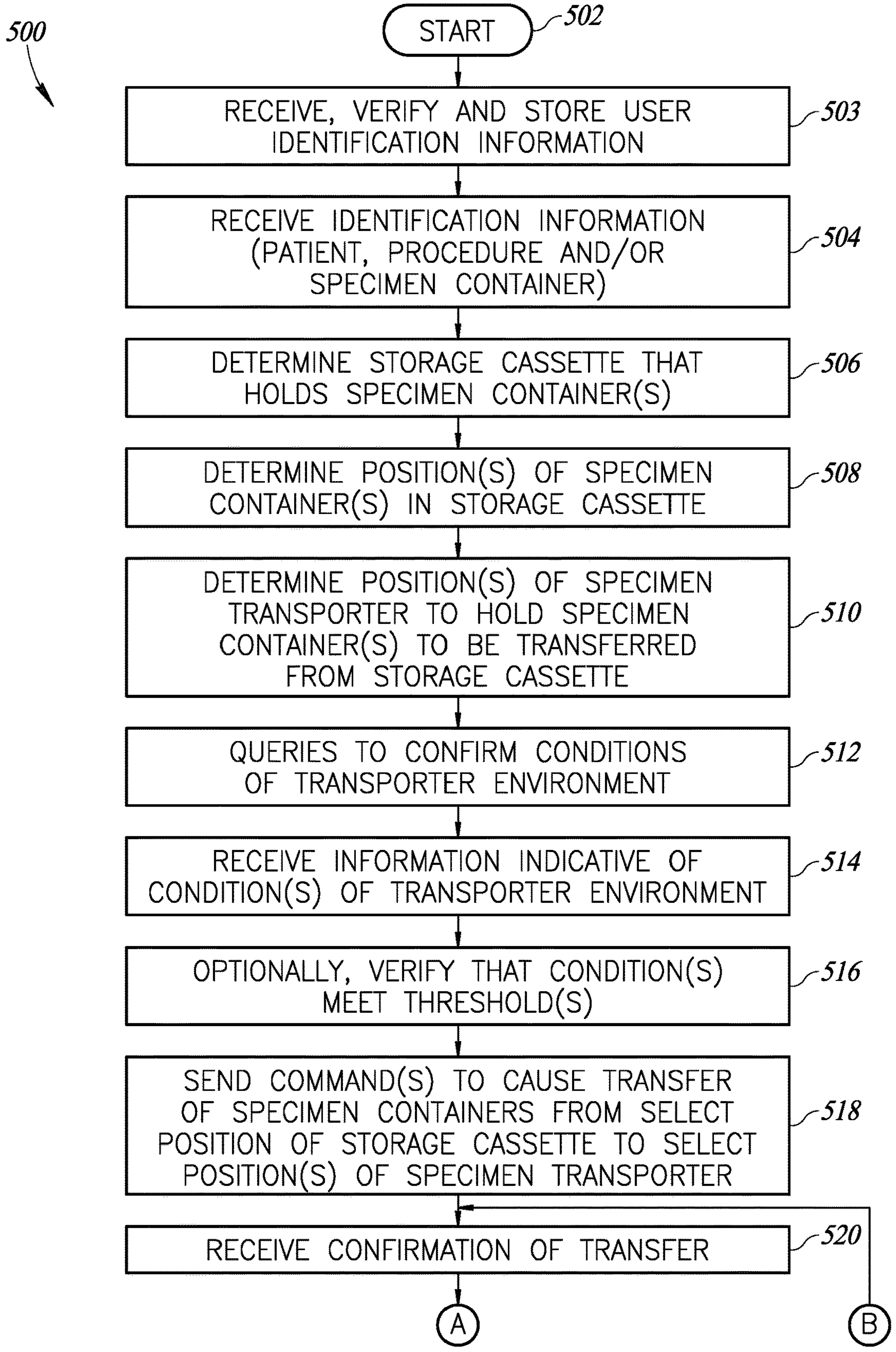
FIG. 26 is a first portion of a flow diagram showing a method of operation in a specimen transfer system to transfer specimen containers that hold biological specimens from positions in a storage cassette, which can be stored in a cryogenic freezer, to positions in a portable thermally insulated specimen transporter, according to at least one embodiment.
Figure 27:
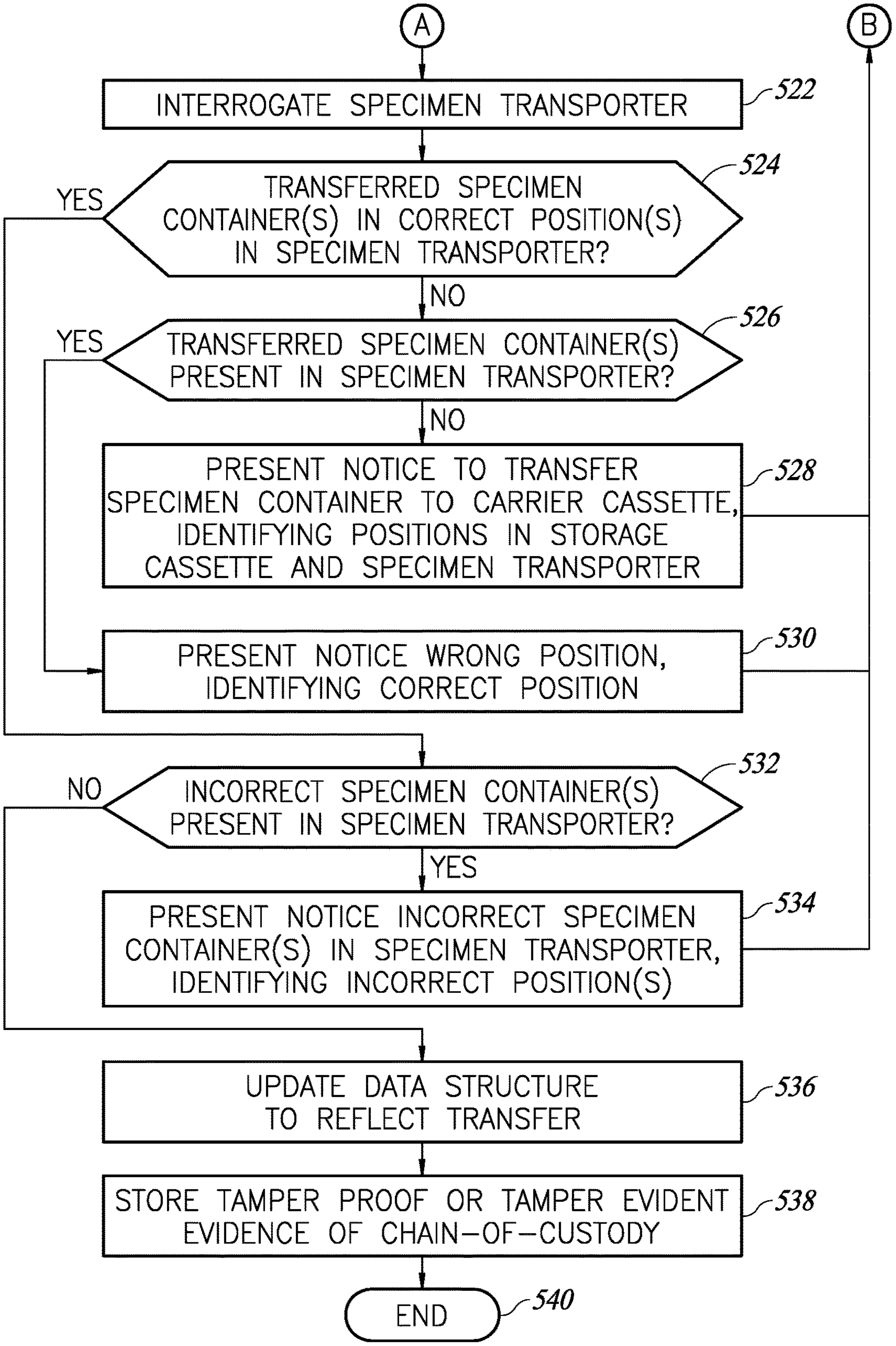
FIG. 27 is a second portion of the flow diagram illustrated in FIG. 26.
Figure 28:
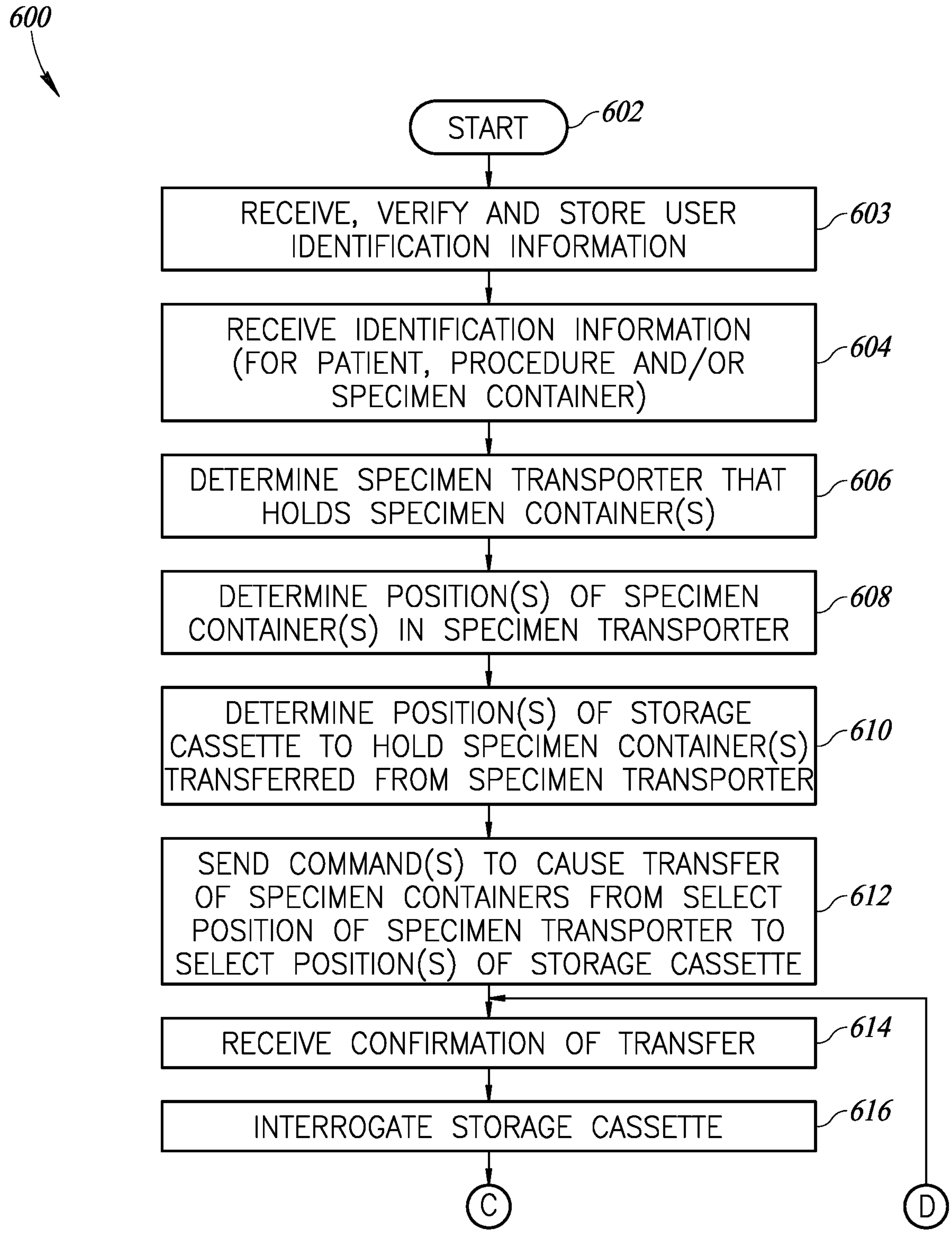
FIG. 28 is a first portion of a flow diagram showing a method of operation in a transfer system to transfer specimen containers that hold biological specimens from positions in a portable thermally specimen transporter, to positions in a storage cassette, which can be stored in a cryogenic freezer, according to at least one embodiment.
Figure 29:
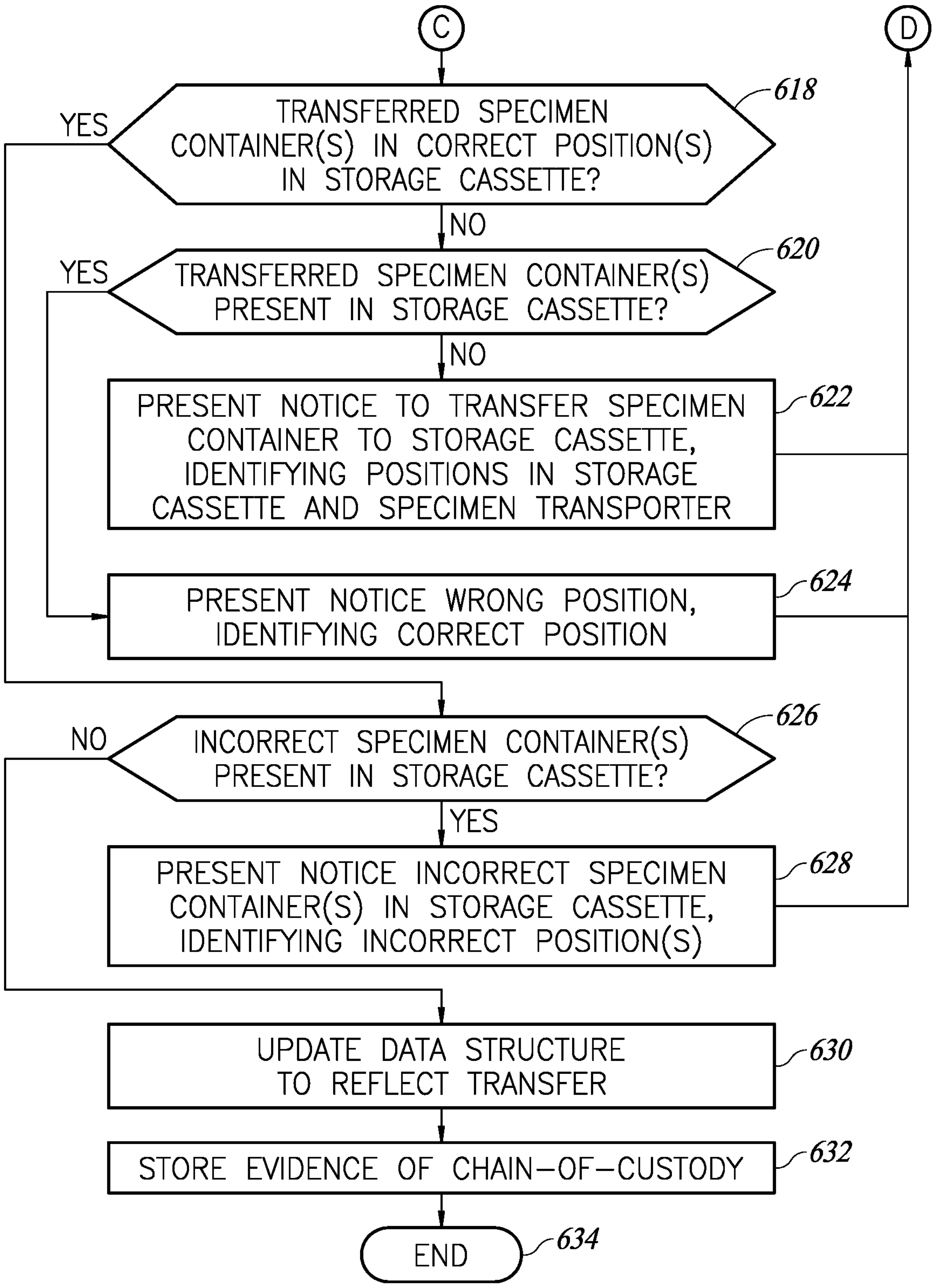
FIG. 29 is a second portion of the flow diagram illustrated in FIG. 28.

Referring to FIGS. 24 and 25, a processor-based transfer system 1122 of, or that interfaces with, the cryogenic storage system 100 of FIG. 1 may facilitate transfers, whether automated or manual, of the specimen containers 200 between the storage cassettes 300 and the specimen transporters 400. The storage cassettes 300 may be designed for long term storage in cryogenic freezers (e.g., tanks or dewars), which are typically large and heavy fixtures. The specimen transporters 400 may be designed for temporary storage, in a format that is portable.

Additional examples of suitable storage cassettes, and of the specimen transporters, which can temporarily maintain cryogenic materials at cryogenic temperatures, as wells as the specimen containers for use therewith, are described in U.S. patent application 62/900,281, filed Sep. 13, 2019; U.S. patent application 62/880,786, filed Jul. 31, 2019; U.S. patent application 62/879,160, filed Jul. 26, 2019; U.S. patent application 62/741,986, filed Oct. 5, 2018; and U.S. patent application 62/741,998, filed Oct. 5, 2018.

The processor-based transfer system 1122 may include one or more RFID reader integrated circuits 1400*a*, 1400*b*, 1400*c*, 1400*d*, 1400*e*, 1400*f*, 1400*g*, 1400*h*, 1400*i*, 1400*j* (ten shown, collectively 1400), one or more arrays of antennas 1401*a*, 1401*b* (two arrays of antennas shown, collectively 1402), a control subsystem 1402, and a user interface system 1404. The processor-based transfer system 1122 optionally includes one or more robots, for example one or more co-robots 1405 (only one shown) that interface with the picker or elevator 140 (FIG. 1) of the cryogenic storage system 100.

The RFID reader integrated circuits 1400*a*-1400*j* wirelessly interrogate and read information stored in the wireless transponders 208 physically associated with the specimen containers 200 and/or the storage cassettes 300 and/or the specimen transporters 400. The RFID reader integrated circuits 1400*a*-1400*d* each include one more transmitters, receivers or transceivers, collectively and individually referred to herein as radios. The RFID reader integrated circuits 1400*a*-1400*j* are each communicatively coupled to one or more antennas of the antenna arrays 1401*a*, 1401*b*), and are operable to emit wireless signals (e.g., interrogation signals) and/or to receive wireless signals (e.g., response signals) returned from the wireless transponders 208. The wireless signals are typically in the radio or microwave frequency bands of the electromagnetic spectrum.

Also for example, one or more machine-readable symbol readers or scanners 1460 may optically read information stored or encoded in one or more machine-readable symbols (e.g., one-dimensional or barcode symbols, two-dimensional or area code symbols) carried by, printed on, or inscribed in the specimen containers 200, the storage cassettes 300, and the specimen transporters 400.

The antenna(s) 1401*a*, 1401*b* may include antennas 34 from the at least one array 38, for example, formed or carried on one side of the printed circuit board 32, while various electrical or electronic components (e.g., inductors, resistors, capacitors, RFID reader integrated circuits 1400) may be carried on the other side of the printed circuit board 32, thereby providing a substantially flat planner surface that faces the specimen containers during use, and minimizing a distance therebetween (e.g., less than or equal to 2 mm, less than 10 mm, less than 17 mm, less than 20 mm).

The control subsystem 1402 may include one or more processors 1406, for example, one or more of: one or more microcontrollers, one or more microprocessors, one or more central processing units, one or more digital signal processors (DSPs), one or more graphics processing units (GPUs), one or more application specific integrated circuits (ASICs), one or more field programmable gate arrays (FPGAs), and/or one or more programmable logic controllers (PLCs). The control subsystem 1402 may include one or more nontransitory storage media, for example, one or more nonvolatile storage media and/or one or more volatile storage media, for example a system memory 1408 that includes one or more of: one or more read only memories (ROMs) 1410, one or more random access memories (RAMs) 1412, one or more FLASH memory, one or more magnetic disk 1414 and associated drives 1416, one or more optical disk drives 1418 and associated drives 1420, one or more solid state drives 1422, one or more cache memories, and/or one or more registers of one or more processors 1406.

The control subsystem 1402 may include one or more communications channels 1424 (e.g., buses) that communicatively couple the processor(s) with the storage media. The control subsystem 1402 may include one or more communications ports, for example one or more wired communications ports 1426, wireless communications ports 1428 (e.g., Wi-Fi and/or Bluetooth radios and associated antennas 1430; infrared transceivers) that provide for communications between the control subsystem 1402 and external devices (e.g., dedicated control system of conventional cryogenic refrigerator system with, or without picker or elevator 140).

The processor(s) 1406 of the control subsystem 1402 are operable to execute logic, for example to execute one or more algorithms stored as process-executable instructions by the one or more nontransitory storage media. Suitable algorithms are set out herein. Process-executable instructions may, for example, include a basic input/output operating system (BIOS) 1432, for example stored in ROM 1410. Process-executable instructions may, for example, include an operating system (OS) 1434, for example stored in RAM 1412 during execution. Process-executable instructions may, for example, include one or more application programs 1436, which provide the logic to collect user information, map transfers between storage and carrier cassettes, verify that the specimen containers are at the correct positions in the carrier or storage cassettes, and establish evidence of a chain-of-custody for the same, the applications program(s) stored, for example, in RAM 1412 during operation.

Process-executable instructions may include one or more other programs or modules 1438, for example to provide for communications with external devices and/or to control operation of co-robot(s) 1405, and which may be stored, for example, in RAM 1412 during execution. One or more data structures 1440 may store information, for example information that identifies specific users, identifies specific clinicians, identifies specific patients, identifies specific procedures, identifies specific specimen containers and associates the specific specimen containers with specific patients, and that maps specimen containers to respective storage cassettes and/or carrier cassettes. The data structures 1440 may take a variety of forms including databases, data sets, records and fields, tables, linked lists, trees, binary trees, etc. The data structures 1440 may be stored, for example, in RAM 1412 during execution.

The processor(s) 1406 of the control subsystem 1402 are communicatively coupled operable (e.g., wired, optical, wireless or radio) to receive information from the RFID reader integrated circuits **1400*a*-1400*j*, and optionally to control operation of one or more of the RFID reader integrated circuits 1400*a*-1400*j*. The processor(s) 1406 of the control subsystem 1402 are also operable to receive user input from, and provide user out to, one or more user interface devices of the user interface system 1404, to allow a human user to interact with the processor-based transfer system 1122**.

The user interface system 1404 may, for example, include one or more of: one or more display screens (e.g., two display screens), one or more touch-sensitive display screens 1442, one or more speakers 1444, one or more microphones 1446, one or more keyboards 1448, one or more pointer devices 1450 (e.g., computer mouse, trackpad, trackball), one or more haptic interfaces. The user interfaces 1404 are communicatively coupled (e.g., wired, optical, wireless or radio) with the processor(s) via one or more peripheral interfaces **1452*a*, 1452*b* to provide user input to the processor(s) 1406 and to receive output from the processor(s) 1406 to be presented to a user. In particular, the processor(s) 1406 may execute processor-executable instructions that cause the processor(s) to cause devices to present a user interface (e.g., a graphical user interface), for instance via a touch screen display 1442**. Various user interface elements are illustrated and described herein.

In some instances the radios are transmitters, in some the radios are receivers, and in yet other instances the radios are transceivers. The processor-based control system 1122 may be communicatively coupled to the radio(s). The processor-based control system 1122 determines, based on response signals received in response to a given interrogation, whether at least one of the wireless transponders 208 is located at an expected position of one of the storage cassette 300 or the specimen transporter 400. In response to a determination that the at least one of the wireless transponders 208 is not located at the expected position of one of the storage cassette 300 or the specimen transporter 400 the processor-based control system 1122 may cause a signal indicative of an occurrence of an unexpected condition to be provided. To cause a signal indicative of an occurrence of an unexpected condition to be provided, the processor-based control system 1122 may cause a visual prompt to be presented and/or cause a signal to be provided to a robot that causes the robot to make a movement.

For each response signal received in response to a given interrogation, the processor-based control system 1122 may determine which response signal was returned from one of the wireless transponders 208 that is closest wireless transponder 208 to the antenna 34 that emitted the respective interrogation signal to which the wireless transponders 208 are responding. For example, for each response signal received in response to a given interrogation, at least one of the processor-based control system 1122 or the at least one radio may normalize a respective received signal strength indicator (RSSI) value that indicates a received signal strength of the response signal to account for any automatic gain adjustment introduced by the at least one radio.

For instance, for each interrogation, the processor-based control system 1122 determines which of the respective normalized RSSI values for the response signals received in response to a given interrogation has the largest absolute value. To determine which of the respective normalized RSSI values for the response signals received in response to a given interrogation has the largest absolute value for each interrogation, the processor-based control system 1122 may compare the respective normalized RSSI values for the received response signals to one another.

To determine which response signal was returned from one of the wireless transponders 208 that is closest wireless transponder 208 to the antenna 34 that emitted the respective interrogation signal to which the wireless transponders 208 are responding, the processor-based control system 1122 may further compare a respective read rate to one another for each of the wireless transponders 208 that respond, the respective read rate representative of a total number of times the respective wireless transponder 208 is read per a unit of time. To determine which response signal was returned from one of the wireless transponders 208 that is the closest wireless transponder 208 to the antenna 34 that emitted the respective interrogation signal to which the wireless transponders 208 are responding, the processor-based control system may additionally or alternatively further compare a respective response time to one another for each of the wireless transponders 208 that respond, the respective response time representative of an amount of time the respective wireless transponder 208 takes to initially respond to the interrogation.

Before the processor-based control system 1122 determines whether at least one of the wireless transponders 208 is located at an expected position of one of the storage cassette 300 or the specimen transporter 400, the processor-based control system 1122 may further cause a prompt to be presented which indicates a position of one of the storage cassette 300 or the specimen transporter 400 from which to transfer one of the specimen containers 200 along with the wireless transponder 208 associated therewith and a position of the other of the storage cassette 300 or the specimen transporter 400 to which to transfer the specimen container 200, the expected position being the position of the other of the storage cassette 300 or the specimen transporter 400 to which the specimen container 200 is to be transferred.

The processor-based control system 1122 may further determine, based on response signals received in response to one or more interrogations, whether there are any specimen containers 200 marked by respective ones of the wireless transponders 208 in an unexpected position in one of the storage cassette 300 or the specimen transporter 400, and in response to a determination that there is at least one specimen container 200 marked by respective one of the wireless transponders 208 in an unexpected position in one of the storage cassette 300 or the specimen transporter 400, cause a signal indicative of an occurrence of an unexpected condition to be provided.

The processor-based control system 1122 may further determine, based on response signals received in response to one or more interrogations, whether there are any specimen containers 200 marked by respective ones of the wireless transponders 208 that are missing from the one of the storage cassette 300 or the specimen transporter 400, and in response to a determination that there is at least one specimen containers 200 marked that is missing from the one of the storage cassette 300 or the specimen transporter 400, cause a signal indicative of an occurrence of an unexpected condition to be provided. To cause a signal indicative of an occurrence of an unexpected condition to be provided, the processor-based control system 1122 may cause a presentation of a signal to be provided that is indicative of the occurrence of the unexpected condition and indicative of at least one of an incorrect location and a correct location for the specimen container 200 in the at least one of the storage cassette 300 or the specimen transporter 400.

Additionally, speed is typically important to commercial operation. To increase speed, antennas may be grouped into a plurality of sets, the sets which are operated in parallel with one another. For example, a two-dimensional array of ninety-six antennas, arranged as a 8×12 array, may be grouped to four sets denominated A, B, C D, and corresponding to four quadrants of the two-dimensional array (e.g., sets A, B, C D arranged clockwise starting with A in an upper left quadrant). The position in each quadrant may be represented by a pair of integers representing a row and column. In operation, a first antenna 1,1 of a first set A, a first antenna 1,1 of a second set B, a first antenna 1,1 of a third set C, and a first antenna 1,1 of a fourth set D, may be operated to concurrently transmit respective interrogation signals (e.g., carrier waves) during a first interrogation cycle.

The other antennas of the first set A, second set B, third set C, and fourth set D may be monitored for response signals as part of the first interrogation cycle. Subsequently, a second antenna 1,2 of the first set A, a second antenna 1,2 of the second set B, the second antenna 1,2 of a third set C, and the second antenna 1,2 of the fourth set D, may be operated to concurrently transmit respective interrogation signals (e.g., carrier waves) during a second interrogation cycle. The other antennas of the first set A, second set B, third set C, and fourth set D may be monitored for response signals as part of the second interrogation cycle.

Subsequent interrogation cycles may cycle through the remaining antennas of the sets, operating one of the antennas from each set to transmit interrogations currently with one another. In some implementations, operation may result in there being a fixed distance between the transmitting antennas of any two sets. For instance, during any given interrogation cycle the transmitting antenna in one set may be in the same relative position within its own set as the relative position of the other transmitting antennas in the other sets. This is similar to the operation described above, where the row/column pair of the transmitting antenna of each set match one another during each interrogation cycle.

Alternatively, operation may result in there being a maximum achievable distance between the concurrently transmitting antennas during any given interrogation cycle. For instance, a first antenna 1,1 of a first set A, a sixth antenna 1,6 of a second set B, a nineteenth antenna 4,1 of a third set C, and a twenty-fourth antenna 4,6 of a fourth set D, may be operated to concurrently transmit respective interrogation signals (e.g., carrier waves) in a first interrogation cycle. Thus, during the first interrogation cycle antennas at the opposite four corners of the two-dimensional array concurrently transmit interrogation signals. During subsequent interrogation cycles, the antennas in each set A, B, C, D may be stepped through in an order that matches one another, for example transmitting interrogation signals from antennas successively along a row, then successively from a next row, etc.

While four sets are described, any number of sets of antennas may be employed. While two patterns of antenna activation are described, other patterns may be employed. Also, while generally described as employing all antennas to monitor for a response signal except the antenna that most recently emitted the interrogation signal, other approaches may be employed. For example, all antennas may be monitored, including the antenna that most recently emitted the interrogation signal. In such implementations, delay will typically be employed to allow resonance in the transmitting antenna to decay sufficiently as to allow detection of a response signal. Alternatively, only a select one or select ones of the antennas may be employed to monitor for response signals. For instance, in some implementation, only the antenna that most recently transmitted the interrogation signal is monitored for a receipt of a response signal, typically after a delay time.

Referring to FIGS. 24 to 27 a method 500 of operation to transfer specimen containers (e.g., the specimen containers 200) from storage cassettes (e.g., the storage cassettes 300), which can be stored in a cryogenic freezer (e.g., the cryogenic freezer 102), to a portable thermally insulated cryogenic carrier (e.g., the specimen transporter 400), is described according to at least one illustrated implementation. The method 500 may be performed when the storage cassette 300 and the specimen transporter 400 are each positioned within the interrogation station 10 such that the specimen containers 200 contained therein are aligned with the antennas 34 as described above.

The method 500 starts at 502. For example, the method may start in response to a powering on of the processor-based transfer system 1122 or a component thereof, in response to detection of the storage cassette 300 and/or the specimen transporter 400 at a reader, receipt of a user input, or a call from a calling routine or program.

At 503, the processor-based transfer system 1122 receives, verifies and stores user identification information. The user identification information may take a variety of forms, for example a user identifier, a password or passphrase, and/or biometric data (e.g., digital fingerprint, digital iris scan, facial features).

At 504, the processor-based transfer system 1122 receives identification information. The identification information may, for example, be received as user input via a user interface, or as an electronic transfer of information from another system, for instance from a clinical procedure management processor-based system. The identification information may, for example, include a patient name, unique patient identifier, patient data of birth, procedure type or unique procedure identifier, specimen container identifier, and/or specimen identifier.

At 506, the processor-based transfer system 1122 determines which of the storage cassettes 300 that holds the one or more specimen containers 200 to be retrieved. For example, one or more of the specimen containers 200 may hold biological specimens or tissue to be used in a given procedure on a given patient. The processor-based transfer system 1122 may, for example, query a data structure using the identification information.

At 508, the processor-based transfer system 1122 determines one or more positions of the identified specimen containers 200 in the storage cassette 300. The processor-based transfer system may, for example, query a data structure using the identification information.

At 510, the processor-based transfer system 1122 determines position(s) of the specimen transporter 400 to hold the specimen container(s) 200 transferred from the storage cassette 300. The processor-based transfer system 1122 may, for example, query a data structure using the identification information.

At 512, the processor-based transfer system 1122 causes a presentation of queries to confirm conditions of carrier environment. Queries may be presented visually or aurally via a user interface. Queries may include a request that the user confirm that the specimen transporter 400 is ready, that there is adequate coolant (e.g., liquid nitrogen) in the specimen transporter 400, and that the coolant is adequately cold (e.g., at or below approximate negative 190° C.).

At 514, the processor-based transfer system 1122 receives information indicative of condition(s) of an environment of the specimen transporter 400. The information may, for example, be received via a user interface.

Optionally at 516, the processor-based transfer system 1122 verifies that one or more conditions meet one or more thresholds. For example, a user may enter a fluid level and/or a temperature of the fluid, which can be compared to a threshold level and/or threshold temperature.

At 518, the processor-based transfer system 1122 sends one or more commands to cause transfer of the specimen containers 200 from select position of the storage cassette 300 to select position(s) of the specimen transporter 400. In the case of manual transfers, the commands may be presented to a user as prompts via the user interface. In the case of automated transfers, the commands can be in the form of a motion plan for execution by a robot or other mechanical conveyance.

At 520, the processor-based transfer system 1122 receives a confirmation of transfer. Confirmation may be received from a user via a user interface. Alternatively, confirmation may come from a processor-based system, for example a robot, indicating that a series of operations have been completed.

At 522, the processor-based transfer system 1122 interrogates the specimen transporter 400. For example, a reader may sequentially interrogate each position in the specimen transporter 400, determining which positions have a wireless transponder tagged specimen container, and even the identity of each specimen container at each position that has a specimen container. Such may, for example, be implemented via an RFID reader or interrogator (e.g., the RFID reader 30), with a two-dimensional array of antennas (e.g., the antennas 34) which are arranged to be in registration with respective positions of the specimen transporter 400 and spaced at a nominal distance therefrom.

At 524, the processor-based transfer system 1122 determines whether the transferred specimen container(s) 200 are in correct the position(s) in the specimen transporter 400. The processor-based transfer system 1122 can query a data structure to determine, for each position of the specimen transporter 400 that is supposed to have a specimen container 200, the identity of the specimen container 200 that is supposed to be at that position. The processor-based transfer system 1122 compares the actual mapping, as determined via interrogation, with the intended mapping, to verify that each specimen container 200 is in the correct position, to identify specimen containers 200 in incorrect positions, to identify missing specimen containers 200 and/or specimen containers 200 that should not be in the specimen transporter 400, as described below.

If it is determined at 524 that the transferred specimen container(s) 200 are not in correct position(s) in the specimen transporter 400, then the processor-based transfer system 1122 attempts to determine what specific errors have occurred. For example, at 526 the processor-based transfer system 1122 determines whether the transferred specimen container(s) 200 are present in the specimen transporter 400. If it is determined at 526 that the transferred specimen container(s) 200 are not present in the specimen transporter 400, then at 528 the processor-based transfer system 1122 causes a user interface to present a prompt to transfer the specimen container 200 from the storage cassette 300 to the specimen transporter 400, identifying the specific positions in the storage cassette 300 and the specimen transporter 400, and control returns to 520 to await receipt of a confirmation that the transfer has been completed.

Alternatively, the processor-based transfer system 1122 provides instructions to a robot to implement the transfer of the specimen container(s) 200. If it is determined at 526 that the transferred specimen container(s) 200 is (are) present in the specimen transporter 400, then at 530 the processor-based system 1122 causes the user interface to present a notification or prompt to move the specimen container(s) 200 to the correct position(s) in the specimen transporter 400, including an identification of the position from which the specimen container 200 should be moved from and the position to which the specimen container 200 should be moved. Control then returns to await receipt of a confirmation that the transfer has been completed at 520.

If it is determined at 524 that the transferred specimen container(s) 200 are in correct position(s) in the specimen transporter 400, then optionally at 532 the processor-based transfer system 1122 determines whether there are any incorrect specimen container(s) 200 present in the specimen transporter 400. If it is determined at 532 that there are incorrect specimen container(s) 200 present in the specimen transporter 400, then at 534 the processor-based transfer system 1122 causes the user interface to present a notification that there are incorrect specimen container(s) 200 in the specimen transporter 400, identifying incorrect position(s). Control then returns to await receipt of a confirmation that the transfer has been completed at 520. If it is determined at 532 that there are not incorrect specimen container(s) 200 present in the specimen transporter 400, then control passes to 536.

At 536, the processor-based transfer system 1122 updates a data structure to reflect transfer. The data structure can, for example take the form of a database, table, tree structure or linked list.

At 538, the processor-based transfer system 1122 stores evidence of chain-of-custody, preferably in a tamper proof or tamper evident form. The evidence of chain-of-title may, for example be stored in a block-chain form.

The method 500 terminates at 540, for example until invoked again.

Referring to FIGS. 24 to 25 and 28 to 29 a method 600 of operation to transfer specimen containers (e.g., the specimen containers 200) from storage cassettes (e.g., the storage cassettes 300), which can be stored in a cryogenic freezer (e.g., the cryogenic freezer 102), to a portable thermally insulated cryogenic carrier (e.g., the specimen transporter 400), is described according to at least one illustrated implementation. The method 500 may be performed when the storage cassette 300 and the specimen transporter 400 are each positioned within the interrogation station 10 such that the specimen containers 200 contained therein are aligned with the antennas 34 as described above.

The method 600 starts at 602. For example, the method may start in response to a powering on of the processor-based transfer system 1122 or a component thereof, in response to detection of the storage cassette 300 and the specimen transporter 400 at a reader, receipt of a user input, or a call from a calling routine or program.

At 603, the processor-based transfer system 1122 receives, verifies and stores user identification information. The user identification information may take a variety of forms, for example a user identifier, a password or passphrase, and/or biometric data (e.g., digital fingerprint, digital iris scan, facial features).

At 604, the processor-based transfer system 1122 receives identification information. The identification information may, for example, be received as user input via a user interface, or as an electronic transfer of information from another system, for instance from a clinical procedure management processor-based system. The identification information may, for example, include a patient name, unique patient identifier, patient data of birth, procedure type or unique procedure identifier, specimen container identifier, and/or specimen identifier.

At 606, the processor-based transfer system 1122 determines which specimen transporter 400 holds the one or more specimen containers 200 to be stored in the cryogenic storage freezer 102. For example, one or more specimen containers 200 may hold biological specimens or tissue collected from a given procedure on a given patient. The processor-based transfer system 1122 may, for example, query a data structure using the identification information.

At 608, the processor-based transfer system 1122 determines one or more positions of the identified specimen containers in the specimen transporter 400. The processor-based transfer system 1122 may, for example, query a data structure using the identification information.

At 610, the processor-based transfer system 1122 determines position(s) of storage cassette to hold specimen container(s) transferred from the specimen transporter 400. The processor-based transfer system 1122 may, for example, query a data structure using the identification information.

At 612, the processor-based transfer system 1122 sends one or more commands to cause transfer of specimen containers from select position of the specimen transporter 400 to select position(s) of the storage cassette 300. In the case of manual transfers, the commands may be presented to a user as prompts via the user interface. In the case of automated transfers, the commands can be in the form of a motion plan for execution by a robot or other mechanical conveyance.

At 614, the processor-based transfer system 1122 receives a confirmation of transfer. Confirmation may be received from a user via a user interface. Alternatively, confirmation may come from a processor-based system, for example a robot, indicating that a series of operations have been completed.

Optionally at 616, the processor-based transfer system 1122 interrogates the storage cassette 300. For example, a reader may sequentially interrogate each position in the storage cassette 300, determining which positions have a wireless transponder tagged specimen container 200, and even the identity of each specimen container at each position that has a specimen container 200. Such may, for example, be implemented via an RFID reader or interrogator, with a two-dimensional array of antennas 34 which are arranged to be in registration with respective positions of the storage cassette 300 and spaced vertically at a nominal distance with respect thereto.

Optionally at 618, the processor-based transfer system 1122 determines whether the transferred specimen container(s) 200 are in correct the position(s) in the storage cassette 300. The processor-based transfer system 1122 can query a data structure to determine, for each position of the storage cassette 300 that is supposed to have a specimen container 200, the identity of the specimen container 200 that is supposed to be at that position. The processor-based transfer system 1122 compares the actual mapping, as determined via interrogation, with the intended mapping, to verify that each specimen container 200 is in the correct position, to identify specimen containers 200 in incorrect positions, to identify missing specimen containers 200 and/or specimen containers 200 that should not be in the storage cassette 300, as described below.

If it is determined at 618 that the transferred specimen container(s) 200 are not in correct position(s) in storage cassette 300, then at 620 the processor-based transfer system 1122 determines whether the transferred specimen container(s) 200 are present in storage cassette 300. If it is determined at 620 that the transferred specimen container(s) 200 are not present in storage cassette 300, then at 622 the processor-based transfer system 1122 causes a user interface to present a prompt to transfer the specimen container 200 from the specimen transporter 400 to the storage cassette 300, identifying the specific positions in the specimen transporter 400 and the storage cassettes 300. Alternatively, the processor-based transfer system 1122 provides instructions to a robot to implement the transfer of the specimen container(s) 200. Control then returns to await receipt of a confirmation that the transfer has been completed at 614. If it is determined at 620 that the transferred specimen container(s) 200 is (are) present in the storage cassette 300, then at 624 the processor-based system 122 causes the user interface to present a notification or prompt to move the specimen container(s) 200 to the correct position(s) in the storage cassette 300, including an identification of the position from which the specimen container 200 should be moved from and the position to which the specimen container 200 should be moved. Control then returns to await receipt of a confirmation that the transfer has been completed at 614.

If it is determined at 618 that the transferred specimen container(s) 200 are in correct position(s) in the storage cassette 300, then optionally at 626 the processor-based transfer system 1122 determines whether there are incorrect specimen container(s) 200 present in the storage cassette 300. If it is determined at 620 that there are incorrect specimen container(s) 200 present in the storage cassette 300, then at 628 the processor-based transfer system 1122 causes the user interface to present a notification that there are incorrect specimen container(s) 200 in the storage cassette 300, identifying incorrect position(s). Control then returns to await receipt of a confirmation that the transfer has been completed at 614. If it is determined at 620 that there are not incorrect specimen container(s) 200 present in the storage cassette 300, then control passes to 630.

At 630, the processor-based transfer system 1122 updates a data structure to reflect transfer. The data structure can, for example take the form of a database, table, tree structure or linked list.

At 632, the processor-based transfer system 1122 stores evidence of chain-of-custody, preferably in a tamper proof or tamper evident form. The evidence of chain-of-title may, for example be stored in a block-chain form.

The method 600 terminates at 634, for example until invoked again.

The various implementations and embodiments described above can be combined to provide further implementations and embodiments. All of the commonly assigned US patent application publications, US patent applications, foreign patents, and foreign patent applications referred to in this specification and/or listed in the Application Data Sheet, including but not limited U.S. patent application 62/900,281, filed Sep. 13, 2019; U.S. patent application 62/880,786, filed Jul. 31, 2019; U.S. patent application 62/879,160, filed July 26, 2019; U.S. patent application 62/741,986, filed Oct. 5, 2018; U.S. patent application 62/741,998, filed Oct. 5, 2018; U.S. patent application 62/927,566, filed Oct. 29, 2019; U.S. patent application 63/082,789, filed Sep. 24, 2020; U.S. patent application 63/128,732, filed Dec. 21, 2020, and U.S. patent application 63/186,593, filed May 10, 2021, are each incorporated herein by reference, in their entirety. These and other changes can be made to the embodiments in light of the above-detailed description.

In general, in the following claims, the terms used should not be construed to limit the claims to the specific implementations and embodiments disclosed in the specification and the claims, but should be construed to include all possible implementations and embodiments along with the full scope of equivalents to which such claims are entitled. Accordingly, the claims are not limited by the disclosure.

The invention claimed is:

1. An interrogation station comprising:

a frame and a well, the well having a bottom, a top opposite the bottom, and at least one sidewall that extends upwardly from the bottom towards the top, wherein the bottom, the at least one sidewall, and the top collectively delineate an interior cavity of the well, at least a portion of the top of the well being open, the frame including at least one opening that provides passage through the open top of the well so as to provide access to the interior cavity from an exterior thereof;

at least one array of antennas arranged within a plane;

at least one printed circuit board which carries the at least one array of antennas; and a coupler that secures the at least one array of antennas beneath the bottom of the well at a defined perpendicular distance from the bottom of the well in a vertical direction, and with the at least one array of antennas laterally aligned with a respective one of the at least one opening of the frame, wherein the coupler includes a slotted plate which supports the at least one printed circuit board at a location between the well and the slotted plate, and the slotted plate includes a plurality of slots that extend through a thickness of the slotted plate and that are aligned with components mounted on a lower side of the at least one printed circuit board along the vertical direction, and wherein the coupler includes a pair of brackets that secure the slotted plate to the well.

2. The interrogation station of claim 1 wherein the at least one opening of the frame includes a first opening and a second opening separated from one another by a portion of the frame that is positioned between the first opening and the second opening along a lateral direction that is perpendicular to the vertical direction.

3. The interrogation station of claim 2 wherein the at least one array of antennas includes a first array of antennas and a second array of antennas, and the first array of antennas is laterally aligned with the first opening along a first lateral direction and a second lateral direction, and the second array of antennas is aligned with the second opening along the first lateral direction and the second lateral direction.

4. The interrogation station of claim 3 wherein the first array of antennas includes a plurality of rows of antennas, each of the plurality of rows being evenly spaced from adjacent ones of the plurality of rows along the first lateral direction that is perpendicular to the vertical direction, and a plurality of columns of antennas, each of the plurality of columns being evenly spaced from adjacent ones of the plurality of columns along the second lateral direction that is perpendicular to both the vertical direction and the first lateral direction.

5. The interrogation station of claim 1 wherein the at least one array of antennas is positioned beneath the bottom of the well at a location in which the at least one array of antennas is less than 5 mm from the bottom of the well as measured along the vertical direction.

6. The interrogation station of claim 1, further comprising an insulator positioned between the bottom of the well and the at least one array of antennas.

7. The interrogation station of claim 1, further comprising a hydrophobic material positioned between at least a portion of the slotted plate and a portion of the at least one printed circuit board.

8. The interrogation station of claim 7 wherein the at least a portion of the slotted plate includes multiple, discrete portions of the slotted plate.

9. The interrogation station of claim 1 wherein the coupler secures the printed circuit board to the well without entirely enclosing the printed circuit board, and the interrogation station comprise an integral unit sized to be mounted in an opening at least adjacent a surface of a transfer station.

10. The interrogation station of claim 1, further comprising:

at least one bucket including a bucket bottom and at least one bucket sidewall extending from the bucket bottom such that the bucket bottom and the at least one bucket sidewall collectively delineate a reservoir to contain a volume of coolant, wherein the at least one bucket is receivable in the at least one opening of the frame such that the bucket bottom is laterally aligned with the at least one array of antennas along the first and the second lateral directions.

11. The interrogation station of claim 10 wherein the at least one bucket and the frame include complementary structures shaped such that when the complementary structures are engaged movement of the at least one bucket relative to the frame and the well is blocked in all directions except for upward and away from the well along the vertical direction.

12. The interrogation station of claim 11 wherein when the complementary structures are engaged and movement of the at least one bucket relative to the frame and the well is blocked in all directions except for upward and away from the well along the vertical direction, the bucket bottom is separated from the bottom of the well by an air gap.

13. The interrogation station of claim 11 wherein the complementary structures include a recess formed by the frame and at least a portion of an outer perimeter of the at least one bucket.

14. The interrogation station of claim 13 wherein the at least one bucket includes a handle pivotally attached to the at least one bucket sidewall, and the recess includes a portion to receive the handle.

15. The interrogation station of claim 11 wherein when the complementary structures are engaged and movement of the at least one bucket relative to the frame and the well is blocked in all directions except for upward and away from the well along the vertical direction, an entirety of the at least one bucket is flush with or recessed with respect to a top surface of the frame.

16. The interrogation station of claim 10, further comprising:

a bulk carrier including a bulk carrier bottom and at least one bulk carrier sidewall that cooperatively delineate a bulk carrier interior compartment, the bulk carrier including a tray having a plurality of through holes extending therethrough, each of the plurality of through holes sized to receive a specimen container that holds a biological specimen, wherein the bulk carrier is receivable within the reservoir of the at least one bucket such that the plurality of through holes are each laterally aligned with respective antennas of the at least one array of antennas along the first and the second lateral directions.

17. The interrogation station of claim 16 wherein the bulk carrier is a first bulk carrier, the interrogation station further comprising a second bulk carrier, the second bulk carrier including a second tray having a second plurality of through holes extending therethrough, each of the second plurality of through holes sized to receive a specimen container that holds a biological specimen, wherein the second bulk carrier is receivable within the reservoir of the at least one bucket such that the second plurality of through holes are each laterally aligned with respective antennas of the at least one array of antennas along the first and the second lateral directions.

18. The interrogation station of claim 17 wherein the first bulk carrier is receivable within one of the at least one bucket such that the plurality of through holes of the first bulk carrier are each laterally aligned with a first subset of the at least one array of antennas along the first and the second lateral directions, and the second bulk carrier is simultaneously receivable within another of the at least one bucket such that the second plurality of through holes are each laterally aligned with a second subset of the at least one array of antennas along the first and the second lateral directions, and none of the antennas of the first subset are included in the second subset.

19. The interrogation station of claim 17 wherein the first bulk carrier and the at least one bucket include complementary structures shaped such that when the complementary structures of the first bulk carrier and the at least one bucket are engaged, movement of the first bulk carrier relative to the at least one bucket is blocked in all directions except for along the vertical direction, upward and away from the at least one bucket.

20. The interrogation station of claim 16, further comprising:

at least one specimen container with a body that delineates an interior to at least partially enclose a biological specimen, the at least one specimen container further including a wireless transponder physically associated with the body, the wireless transponder carrying identification information of for the biological specimen, wherein the body is receivable within the plurality of through holes of the bulk carrier such that when the bulk carrier is received within the reservoir of the at least one bucket and the plurality of through holes are each laterally aligned with respective antennas of the at least one array of antennas along the first and the second lateral directions, the wireless transponder is laterally aligned with one of the antennas of the at least one array of antennas along the first and the second lateral directions.

* * * * *